(12) United States Patent
Soreq et al.

(10) Patent No.: US 8,722,876 B2
(45) Date of Patent: May 13, 2014

(54) ANTISENSE OLIGONUCLEOTIDES AGAINST AChE IN THE TREATMENT OF GASTROINTESTINAL INFLAMMATION DISORDERS

(71) Applicant: Yissum Research Development Company of the Hebrew University of Jerusalem Ltd., Jerusalem (IL)

(72) Inventors: Hermona Soreq, Jerusalem (IL); Raz Yirmiya, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 13/899,922

(22) Filed: May 22, 2013

(65) Prior Publication Data

US 2013/0310441 A1  Nov. 21, 2013

Related U.S. Application Data

(63) Continuation of application No. 13/835,267, filed on Mar. 15, 2013, which is a continuation-in-part of application No. 13/351,171, filed on Jan. 16, 2012, now abandoned, which is a continuation of application No. 11/788,321, filed on Apr. 18, 2007, now abandoned, which is a continuation of application No. 11/187,719, filed on Jul. 21, 2005, now abandoned, which is a continuation-in-part of application No. PCT/IL2004/000978, filed on Oct. 26, 2004.

(51) Int. Cl.
*C07H 21/04* (2006.01)
*A61K 48/00* (2006.01)

(52) U.S. Cl.
USPC ........................... 536/24.5; 514/44 R

(58) Field of Classification Search
None
See application file for complete search history.

(56) References Cited

U.S. PATENT DOCUMENTS

| | | | |
|---|---|---|---|
| 5,891,725 | A | 4/1999 | Soreq et al. |
| 6,495,579 | B1 | 12/2002 | Hunter |
| 7,074,915 | B2 | 7/2006 | Soreq et al. |
| 7,456,154 | B2 | 11/2008 | Soreq et al. |
| 2003/0216344 | A1 | 11/2003 | Soreq et al. |

FOREIGN PATENT DOCUMENTS

| | | |
|---|---|---|
| WO | 98/26062 | 6/1998 |
| WO | 99/08672 A1 | 2/1999 |
| WO | 03/002739 A1 | 1/2003 |
| WO | 2007116395 A2 | 10/2007 |

OTHER PUBLICATIONS

Brenner et al., "The role of readthrough acetylcholinesterase in the pathophysiology of myasthenia gravis" The FASEB Journal, 17:214-222 (2003).
Beeri, R. et al. "Transgenic Expression of Human Acetylcholinesterase Induces Progressive Cognitive Deterioration in Mice," Curr. Biol. 5: 1063-1071 (1995).
Ben, Aziz-Aloya R. et al. "Expression of a Human Acetylcholinesterase Promoter-Reporter Construct in Developing Neuromuscular Junctions of Xenopus Embryos," Proc. Nat:1. Acad. Sci. U.S.A. 90: 2471-2475 {1993).
Chan, R. et al. Increased Expression of Acetylcholinestrase T and R Transcripts During Hematopoietic Differentiation is Accompanied by Parallel Elevations in the Levels of Their Respective Molecular Forms, J. Biol. Chem. 273: 9727-9733 (1998).
Chiu, et al. The Eight-year Experience of Plasmapheresis in Patients with Neurological Diseases. International Journal of Hematology, Supplement II, p. 81 (2002).
Cohen, O. et al. "Neuronal Overexpression of Readthrough" Acetylcholinesterase is Associated With Antisense-suppressible Behavioral Impairments, Mol . Psychiatry 7: 874-885 (2002).
Cohen, O. et al. "Endotoxin-Induced Changes in Human Working and Declarative Memory Associate With Cleavage of Plasma Readthrough" Acetylcholinesterase, J. Mol. Neurosci. 21: 195-208 (2003).
Ellman, G. et al. "A New and Rapid Colorimetric 7 petermination of Acetylcholinesterase Activity," Biochem. Pharmacol. 7: 88-95 (1961).
Erb, C et al. "Compensatory Mechanisms Enhance Hippocampal Acetylcholine Release in Transgenic Mice Expressing Human Acetylcholinesterase" J. Neurochem. 77: 638-646 (2001).
Galyam, N. et al. "Complex Host Cell Responses to Antisense Suppression of ACHE Gene Expression", Antisense and Nucleic Acid Drug Dev. 11: 51-57 (Abstract) (2001).
Grisaru, D. et al. "Human Osteogenesis Involves Differentiation-Dependent Increases in The Morphogenically Active 3' Alternative Splicing variant of Acetylcholinesterase," Mol. Cell. Biol. 19: 788-795 (1999).
Grisaru, D. et al. "ARP1 A Peptide Derived From the Stress-Associated Acetylcholinesterase Variant, Has Hematopoietic Growth Promoting Activities" Mol. Med. 7:93-105 (2001).
Kaufer, D. et al. "Acute Stress Facilitates LongLasting Changes in Cholinergic Gene Expression", Nature 393: 373-377 (1998).
Lesnik, E. et al. (1998) What Affects the Effects of 2'—Alkoxy Modifications? 1. Stabilization Effect of 2'—Methoxy Substitutions in Uniformly Modified DNA Oligonucleotides,• Biochemistry 37: 6991-6997 (1998).
Meshorer, E. et al. (2002) "Alternative Splicing and Neuritic mRNA Translocation Under Long-Term Neuronal Hypersensitivity," Science 295: 508-512 (2002).
Nijholt, I. et al. "Stress-Induced Alternative Splicing of Acetycholinesterase Results in Enhanced Fear Memory and Long-term Potentiation," Molecular Psychiatry 9: 174-183 (2004).
Shapira, M. et al. "A Transcription-Activating Polymorphism in The ACHE Promoter Associated With Acute Sensitivity to Anti-Acetycholinesterases," Hum. Mol. Genec. 9: 1273-1281 (2000).
Shohami, E. et al. "Antisense Prevention of Neuronal Damages Following Head Injury in Mice", J. Mol. Med. 78: 228-236 (2000).
Soreq, H. et al. Acetycholinesterase—New Roles for an Old Actor,• Nat. Rev. Neurosci. 2: 294-302 (2001).

(Continued)

*Primary Examiner* — Jennifer Pitrak McDonald
(74) *Attorney, Agent, or Firm* — Browdy and Neimark, PLLC

(57) ABSTRACT

AChE antisense oligonucleotides are used as antiinflammatory agents, such oligonucleotides preferably having the sequence of SEQ ID NO:1 and SEQ ID NO:7. Methods of treatment of inflammatory conditions, as well as fever, and particularly inflammation of the gastrointestinal tract, are described.

10 Claims, 20 Drawing Sheets

(56) References Cited

OTHER PUBLICATIONS

Soreq, H. et al. "Molecular Cloning and Construction of the Coding Region for Human Acetycholinesterase Reveals a G+C—Rich Attenuating Structure," Proc. Natl. Acad. Sci. 87: 9688-9692 (1990).
Sternfeld, M. et al. "Excess 'Read-through' Acetycholinesterase Attenuates But the 'Synaptic' Variant Intensifies Neurodeterioration Correlates," Proc. Natl. Acad. Sci. 97: 8647-8652 (2000).
Tomkins, O. et al. "Frequent Blood-Brain Barrier Disruption in the Human Cerebral Cortex," Cell. Mol. Neurobiol. 21: 675-691 (2001).
Zakut, H. et al. "Modified Properties of Serum Cholinesterases in Primary Carcinomas," Cancer 61: 727-737 (1988).
Soreq et al. "Anti-sense approach to anticholinesterase therapeutics," Israel Med. Assoc. J. 2:81-85 (2002).
Crooke in Antisense Drug Technology, Ch. 1, Basic Principles of Antisense Technology, pp. 1-28 (Springer-Verlag) (2001).
Gerwitz et al. "Nucleic Acid Therapeutics: State of the art and future prospects," Blood 92(3): 712-736{1998).
Jen et al. "Suppression of gene expression by targeted disruption of messenger RNA: available options and current strategies," Stem Cells 18: 307-319 (2000).
Opalinska et al. "Nucleic-acid therapeutics: basic principles and recent applications," Nat:. Rev. Drug. Discov. 1: 503-514 (2002).
Link et al. "Transforming growth factor-131 suppresses autoantigen-induced expression of proinflammatory cytokines but not of interleukin-10 in multiple sclerosis and myasthenia gravis" J. Neuroimrnunology 58: 21-35 (1995).
Martino et al. "cytokines and immunity in multiple sclerosis: the dual signal hypothesis," J. Neuroimrnunology 109:3-9 (2000).
Mocchegiani et al. (2000) "Different age-related effects of thymectomy in myasthenia gravis: role of thymoma, zinc, thymulin, IL-2 and IL-6," Mechanisms of Ageing and Development: 117: 79-91 (2000).
Aarli "Role of cytokines in neurological disorders," Curr. Med. Chem. 10: 1931-1937 (2003).
Giacobini "Cholinesterase inhibitors stabilize Alzheimer disease," Neurochemical Res. 25: 1185-1190 (2000).
Licastro et al. "Increased plasma levels of interleukin-1, interleukin-6 and alpha-1-antichymotrypsin in patients with Alzheimer's disease: peripheral inflammation or signals from the brain?," J. Neuroimrnunology 103: 97-102 (2000).
Lev-Lehman et al. "Antisense inhibition of Acetylcholinesterase gene expression causes transient hematopoietic alterations in vivo, " Gene Therapy 1: 127-1356 (1994).
Janus et al. "Transgenic mouse models of Alzheimer's disease," Physiology & Behavior 73: 873-886 (2001).
Hauser et al. "Cytokine accumulations in CSF of Multiple Sclerosis patients," Neurology 40:1735 (1990).
Meshorer et al., Advances in Behavioral Biology, vol. 51, pp. 45-48; (2000).
Wang et al. Nature, vol. 421, pp. 384-388; (2003).
European Supplementary Search Report issued Sep. 13, 2010 for European Patent Application No. 04791840.4.
Prough D. S. et al., "Efficacy of Oral Nifedipine in the Treatment of Reflex Sympathetic Dystrophy," Anesthesiology 62(6):796-799 (1985).
Mamczarz Jacek et al, Blockade by Nifedipine of Repeated Restraint Stress-Induced Delayed Hyperactivity in Rats,• Polish Journal of Pharmacology, 49(6):485-488 (Abstract Only); (1997).
Hubatsch Douglas, A. et al, Mechanical Stimulation Increases Expression of Acetylcholinesterase in Cultured Myotubes, American Journal of Physiology, 273(6)(1):C2002-C2009 (1997).
Luo Zhigang, et al. Regulation of Acetylcholinesterase mRNA stability by Calcium During Differentiation from Myoblasts to Myotubes, Journal of Biological Chemistry, vol. 269, No. 44, 1994, pp. 27216-27223.
Szreder Z. et al, "Inhibition of Pyrogen *Escherichia coli* Fever with Intracerebral Administration of Prazosin, Dihdrobenzperidol and Nifedipin in the Rabbits," General Pharmacology, vol. 22, No. 1:381-388 (1991).

Office Action issued Jan. 28, 2009 in connection with U.S. Appl. No. 11/788,321, filed Apr. 18, 2007.
Office Action issued Jun. 19, 2009 in connection with U.S. Appl. No. 11/788,321, filed Apr. 18, 2007.
Office Action issued Oct. 28, 2009 in connection with U.S. Appl. No. 11/788,321, filed Apr. 18, 2007.
Final Office Action issued Apr. 8, 2010 in connection with U.S. Appl. No. 11/788,321, filed Apr. 18, 2007.
Final Office Action issued Sep. 16, 2011 in Connection with U.S. Appl. No. 11/788,321, filed Apr. 18, 2007.
McCaffrey, R. J. and Lynch, J. K. "A Methodological Review of 'Method Skeptic' Reports" Neuropsychol. Rev. 3:235-48 (1992).
McGeer P. L. and McGeer E. G. "The inflammatory response system of brain: implications for therapy of Alzheimer and other neurodegenerative diseases" Brain Res. Rev. 21:195-218 (1995).
McKhann G. et al. "Acute Motor Axonal Neuropathy: A Frequent Cause of Acute Flaccid Paralysis in China" Ann. Neural. 33: 333-342 (1993).
Meyers C. A. "Mood and cognitive disorders in cancer patients receiving cytokine therapy" Adv. Exp. Med. Biol. 461:75-81 (1999).
Millard, C. B. and Broomfield, C. A. "Anticholinesterases : Medical Applications of Neurochemical Principles" J. Neurochem. 64, 1909-1918 (1995).
Mizuno, M. et al. "The Role of Neuropeptide Y in the Progesterone-Induced Luteinizing Hormone-Releasing Hormone Surge in Vivo in Ovariectomized Female Rhesus Monkeys" Endocrinology 141, 1772-1779 (2000).
Mullington J. et al. "Dose-dependent effects of endotoxin on human sleep" Am. J. Physiol. Regul. Integr. Comp. Physiol. 278:R947-55 (2000).
Murakami et al. "Genes: Structure and Regulation: Potent Inhibition of the Master Chondrogenic Factor Sox9 Gene by Interleukin-1 and Tumor Necrosis Factor" J. Biol. Chem. 275: 3687 (2000).
Navia, B. A. et al. "The AIDS Dementia Complex:l. Clinical Features"Ann. Neurol. 19:517-24 (1986).
Nishimura M. et al. "Characterization of Campylobacter jejuni isolates from patients with Guillain-Barre syndrome" J. Neurol. Sci. 153: 91-99 (1997).
Noga, B. R. et al. "Field Potential Mapping of Neurons in the Lumbar Spinal Cord Activated following Stimulation of the Mesencephalic Locomotor Region" J. Neurosci. 15, 2203-2217 (1995).
Oitzl M. S. et al. "Interleukin-lfl, but not interleukin-6, impairs spatial navigation learning" Brain Res. 613:160-3 (1993).
Palmer A. M. "Pharmacotherapy for Alzheimer's disease: progress and prospects" Trends Pharmacol. Sci. 23:426-33 (2002).
Perlmutter, S. I. et al. "Activity of Spinal Interneurons and Their Effects on Forearm Muscles During Voluntary Wrist Movements in the Monkey"J. Neurophysiol. 80, 2475-2494 (1998).
Perry, C. et al. "Complex regulation of acetylcholinesterase gene expression in human brain tumors" Oncogene 21:8428-8441 (2002).
Phelps, P. E. et al. "Embryonic Development of Four Different Subsets of Cholinergic Neurons in Rat Cervical Spinal Cord" J. Comp. Neural. 291, 9-26 (1990).
Pick et al. "From Brain to Blood: Alternative Splicing Evidence for the Cholinergic Basis of Mammalian Stress Responses" Annals NY Acad. Sci. 1018, 85-98 (2004).
Pollmacher T. et al. "Diurnal Variations in the Human Host Response to Endotoxin" J. Infect. Dis. 174:1040-5 (1996).
Prut, Y. and Fetz, E. E. "Primate spinal interneurons show pre-movement instructed delay activity" Nature 401, 590-594 (1999).
Pugh C. R. et al. "The immune system and memory consolidation: a role for the cytokine IL-1b" Brain Behau. Immun. 12:212-29 (1998).
Rachal Pugh C., et al. "Selective Effects of Peripheral Lipopolysaccharide Administration on Contextual and Auditory-Cue Fear Conditioning" Neurosci. Biobehav. Rev. 25:29-41 (2001).
Rees, J. et al. "Campylobacter Jejuni Infection and Guillain—Barré Syndrome"N. Eng. J. Med. 333: 1374-1379 (1995).
Reichenberg A. et al. "Cytokine-Associated Emotional and Cognitive Disturbances in Humans" Arch. Gen. Psychiatry 58:445-52 (2001).
Saida T. et al. "In Vivo Demyelinating Activity of Sera from Patients with Gdain-Barr6 Syndrome" Ann. Neurol. 11: 69-75 (1982).

(56) References Cited

OTHER PUBLICATIONS

Saida, T. et al. "Campylobacter jejuni Isolates from Japanese Patients with Guillain-Barre Syndrome" J. Infect. Dis. 176: Suppl. 2, S129-134 (1997).
Saito H. et al. "Animal models of vascular dementia hypertensive rats with emphasis on stroke-prone spontaneously" Brain. Exp. Pharmacol. Physiol. Suppl. 22:S257-9 (1995).
Sazani, P. et al. "Systemically Delivered Antisense Oligmers Upregulate Gene Expression in Mouse Tissue" Nat. Biotechnol. 20: 1228-1233 (2002).
Segal M. and Auerbach J. M. "Muscarinic Receptors Involved in Hippocampal Plasticity" Life Sci. 60:1085-91 (1997).
Sendtner, M. "Molecular mechanisms in spinal muscular atrophy: models and Perspectives" Curr. Opin. Neurol. 14: 629-634 (2001).
Seneviratne, "Guillain-Barré syndrome" U. Postgrad. Med. 76: 774-782 (2000).
Shaw K. N. et al. "Lipopolysaccharide causes deficits in spatial learning in the watermaze but not in BDNF expression in the rat dentate gyrus" Behav. Brain Res. 124:47-54 (2001).
Shaw, P.J. and Eggett, C. J. "Molecular factors underlying selective vulnerability of motor neurons to neurodegeneration in amyotrophic lateral sclerosis" J. Neurol. 247 Suppl 1: 117-27 (2000).
Sheikh, K. et al. "Molecular Mimicry in Guillain-Barré Syndrome", Ann. N.Y. Acad. Sci. 845: 307-321 (1998).
Sherriff, F. E. and Henderson, Z. "A cholinergic propriospinal innervation of the rat spinal cord" Brain Res. 634, 150-154 (1994).
Soreq H. and Glick D.: Novel roles for cholinesterases in stress and inhibitor responses. In: Giacobini E. (ed.) Cholinesterases and Cholinesterase Inhibitors: Basic, Preclinical and Clinical Aspects. London, Martin Dunitz, pp. 47-61 (2000).
Subramony, S. H. et al. "Motor neuropathy associated with a facilitating myasthenic syndrome" muscle nerve 9, 64-68 (1986).
Suzuki and Choi, "Repair and reconstruction of the cortical plate following closed cryogenic injury to the neonatal rat cerebrum" Acta. Neuropathol. (Berl) 82: 93-101 (1991).
Svensson, I. et al. "Soman-Induced Interleukin-1b mRNA and Protein in Rat Brain" Neurotoxicology 22, 355-362 (2001).
Tanaka et al. "A Zinc Finger Transcription Factor, αA-Crystallin Binding Protein 1, Is a Negative Regulator of the Chondrocyte-Specific Enhancer of the α1(II) Collagen Gene" Mol. Cell. Biol. 20: 4428 (2000).
Tavitian, B. et al. "In Vivo Imagining of Oligonucleotides with Positron Emission Tomography" Nat. Med. 4, 467-471 (1998).
Thornton, A. E. et al. "Memory in multiple sclerosis: Contextual Encoding deficits " J. Int. Neuropsychol. Soc. 8:395-409 (2002).
Tracey K. et al. "Mind over immunity" Faseb. J. 15: 1575-1576 (2001).
Tracey, K. J. "The inflammatory reflex" Nature 420, 853-859 (2002).
Trembovler V. et al. "Antioxidants Attenuate Acute Toxicity of Tumor Necrosis Factor-a Induced by Brain Injury in Rat "J. Interferon Cytokine Res. 19:791-5 (1999).
Usdin, T. B. et al. "Molecular Biology of the Vesicular Ach Transporter" Trends Neurosci. 18, 218-224 (1995).
Wang, C. X. et al. "Increase of interleukin-1b mRNA and protein in the spinal cord following experimental traumatic injury in the rat" Brain Res 759, 190-196 (1997).
Weihe, E. et al. "Visualization of the vesicular acetylcholine transporter in cholinergic nerve terminals and its targeting to a specific population of small synaptic vesicles" Proc. Natl. Acad. Sci. USA. 93, 3547-3552 (1996).
Weinstock M. "The Pharmacotherapy of Alzheimer's Disease Based on the Cholinergic Hypothesis: an Update" Neurodegeneration 4:349-56 (1995).
Willard L. B. et al. "pathological and biochemical consequences of acute and chronic neuroinflammation within the basal forebrain cholinergic system of rats" Neuroscience 88:193-200 (1999).
Yirmiya R. "Behavioral and psychological effects of immune activation: implications for 'depression due to a general medical condition'" Current Opinion in Psychiatry, 10: 470-476 (1997).
Apte, R.N., et al. "Differential Stimulation of Mononuclear Phagocyte IL 1 Production and Oxidative Burst by Tumor-Promoting and Non-Tumor-Promoting Agents" Immunobiology 175: 470-481 (1987).
Arendt, T. "Alzheimer's disease as a disorder of mechanisms underlying Structural brain self-organization." Neuroscience 102:723-65 (2001).
Asbury, et al "Assessment of Current Diagnostic Criteria for Guillain-Barr6 Syndrome" Ann. Neurol. 27: Suppl. S21-24 (1990).
Baddeley A. "Working Memory" Science 255:556-9 (1992).
Barber, R. P., et al. "The Morphology and Distribution of Neurons Containing Choline Acetyltransferase in the Adult Rat Spinal Cord: An Immunocytochemical Study" J. Comp. Neurol. 229, 329-346 (1984).
Becker, C. M. et al. "Isoform-Selective Deficit of Glycine Receptors in the Mouse Mutant spastic" Neuron 8, 283-289 (1992).
Beeri R. et al. "Enhanced Hemicholinium Binding and Attenuated Dendrite Branching in Cognitively Impaired Acetylcholinesteraser-Trangenic Mice." J. Neurochem. 69:2441-51 (1997).
Bemik, T. et al. "Pharmacological Stimulation of the Cholinergic Antiinflammatory Pathway" J. Exp. Med. 195: 781-788 (2002).
Bennett, C. F. "Efficiency of Antisense Oligonucleotide Drug Discovery" Antisense Nucleic Acid Drug Dev. 12: 215-224 (2002).
Bi et al. "Sox9 is required for cartilage formation", Nat. Genet. 22: 85 (1999).
Borovikova L. et al. "Vagus nerve stimulation attenuates the systemic in⁻ammatory response to endotoxin" Nature 405: 458-462 (2000).
Braasch, D. A. and Corey, D. R. "Novel Antisense and Peptide Nucleic Acid Strategies for Controlling Gene Expression" Biochemistry 41: 4503-4510 (2002).
Brown and Feasby "Conduction Block and Denervation in Guillain-Barre Polyneuropathy" Brain 107: (Pt. 1) 219-239 (1984).
Burrell R. Circ. "Human Responses to Bacterial Endotoxin" Shock 43:137-53 (1994).
Capuron L. et al. "Timing and Specificity of the Cognitive Changes Induced by Interleukin-2 and Interferon-a Treatments in Cancer Patients" Psychosom. Med. 63:376-86 (2001).
Capuron, L. et al. "Attentional and mnemonic deficits associated with infectious disease in Humans" Psychol. Med. 29:291-7 (1999).
Cifuentes-Diaz, C. et al. "Deletion of Murine SMN Exon 7 Directed to Skeletal Muscle Leads to Severe Muscular Dystrophy" J. Cell Biol. 152: 1107-1114 (2001).
de Quervain, D. J. et al. "Acute cortisone administration impairs retrieval of long-term declarative memory in humans" Nat. Neurosci. 3:313-4 (2000).
Dori A. et al. "Functional Manipulations of Acetylcholinesterase Splice Variants Highlight Alternative Splicing Contributions to Murine Neocortical Development" Cereb Cortex 15(4): 419-30 (2005).
Dyer, S. M. et al. "Peripheral cholinesterase inhibition by occupational chlorpyrifos exposure in Australian termiticide applicators" Toxicology 169, 177-185 (2001).
Erickson, J. D. et al. "The VAChTKhAT "cholinergic gene locus": new aspects of genetic and vesicular regulation of cholinergic function" Prog. Brain Res. 109, 69-82 (1996).
Fahmi H. and Chaby R. "Differential Recovery of Macrophages From Endotoxin-Tolerant States Elicited by Lipopolysaccharide and Enzymatic Treatments." Immunol. Invest. 23:243-58 (1994).
Furey M. L. et al. "Cholinergic Enhancement and Increased Selectivity of Perceptual Processing During Working Memory" Science 290:2315-9 (2000).
Ben et al. "*Homo sapiens* acetylcholinesterase (ACHE), transcript variant E4-E6, mRNA" GeneBank Accession No. NM 000665, nucleotide positions 733-752 (2013).
Geary, R. S. et al. "Pharmacokinetic Properties of 29—O—(2—Methoxyethyl)—Modified Oligonucleotide Analogs in Rats" J. Pharmacol. Exp. Ther. 296: 890-7 (2001).
Gibertini M. "III beta impairs relational but not procedural rodent learning in a water maze task" Adv. Exp. Med. Biol. 402:207-17 (1996).
Goodman J. C. et al. "Elevation of tumor necrosis factor in head injury" J. Neuroimmunol. 30:213-7 (1990).

(56) References Cited

OTHER PUBLICATIONS

Griffin J. et al. "Guillain-Barré syndrome in northern China The spectrum of neuropathological changes in clinically defined cases" Brain 118: (Pt. 3), 577-595 (1995).

Grifman and Soreq, "Differentiation Intensifies the Susceptibility of Pheochromocytoma Cells to Antisense Oligodeoxynucleotide-Dependent Suppression of Acetylcholinesterase Activity" Antisense Nucleic Acid Drug Dev. 7 (4):351-9 (1997).

The Italian Guillain-Barré Study Group "The prognosis and main prognostic indicators of Guillain-Barre syndrome A multicentre prospective study of 297 patients" Brain 119: (Pt. 6) 2053-2061 (1996).

Harrison B. et al. "Demyelination Induced by Serum from Patients with Gdain-Barr6 Syndrome"Ann. Neurol. 15: 163-170 (1984).

Harvey G. et al. "Failure of Anti-Gm, Igg or Igm to Induce Conduction Block Following Intraneural Transfer" Muscle Nerve 18: 388-394 (1995).

Hauss-Wegrzyniak B. et al. "LPS-induced neuroinflammatory effects do not recover with time" Neuroreport 11:1759-63 (2000).

Heeschen et al. "A novel angiogenic pathway mediated by non-neuronal nicotinic acetylcholine receptors" J. Clin. Invest. 110:527-36 (2002).

Hollander et al. "Increased Damage to Type 11 Collagen in Osteoarthritic Articular Cartilage Detected by a New Immunoassay" J. Clin. Invest. 93: 1722 (1994).

Hollander et al. "Damage to Type 11 Collagen in Aging and Osteoarthritis Starts at the Articular Surface, Originates Around Chondrocytes, and Extends into the Cartilage with Progressive Degeneration" J. Clin. Invest. 96: 2859 (1995).

Honavar M. et al. "A Clinicopathological Study of the Guillain-barré Syndrome" Brain 114: (Pt. 3), 1245-1269 (1991).

Hund, E. "Neurological complications of sepsis: critical illness polyneuropathy and myopathy" J. Neurol. 248: 929-934 (2001).

Ifergane G. et al. "Induction of conduction block by Campylobacter jejuni lipopolysaccharides and focal neural insult" J. Neural. Sci. 213: 11-14 (2003).

Kasuya, E. et al. "Effects of an antisense oligodeoxynucleotide for neuropeptide Y mRNA on in vivo luteinizing hormone-releasing hormone release in ovariectomized female rhesus monkeys" Regul. Pept. 75-76, 319-325 (1998).

Kim J. J. and Diamond D. M. "The Stressed *Hippocampus* Synaptic Plasticity and Lost Memories" Nat. Rev. Neurosci. 3:453-62 (2002).

Krasowski, M. D. et al. "Natural Inhibitors of Cholinesterases: Implications for Adverse Drug Reactions" Can. J. Anaesth. 44, 525-534 (1997).

Kuwabara S. et al. "Axonal Involvement At The Common Entrapment Sites in Guillain-Barré Syndrome With Igg Anti-Gm1 Antibody", Muscle Nerve 22: 840-845 (1999).

Lai, M. W. et al. "Pesticide-like Poisoning from a Prescription Drug" N. Engl. J. Med. 353:3 (2005).

Lefebvre et al. "SOX9 Is a Potent Activator of the Chondrocyte-Specific Enhancer of the Proa1(II) Collagen Gene", Mol. Cell. Biol. 17: 2336 (1997).

Levin E. D. and Simon B. "Nicotinic acetylcholine involvement in cognitive function in animals" B. Psychopharmacology (Berl) 138:217-30 (1998).

Li et al. "Neuronal—Glial Interactions Mediated by Interleukin-1 Enhance Neuronal Acetylcholinesterase Activity and mRNA Expression" J. Neurosci. 20, 149-155 (2000).

Lupien et al. "Increased Cortisol Levels and Impaired Cognition in Human Aging: Implication for Depression and Dementia in Later Life" Rev. Neurosci. 10: 117-39 (1999).

Maes M. et al. "The effects of psychological stress on humans] increased production of pro-inflammatory cytokines and a th1-like response in stress-induced anxiety" Cytokine 10:313-8 (1998).

Maier S. F. and Watkins L. R. "Cytokines for Psychologists: Implications of Bidirectional Immune-to-Brain Communication for Understanding Behavior, Mood, and Cognition" Psychol. Rev. 105:83-107 (1998).

Yirmiya, R. et al. "Brain Interleukin-1 Is Involved in Spatial Memory and Passive Avoidance Conditioning" Neurobiology of Learning and Memory, 78: 379-389 (2002).

Yuki N. et al., "A Bacterium Lipopolysaccharide That Elicits Guillain-Barré Syndrome Has a GM1 Ganglioside-like Structure" J. Exp. Med. 178: 1771-1775 (1993).

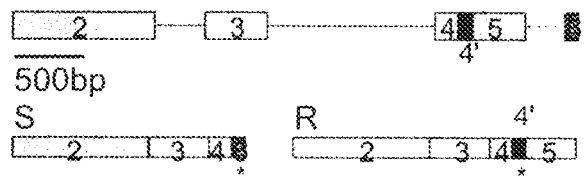
Fig. 2A
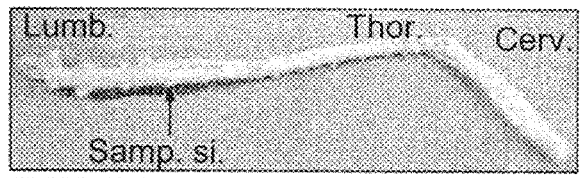
Fig. 2B
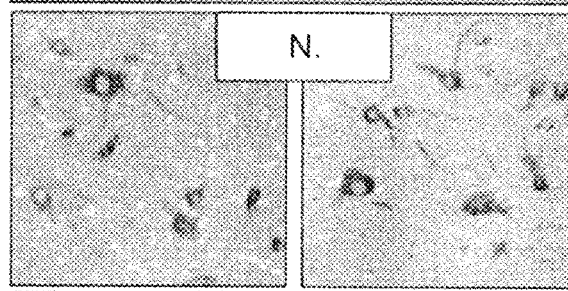
Fig. 2C  Fig. 2D
Fig. 2E  Fig. 2F
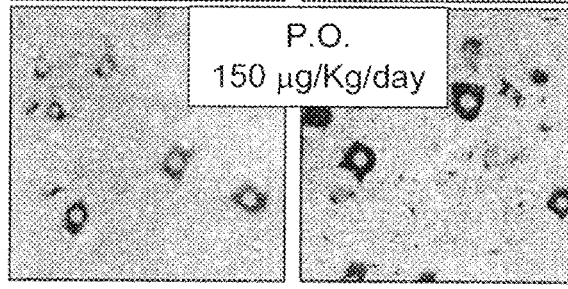
Fig. 2G  Fig. 2H
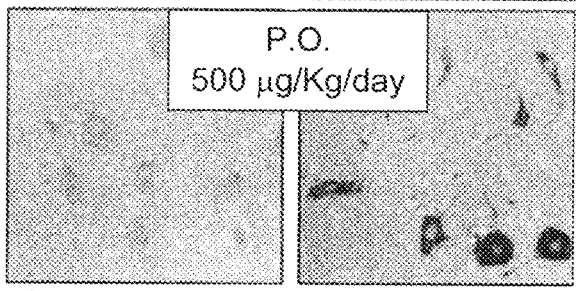
Fig. 2I  Fig. 2J
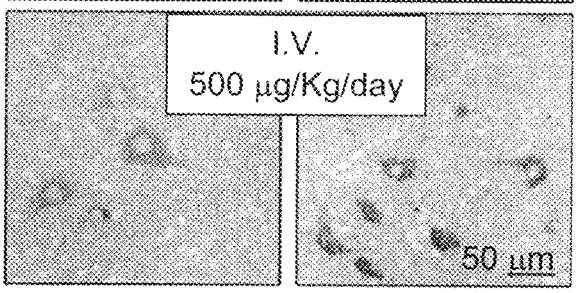
AChE-R mRNA    AChE-S mRNA

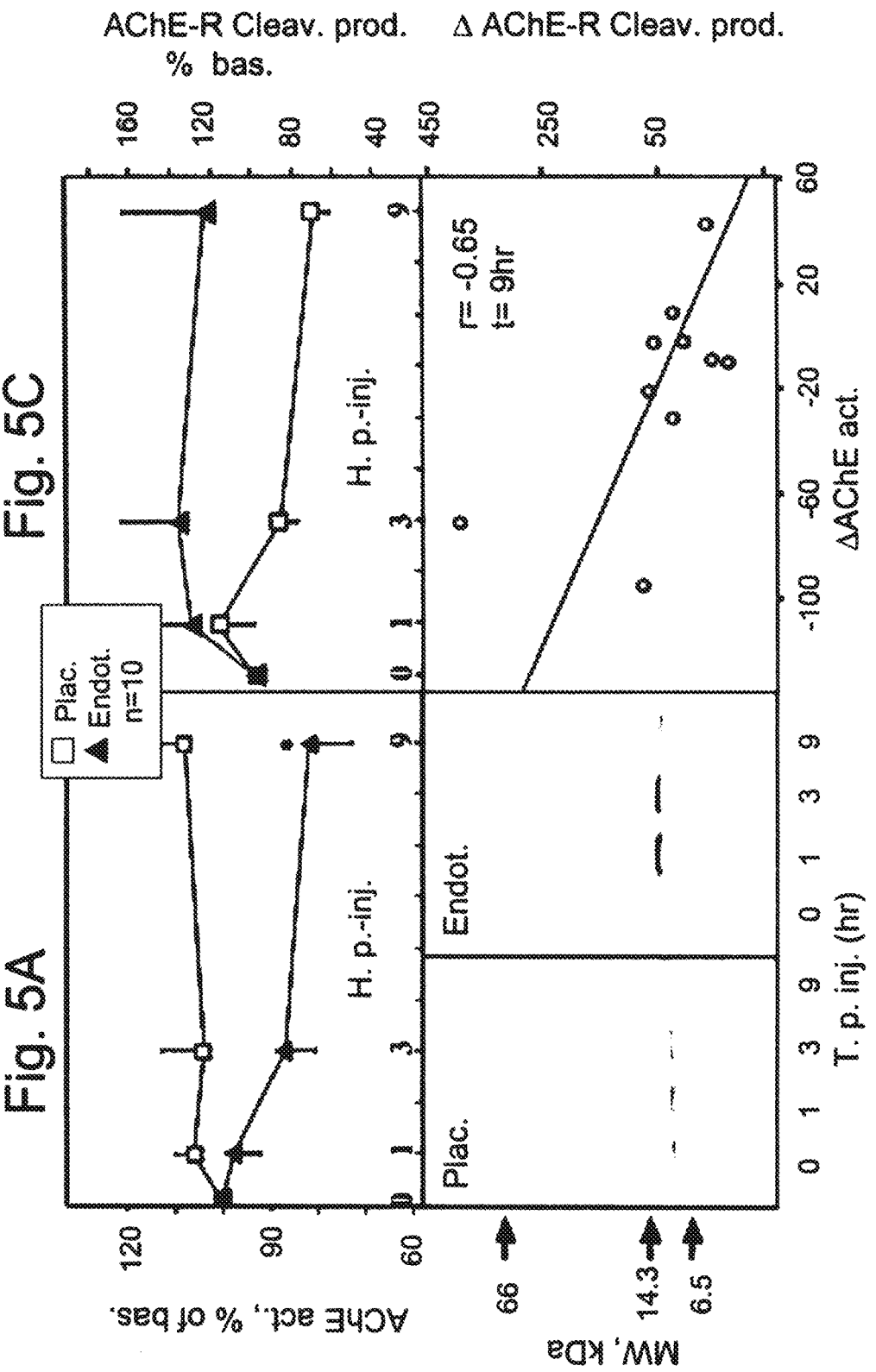

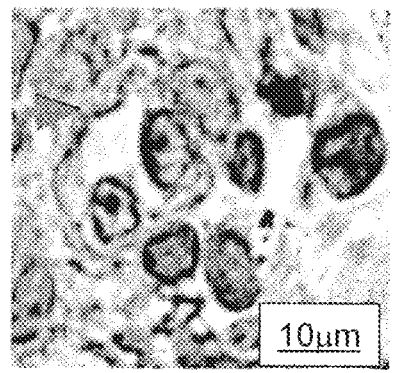
Fig. 7A　　　　　　　　　　Fig. 7B
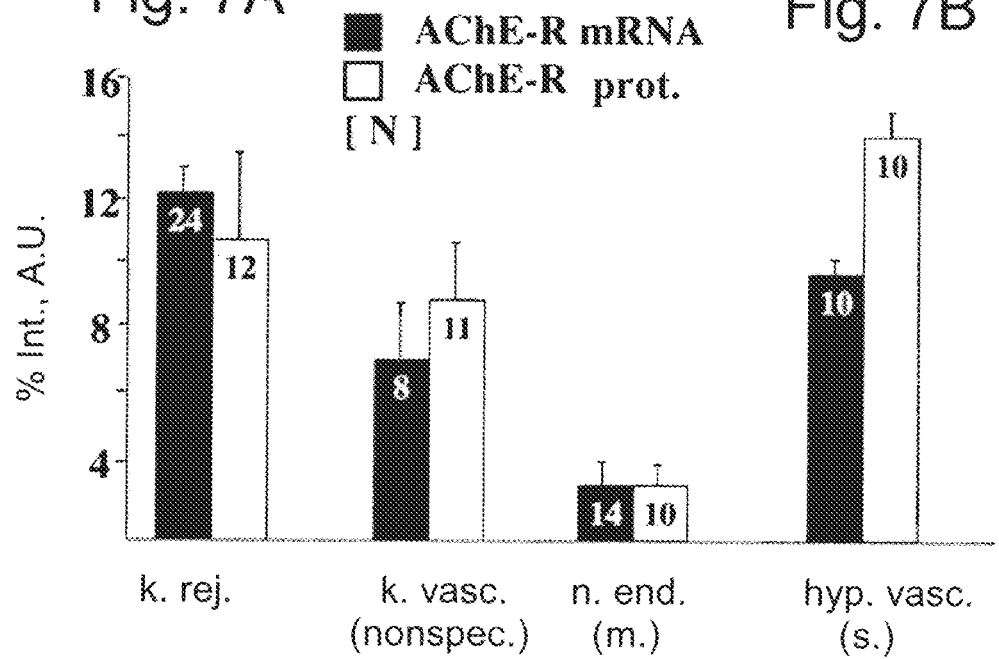
Fig. 7C

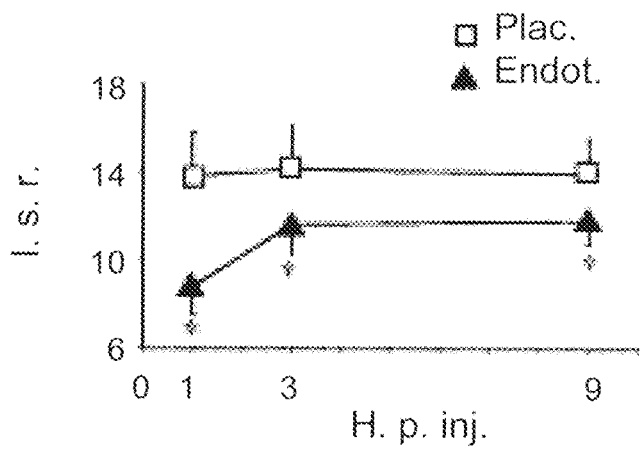
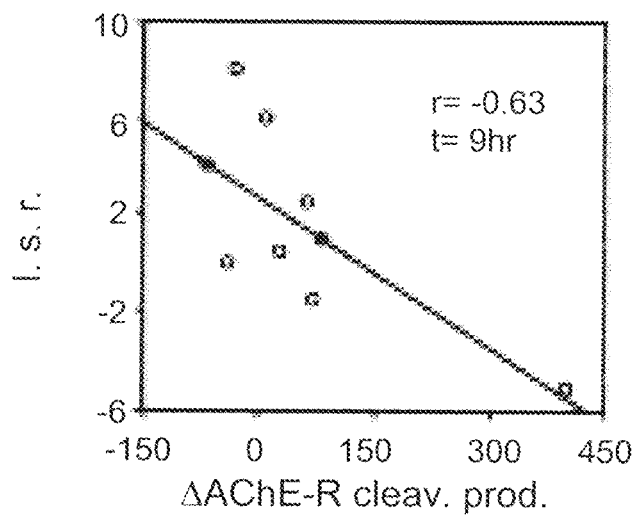
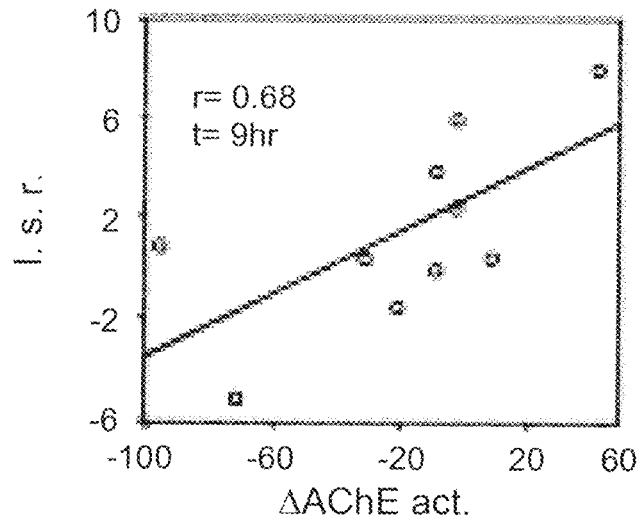

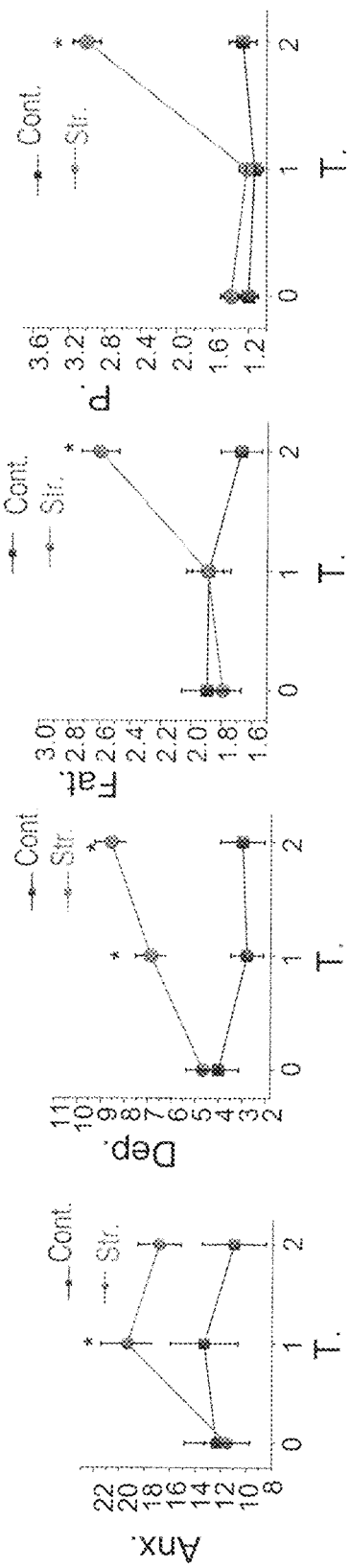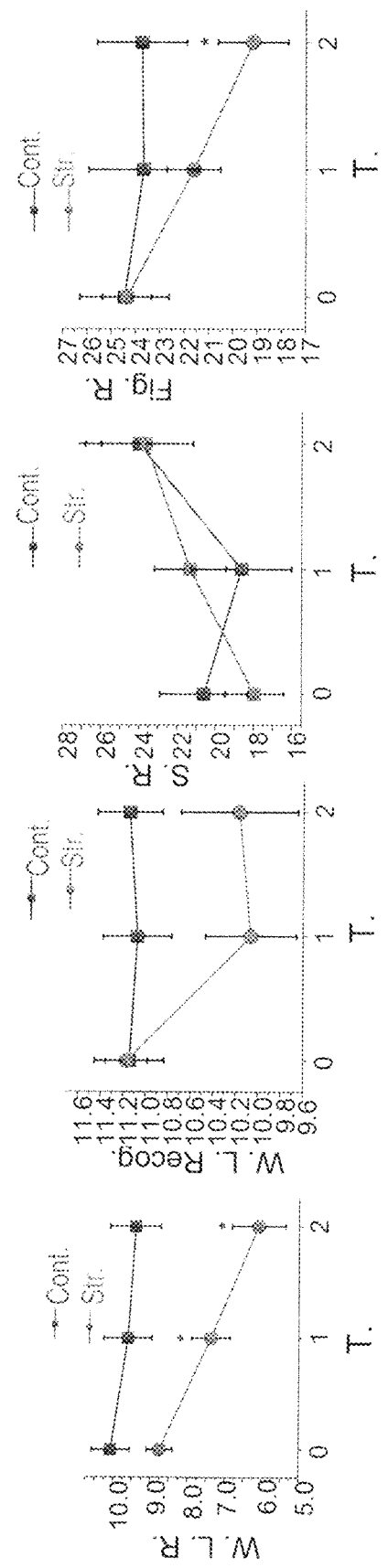

ANTISENSE OLIGONUCLEOTIDES AGAINST ACHE IN THE TREATMENT OF GASTROINTESTINAL INFLAMMATION DISORDERS

RELATED US APPLICATION DATA

This application is a continuation of application Ser. No. 13/835,267, which is a continuation-in-part of U.S. Ser. No. 13/351,171, filed Jan. 16, 2012, which is a continuation of U.S. Ser. No. 11/788,321, filed Apr. 18, 2007, now abandoned, which is a continuation of U.S. Ser. No. 11/187,719, filed Jul. 21, 2005, now abandoned, which is a continuation-in-part of PCT International Application No. PCT/IL2004/000978, filed Oct. 26, 2004, now expired, which claims priority of Israeli Application No. 158600, filed Oct. 26, 2003, the contents of each of which being hereby incorporated by reference into this application.

STATEMENT AS TO FEDERALLY SPONSORED RESEARCH

This work was supported by the US Army Medical Research and Material Command DAMD 17-99-1-9647 (July 1999-August 2004) and the Defense Advance Research Project Agency DARPA N66001-01-C-8015 (May 2001-May 2004). The US Government has certain rights in this invention.

FIELD OF THE INVENTION

Provided are antisense oligonucleotides targeted to the coding domain of the acetylcholinesterase (AChE) nucleotide sequence, as anti-inflammatory agents.

BACKGROUND OF THE INVENTION

All publications mentioned throughout this application are fully incorporated herein by reference, including all references cited therein.

Inflammation plays a crucial role in defense against pathogen invaders as well as in healing and recovery processes following various types of injury. However, the magnitude and duration of inflammatory responses have to be tightly regulated, because excessive inflammatory reactions can be detrimental, leading to autoimmune diseases, neurodegeneration, sepsis, trauma and other pathological conditions. It has long been recognized that regulation of inflammatory reactions is mediated both by immune responses (particularly the secretion of anti-inflammatory cytokines) and by neuroendocrine factors, particularly the activation of the pituitary-adrenal axis and the secretion of glucocorticoids. Recently it became evident that neural mechanisms are also involved in limiting inflammatory responses. In particular, it was found that cholinergic neurons inhibit acute inflammation, providing a rapid, localized, and adaptive anti-inflammatory reflex system (Tracy, 2002). In the periphery, acetylcholine (ACh) is mainly released by the efferent vagus nerve. It significantly attenuates the production of the pro-inflammatory cytokines TNFα, interleukin-1β (IL-1β), IL-6 and IL-18, but not the anti-inflammatory cytokine IL-10 [Tracey, K. J. (2002) Nature 420, 853-859]. Reciprocally, IL-1 causes AChE over-production both in PC12 cells and in the rat cortex [Li, Y. et al. (2000) J. Neurosci. 20, 149-155], suggesting a closed loop whereby ACh suppresses IL-1, ablating the induction of AChE production.

Within the mammalian spinal cord, several subsets of interneurons function in concert to translate converging cortical inputs into synchronized motoneuron activities [Noga, B. R. et al. (1995) J. Neurosci. 15, 2203-2217; Phelps, P. E. et al. (1990) J. Comp. Neural. 291, 9-26; Sherriff, F. E. and Henderson, Z. (1994) Brain Res. 634, 150-154; Perlmutter, S. I. et al. (1998) J. Neurophysiol. 80, 2475-2494; Prut, Y. and Fetz, E. E. (1999) Nature 401, 590-594]. Allostatic breakdown of this intricately controlled pathway may occur under various stressors, including glycinergic (strychnine) or cholinergic agents (succinylcholine), or under myasthenic crisis or post-anesthesia effects [Becker, C. M. et al. (1992) Neuron 8, 283-289; Millard, C. B. and Broomfield, C. A. (1995) J. Neurochem. 64, 1909-1918; Subramony, S. H. et al. (1986) Muscle Nerve 9, 64-68; Krasowski, M. D. et al. (1997) Can. J. Anaesth. 44, 525-534]. These and other acute stressors may induce massive tremor and spastic paralysis, reflecting failure of the quality control processes which presumably act to sustain cholinergic homeostasis in spinal cord motoneurons. In addition to these modulations in cholinergic neurotransmission, both injury and chemical stressors as well as organophosphate inhibitors of acetylcholinesterase (AChE) induce up-regulation of pro-inflammatory cytokines in the spinal cord (e.g. IL-1β following experimental spinal injury) [Wang, C. X. et al. (1997) Brain Res 759, 190-196; Svensson, I. et al. (2001) Neurotoxicology 22, 355-362; Dyer, S. M. et al. (2001) Toxicology 169, 177-185]. The cholinergic control over peripheral release of pro-inflammatory cytokines [Bernik, T. R. et al. (2002) J. Exp. Med. 195, 781-788; Borovikova, L. V. et al. (2000) Nature 405, 458-462; Tracey, K. J. et al. (2001) Faseb J. 15, 1575-1576] thus provoked the question whether cholinergic allostasis serves to control pro-inflammatory responses also in central nervous system (CNS) neurons.

Because spinal cord motoneurons respond to ACh, the presumed quality control process should exert regulatory effects upon cholinergic neurotransmission. As it needs to function rapidly, it likely involves short-lived molecules. Furthermore, in order to be broad-ranged, the proposed mechanism is likely to be induced under widely diverse stressors. The normally rare, stress-induced acetylcholinesterase variant AChE-R meets all of the requirements from an inducer of such response(s). AChE-R is overproduced under psychological, chemical and physical stresses [reviewed by Soreq, H. and Seidman, S. (2001) Nat. Rev. Neurosci. 2, 294-302]. A parallel stress response involves down-regulation of choline acetyltransferase (ChAT) [Kaufer, D. et al. (1998) Nature 393, 373-377] and the genomically linked vesicular acetylcholine transporter (VAChT) [Weihe, E. et al. (1996) Proc. Natl. Acad. Sci. USA. 93, 3547-3552], together limiting the production and vesicle packaging of acetylcholine while expediting its degradation. This yields down-regulation of the cholinergic hyperexcitation that is associated with many stresses. At a longer range, this stress response is associated with hypersensitivity to both agonists and antagonists of cholinergic neurotransmission [Meshorer, E. et al. (2002) Science 295, 508-512] and abnormal locomotor activities that can be ablated under antisense destruction of AChE-R mRNA [Cohen, O. et al. (2002) Mol. Psychiatry. 7, 874-885]. Finely-tuned control over AChE-R levels thus emerged as a key component of stress management by spinal cord motoneurons. AChE-R over-expression, which suppresses ACh levels, further lead to increased IL-1 production. Should this be the case, antisense suppression of AChE-R production [Brenner, T. et al. (2003) Faseb J. 17(2), 214-22] would increase ACh levels and reduce the levels of pro-inflammatory cytokines in CNS neurons.

In counterpart, parallel inflammatory responses and production of cytokines, particularly within the brain, has raised the suggestion that illness-associated alterations in memory functioning caused by medical conditions like Alzheimer's disease [Arendt, T. (2001) *Neuroscience* 102:723-65], multiple sclerosis [Thornton, A. E. et al. (2002) *J. Int. Neuropsychol. Soc.* 8:395-409], acquired immunodeficiency syndrome [Navia, B. A. et al. (1986) *Ann. Neurol.* 19:517-24] and infectious diseases [Capuron, L. et al. (1999) *Psychol. Med.* 29:291-7], are at least partly mediated by immune activation [Rachal Pugh C., et al. (2001) *Neurosci. Biobehav. Rev.* 25:29-41; Maier S. F. and Watkins L. R. (1998) *Psychol. Rev.* 105:83-107; Yirmiya R. (1997) *Current Opinion in Psychiatry*, 10: 470-476; Yirmiya, R. et al. (2002) *Neurobiology of Learning and Memory*, 78: 379-389]. Cytokine-induced memory impairments in humans, including cancer and hepatitis-C patients, as well as in experimental animals, support this notion [Capuron L. et al. (2001) *Psychosom. Med.* 63:376-86; Meyers C. A. (1999) *Adv. Exp. Med. Biol.* 461: 75-81; Gibertini M. (1996) *Adv. Exp. Med. Biol.* 402:207-17; Oitzl M. S. et al. (1993) *Brain Res.* 613:160-3]. Thus, like many other stressful stimuli, which are known to affect learning and memory processes [Kim J. J. and Diamond D. M. (2002) *Nat. Rev. Neurosci.* 3:453-62], inflammation can cause marked alterations in memory functioning. Administration of endotoxin (lipopolysaccharide), a complex glycolipid found in the outer membrane of all gram-negative bacteria, serves to assess the cognitive consequences of the acute host response to infection in humans. Endotoxin administration induces fever, malaise and increased production and secretion of cytokines, particularly TNF-α, IL-6, IL-1 and IL-1ra and cortisol [for review see Burrell R. (1994) *Circ. Shock* 43:137-53], as well as proteases [Fahmi H. and Chaby R. (1994) *Immunol. Invest.* 23:243-58]. In healthy humans, endotoxin-induced cytokine secretion is correlated with impairments in verbal and non-verbal declarative memory functions [Reichenberg A. et al. (2001) *Arch. Gen. Psychiatry* 58:445-52].

Memory deficits and profound neurobehavioral and neuroendocrine symptoms were also reported to be correlated with endotoxin-induced secretion of cytokines in experimental animals [Hauss-Wegrzyniak B. et al. (2000) *Neuroreport* 11:1759-63; Pugh C. R. et al. (1998) *Brain Behav. Immun.* 12:212-29; Shaw K. N. et al. (2001) *Behav. Brain Res.* 124: 47-54]. While these findings suggest that cytokines are involved in mediating the effects of endotoxin on memory, little is known about the neurotransmission pathways associated with these cytokine activities. The inventors initiated a search into the possibility that cholinergic processes are relevant to endotoxin responses because in the central nervous system (CNS), cholinergic responses are notably involved in several important aspects of cognitive functioning, including attention, learning and memory [for reviews see Levin E. D. and Simon B. B. (1998) *Psychopharmacology (Berl)* 138: 217-30; Segal M. and Auerbach J. M. (1997) *Life Sci.* 60:1085-91]. Moreover, endotoxin decreases brain choline acetyltransferase activity [Willard L. B. et al. (1999) *Neuroscience* 88:193-200], similar to the effects of psychological stress [Kaufer (1998) id ibid]. In the periphery, endogenous or exogenous acetylcholine (ACh) attenuates the release of pro-inflammatory cytokines from endotoxin-stimulated human macrophages [Borovikova (2000) id ibid.; Bemik (2002) id ibid.; Tracey (2001) id ibid]. The ACh hydrolyzing enzyme acetylcholinesterase (AChE) was considered as potentially being of particular relevance to these processes because AChE controls ACh levels and since AChE inhibitors improve cognitive functions in both clinical and experimental paradigms [Palmer A. M. (2002) *Trends Pharmacol. Sci.* 23:426-33; Weinstock M. (1995) *Neurodegeneration* 4:349-56]. Moreover, AChE over-expression is triggered by acute and chronic stressful insults [Meshorer (2002) id ibid.] and induces progressive memory impairments, as was demonstrated in transgenic mice [Beeri R. et al. (1995) *Curr. Biol.* 5:1063-71].

Moreover, mice that overexpress both AC and AChE-R present progressive dendritic and spine loss [Beeri R. et al. (1997) *J. Neurochem.* 69:2441-51], as well as altered anxiety responses [Erb C. et al. (2001) *J. Neurochem.* 77:638-46]. Furthermore, these mice display early-onset deficits in social recognition and exaggerated responsiveness to stressful insults. These can be briefly ameliorated by conventional anticholinesterase treatment or for longer periods by an antisense oligonucleotide capable of specifically inducing the destruction of AChE-R mRNA [Cohen (2002) id ibid.], suggesting that AChE-R is the primary cause. Thus, AChE-R production may lead to both positive and negative effects on cognition.

Stressful insults induce AChE-R production in the periphery as well (e.g., in the small intestines), and failure to induce this production, in response to aversive stimuli, results in hypersensitivity to relatively mild stressors [Shapira M. et al. (2000) *Hum. Mol. Genet.* 9:1273-1281]. This observation raised the possibility that peripheral AChE modulations may serve as a surrogate marker of endotoxin-induced changes in cognition as well. However, in plasma, proteolytic cleavage of AChE-R leads to the appearance in the serum of a short immunopositive C-terminal peptide which facilitates the hematopoietic stress responses [Grisaru, D. et al. (2001) *Mol. Med.* 7, 93-105]. Hence, the inventors investigated the effects of endotoxin administration on both AChE activity and AChE-R cleavage in healthy human volunteers and explored potential correlations between these parameters, the secretion of cytokines or cortisol, and changes with time in memory functions. In addition to declarative memory, which involves consciously accessible records of facts and events through concerted functioning of hippocampal and prefrontal structures [Kim and Diamond (2002) id ibid.], the inventors assessed the effects of endotoxin and its interactions with AChE cleavage on working memory, which involves temporary storage and manipulation of information necessary for cognitive functioning [Baddeley A. (1992) *Science* 255:556-9], and has been shown to involve prefrontal cholinergic mechanisms [Furey M. L. et al. (2000) *Science* 290:2315-9].

Peripheral neuropathies are caused by altered function and structure of peripheral motor, sensory or autonomic neurons. The main causes of neuropathy are entrapment (compression), diabetes and other systemic diseases, inherited disorders, inflammatory demyelinating, ischemic, metabolic, and paraneoplastic conditions, nutritional deficiency states, and toxin-induced derangement. One example of a peripheral neuropathy is the Guillain-Barre syndrome (GBS).

GBS is an acute inflammatory polyneuropathy. It is the most common cause of acute flaccid paralysis worldwide, with an annual incidence of 0.75 to 2 in 100,000 in the general population. GBS is suspected when a patient presents with progressive motor weakness and loss of deep tendon reflexes (areflexia). Other clinical features include sensory symptoms, cranial nerve involvement, autonomic dysfunction causing pulse and blood pressure changes, and respiratory failure, which is a major cause of morbidity and mortality [Asbury and Cornblath, (1990) *Ann. Neurol.* 27: Suppl. S21-24]. The onset of symptoms can either be acute or sub-acute, but improvement is gradual, initiating after a plateau phase of several weeks, reaching clinical recovery by 6-7 months

[Group, T.I.G. (1996) *Brain* 119: (Pt. 6) 2053-2061]. Ventilatory support due to respiratory muscle weakness is needed in about a quarter of the patients and mortality ranges up to 13 percent [Seneviratne, U. (2000) *Postgrad. Med.* 76: 774-782].

In about two thirds of patients, symptoms are preceded by an antecedent infection, commonly an upper respiratory tract infection (40%) or gastroenteritis (20%) occurring 4 weeks prior to onset of disease [Group (1996) id ibid.; Rees, J. et al. (1995) *N. Eng. J. Med.* 333: 1374-1379]. According to this, GBS is thought to result from abnormal immune responses triggered by certain infectious agents and directed towards the peripheral nerves [Seneviratne (2000) id ibid]. Interestingly, one recent report suggests that the clinical symptoms of drug poisoning by the AChE-inhibitor rivastigmine resemble those of GBS [Lai, M. W. et al. (2005) *N. Engl. J. Med.* 353:3].

The diagnosis of Guillain-Barre syndrome is based on clinical presentation, which is then supported by cerebrospinal fluid (C SF) analysis demonstrating elevated protein content and normal leukocyte cell count, indicating an inflammatory reaction. Electrophysiological studies then specify the clinico-pathological type according to evidence for damage of myelin, motor or sensory axons [Asbury and Cornblath (1990) id ibid.].

Segmental demyelination, termed acute inflammatory demyelinating polyradiculoneuropathy (AIDP) is the most common type of Guillain-Barre syndrome, apparently mediated by lymphocytic and macrophage infiltration of the peripheral nerves [Griffin J. et al. (1995) *Brain* 118: (Pt. 3), 577-595; Honavar M. et al. (1991) *Brain* 114: (Pt. 3), 1245-1269; Rees (1995) id ibid.]. Demyelination is demonstrated by electrophysiological reduction of nerve conduction velocity, and subsequent remyelination is associated with recovery. In contrast to this, only minimal demyelination but prominent Wallerian-like degeneration with peri-axonal macrophage infiltration are detected in axonal degeneration types of GBS, where motor axons exclusively or motor together with sensory axons, are damaged in acute motor axonal neuropathy (AMAN) [McKhann G. et al. (1993) *Ann. Neural.* 33: 333-342] and acute motor sensory axonal neuropathy (AMSAN) [Griffin (1995) id ibid.], respectively. Accordingly, the electrophysiological features in these cases are reduced compound muscle action potential (CMAP) amplitude, and additionally, reduced sensory nerve action potentials in AMSAN, but preserved conduction velocity, indicating axonal dysfunction without demyelination. Both axonal neuropathies are characterized by rapidly progressive weakness, often with respiratory failure, but although AMAN patients usually exhibit good recovery [McKhann (1993) id ibid.], the recovery of AMSAN patients is generally slow and incomplete, considered to be the most severe form of GBS (Brown and Feasby (1984) *Brain* 107: (Pt. 1) 219-239].

Axonal degeneration types of GBS are often preceded by infection with *Campylobacter jejuni* (Cj), which is associated with a slow recovery, and severe residual disability [Rees (1995) id ibid]. There are several serotypes of Cj, and the one most often isolated from GBS patients belongs to Penner serotype 19 (0:19) (Saida, T. et al. (1997) *J. Infect. Dis.* 176: Suppl. 2, S129-134]. The lipopolysaccharides (LPS) of Cj share ganglioside-like epitopes with ganglioside-surface molecules of peripheral nerves, and patients with GBS have anti-ganglioside antibodies, suggesting that "molecular mimicry" is the immunopathogenic mechanism of injury to the peripheral nerve fibers [Sheikh, K. et al., (1998) *Ann. N.Y. Acad. Sci.* 845: 307-321; Yuki N. et al., (1993) *J. Exp. Med.* 178: 1771-1775]. Nevertheless, although Cj-0:19 serotype is significantly associated with elevated anti-ganglioside antibody titers in the sera of the patients, no significant correlation was found between the presence of these antibodies and the clinical pattern of GBS [Nishimura M. et al. (1997) *J. Neurol. Sci.* 153: 91-99]. This therefore indicates that additional factors may determine the axonal damage or disfunction following the apparently antibody-mediated nerve-surface injury. In agreement with this, the currently accepted treatments of GBS is intravenous immunoglobulin administration or plasma exchange (plasmapheresis), which act through suppression or removal of auto-antibodies, both which have been found to be equally beneficial [Seneviratne (2000) id ibid]. Nevertheless, several authors reported a rapid resolution of nerve conduction blocks following plasmapheresis, which could not be explained by remyelination or axonal regeneration [Kuwabara S. et al., (1999) *Muscle Nerve* 22: 840-845; Suzuki and Choi, (1991) *Acta. Neuropathol. (Berl)* 82: 93-101]. This suggests a possible role for a humoral factor in the pathogenesis of the disease, causing physiological conduction abnormalities that may facilitate the destructive process.

Administration of LPS to humans is known to increase production and secretion of cytokines and cortisol [Burrell R. (1994) *Circ. Shock* 43: 137-153]. In addition to this, LPS decreases the activity of brain choline acetyltransferase [Willard L. et al. (1999) *Neuroscience* 88: 193-200], similar to the effects of psychological stress [Kaufer (1998) id ibid.], reducing production of acetylcholine (ACh). In the periphery, ACh attenuates the release of pro-inflammatory cytokines from LPS-stimulated human macrophages [Bemik, T. et al. (2002) *J. Exp. Med.* 195: 781-788; Borovikova L. et al. (2000) *Nature* 405: 458-462; Tracey K. et al. (2001) *Faseb. J.* 15: 1575-1576]. AChE is therefore considered as potentially being of particular relevance to these processes because AChE controls ACh levels. Acute and chronic stressful insults trigger transcriptional activation of AChE gene expression, which leads to accumulation of the normally rare, AChE-R splice variant [Soreq (2001) id ibid]. The AChE-R excess reduces the stress-induced cholinergic hyperexcitation in the CNS [Kaufer (1998) id ibid]. In the periphery (e.g., in the small intestines), failure to induce this production in response to aversive stimuli results in hypersensitivity to relatively mild stressors [Shapira (2000) id ibid]. In plasma, proteolytic cleavage of AChE-R leads to the appearance of its distinct short C-terminal peptide (AChE-R Peptide; ARP) which accumulates following *Salmonella*-LPS endotoxin administration to humans [Cohen O. et al. (2003) *J. Mol. Neurosci.* 21: 199-212], and facilitates the hematopoietic stress responses [Grisaru (2001) id ibid]. The inventors hence sought to examine the involvement of AChE-R and ARP in induction of functional conduction abnormalities in the sciatic nerve.

The role of cholinergic mechanisms in learning and memory, the involvement of AChE-R in stress responses, the suppression by ACh of pro-inflammatory cytokines production, the effects of endotoxin on memory functions, and the potential involvement of AChE-R in nerve conduction block, suggested involvement of AChE-R in inflammatory associated processes which could thus potentially be suppressed by an inhibitor of AChE-R expression.

The prospect of therapeutic agents of exquisite specificity and action at very low concentration has stimulated the development of antisense oligonucleotides (AS-ON) targeted against a variety of mRNAs. Major problems remain access to the RNA processing machinery of the cell, potential differences between specific cell types and the mode of chemical protection employed. When the cell of interest is within the CNS, the problem of access is compounded by the presence of the blood-brain barrier [Tavitian, B. et al. (1998) *Nat. Med.*

4, 467-471]. Nevertheless, some attempts have been successful even in primates [Kasuya, E. et al. (1998) Regul. Pept. 75-76, 319-325; Mizuno, M. et al. (2000) Endocrinology 141, 1772-1779]. The inventors have previously demonstrated antisense suppression of the stress-induced AChE-R mRNA, enabling retrieval of normal cellular and physiological functions following stress-induced changes in cultured rat and human cells [Galyam, N. et al. (2001) Antisense Nucleic Acid Drug Dev. 11, 51-57; Grisaru, D. et al. (2001) id ibid.] and in live mice [Cohen et al. (2002) id ibid.; Shohami, E. et al., (2000) J. Mol. Med. 78, 228-236] and rats [Brenner, T. et al., (2003) id ibid]. While the tested consequences in all of these studies were limited to direct measurement of the target protein and mRNA, the working hypothesis predicted additional, anti-inflammatory effects for antisense retrieval of cholinergic balance. Here, the inventors report the outcome of experiments aimed at addressing the stress-induced overproduction and selective AS-ON retrieval of normal AChE-R levels under injection stress in cynomolgus monkeys. The findings demonstrate differential susceptibility of specific neuron types to AS-ON responses, as well as concomitant suppression of IL-1β and IL-6 following the retrieval of cholinergic balance in spinal cord neurons. The present inventors have previously found that antisense oligonucleotides against the common coding region of AChE are useful for suppressing AChE-R production [see WO 98/26062]. In particular, the inventors have shown the use of an antisense oligonucleotide against the AChE sequence for the treatment of myasthenia gravis [WO 03/002739 and US 2003/0216344].

Various diseases are associated with chronic inflammation of the gastrointestinal tract. These diseases include inflammatory bowel diseases (e.g. ulcerative colitis and Crohn's disease), irritable bowel syndrome, ileitis, chronic inflammatory intestinal disease and celiac.

Inflammatory Bowel Disease (IBD) is a chronic, recurring-remitting immune response and inflammation of the gastrointestinal tract. The two most common conditions of IBD are ulcerative colitis (UC) and Crohn's disease. Currently, the annual incidence of IBD ranges from 1 to 10 cases per 100,000 and the prevalence ranges from 10 to 70 per 100,000 people.

Crohn's disease (also known as Crohn syndrome and regional enteritis), is a type of IBD that may affect any part of the gastrointestinal tract from mouth to anus, causing a wide variety of symptoms. It primarily causes abdominal pain, diarrhea (which may be bloody), vomiting or weight loss, but may also cause complications outside the gastrointestinal tract such as skin rashes, arthritis, inflammation of the eye, tiredness, and lack of concentration.

Ulcerative colitis is a lifelong illness that has a profound health-related, emotional and social impact on affected patients. Ulcerative colitis affects the lining of the large intestine (colon) and rectum and may affect any age group, although there are peaks at ages 15-30 and then again at ages 50-70. Similar to the case of Crohn's disease, the symptoms of ulcerative colitis include abdominal pain and cramping, blood in the stools, diarrhea, fever, rectal pain and weight loss.

Current treatment of IBD is aimed at reducing its symptoms, pushing patients into remission and maintaining them at that state. Treatment can be broadly divided into anti-inflammatory (e.g., sulfasalazine, 5-aminosalicylic acid), immunosuppressant (e.g., azathioprine, 6-mercaptopurine) and biological drugs (e.g. Remicade and Humira). Anti-inflammatory drugs are usually the first-line treatment. Corticosteroids or TNF blockers (e.g., infliximab, adalimumab, certolizumab) may be an alternative or additional treatment for patients with moderate to severe IBD who do not respond to the first-line treatment, in order to reduce inflammation. Unfortunately, however, all these treatments are associated with significant adverse effects. Therefore, there remains a significant unmet medical need for novel efficacious treatments with a favorable safety profile.

Based on the inventors' herein described results, the present invention provides a novel use for an antisense oligonucleotide directed against the AChE mRNA sequence, as a new anti-inflammatory agent, specifically for the treatment of subjects afflicted with gastrointestinal inflammatory disorders.

Other purposes and advantages of the invention will become apparent as the description proceeds.

SUMMARY OF THE INVENTION

Provided is a method for the treatment or prevention of inflammation of the gastrointestinal tract in a human subject in need thereof comprising administering to the subject a therapeutically effective amount of an inhibitor of AChE expression or a pharmaceutical composition comprising the same, said inhibitor of AChE expression being an antisense oligonucleotide having the nucleotide sequence as denoted by any one of SEQ ID NO:7 and SEQ ID NO:1.

The inflammation of the gastrointestinal tract can be Inflammatory Bowel Disease (IBD), for example Crohn's disease or ulcerative colitis.

The said antisense oligonucleotide or pharmaceutical composition comprising the same can be for daily use by the subject, and the therapeutically effective amount is a dose of said antisense oligonucleotide of between about 0.01 mg/Kg/day and about 10.0 mg/Kg/day. The said dose of said antisense oligonucleotide can be between about 0.1 mg/Kg/day and about 1.0 mg/Kg/day.

In embodiments of the method of the presently disclosed subject matter, the said antisense oligonucleotide or pharmaceutical composition comprising the same are administered orally, specifically at a dose of from about 10 mg/day to about 50 mg/day, for examples 10, 15, 20, 25, 30, 35, 40, 45 or 50 mg/day.

In the disclosed method of treatment, said antisense oligonucleotide is orally administered to a subject in need for at least 10 consecutive days, at identical or different daily doses. The said antisense oligonucleotide can be orally administered to a subject in need for at least 10 and up to 50 consecutive days, at the identical or different daily doses, for example up to 20, up to 30, up to 40 or up to 50 consecutive days. Daily doses may vary. If necessary, hEN101 can be administered for longer periods of time. Administration protocol is to be determined by the attending physician. Higher doses may be used during periods of acute condition.

The antisense oligonucleotide can be comprised in a pharmaceutical composition, which further optionally comprises at least one of pharmaceutically acceptable additives, carriers and diluents. A specific carrier can be saline.

Also provided is a method for treating and/or preventing an inflammatory condition in the gastrointestinal tract of a subject in need, comprising providing an antisense oligonucleotide directed against AChE, having the nucleotide sequence as denoted by any one of SEQ ID NO:1 and SEQ ID NO:7; providing a liquid carrier for mixing with said antisense oligonucleotide; mixing said antisense oligonucleotide with said carrier to form a liquid composition; and orally administering said liquid composition to said subject.

Further provided is a kit comprising at least one dose of a therapeutically effective amount of an antisense oligonucleotide having the nucleotide sequence as denoted by any one of SEQ ID NO:7 and SEQ ID NO:1; a liquid carrier for mixing with the antisense oligonucleotide of (a); means for mixing said antisense oligonucleotide of (a) with said carrier of (b) to form a liquid mixture for oral administration of said antisense oligonucleotide; instructions for use. In the disclosed kit, said liquid carrier can specifically be saline.

```
The antisense oligonucleotide having the sequence:
5'-CTGCCACGTTCTCCTGCACC-3' is denoted by SEQ ID

NO: 1).

The antisense oligonucleotide having the sequence:
5'-CTGCCACGTTCTCCTGCA*C*C*-3' is denoted by SEQ ID NO: 7. The three 3' terminal residues are modified with 2-O-methyl groups (*).
```

BRIEF DESCRIPTION OF THE FIGURES

FIG. 1A: Confocal microscopy projections of spinal cord motoneurons (cell diameter=40 μm), immunolabeled (white) with anti-VAChT antibody. The total volume and average number per cell of labeled terminals were measured using Image-Pro Plus software, and the result of each treatment (1, 2, 3 and 4) plotted in the graphs shown in FIGS. 1B and 1C.

FIG. 1B: Average value of volume and average number per cell of labeled terminals, including all motoneurons detected in a section.

FIG. 1C: Population distribution of volume and average number per cell of labeled terminals, including all motoneurons detected in a section.

FIG. 1D: Average values of FIGS. 1B, 1C analyses (plus or minus Standard Evaluation of the Mean, SEM). Significant reductions are marked by asterisks ($p<0.01$, Student's t test).

FIG. 1E: Immunolabeling with anti-ChAT antibody in partition cells from naive spinal cord, localized in close proximity to the central canal (arrows). Hematoxylin was used for background staining.

FIG. 1F: Higher magnification of ChAT positive partition cells in naive monkeys (1) or following oral (p.o.) administration of 150 μg/kg/day (2) or 500 μg/kg/day (3) and i.v. administration of 500 μg/kg/day hEN101 (4). Note dose-independent handling-induced reductions in both terminals volume and density.

Abbreviations:

n., naive; Term., terminal; vol., volume; Part. Ce., Partition cell; Cent. Can., Central canal.

FIG. 2A-2J: Selective AChE-R mRNA Suppression by hEN101 in Monkey Spinal Cord Neurons.

FIG. 2A: Scheme of the human ACHE gene coding exons and two of its alternative transcripts, the synaptic AChE-S(S) and the stress-associated AChE-R(R) mRNA. The S transcript includes exons 2, 3, 4 and 6, whereas the R transcript contains exons 2, 3, 4, 5 and pseudointron 4'. These distinctions served to prepare transcript-specific probes, indicated by an asterisk.

FIG. 2B: Sampling site on the dissected monkey lumbar spinal cord is indicated by an arrow.

FIG. 2C-2J: Tissue sections from lumbar spinal cords were prepared following 7-day treatment with the noted doses of hEN101 by p.o. or i.v. administration. Shown is in situ hybridization used to compare neuronal labeling pattern with the noted probes.

Nuclei were visualized by DAPI staining (white). There was no difference between tested sections in total cell numbers and/or general histology. Note that AChE-S mRNA labeling displayed significant changes following treatment only in neuronal process sections (2F, 2H and 2J as compared to 2D), whereas neuronal AChE-R mRNA labeling was notably reduced in cell bodies.

FIG. 2C: No treatment, staining specific for AChE-R mRNA.

FIG. 2D: No treatment, staining specific for AChE-S mRNA.

FIG. 2E: Treatment with 150 μg/kg/day of EN101, p.o., staining specific for AChE-R mRNA.

FIG. 2F: Treatment with 150 μg/kg/day of EN101, p.o., staining specific for AChE-S mRNA.

FIG. 2G: Treatment with 500 μg/kg/day of EN101, p.o., staining specific for AChE-R mRNA.

FIG. 2H: Treatment with 500 μg/kg/day of EN101, p.o., staining specific for AChE-S mRNA.

FIG. 2I: Treatment with 500 μg/kg/day of EN101, i.v., staining specific for AChE-R mRNA.

FIG. 2J: Treatment with 500 μg/kg/day of EN101, i.v., staining specific for AChE-S mRNA.

Figure 3A:
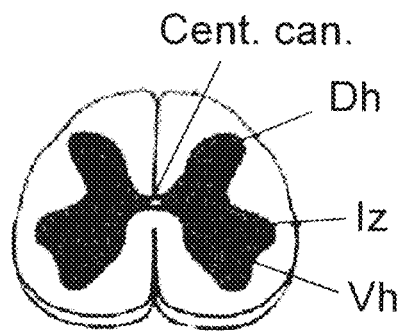
Figure 3B:
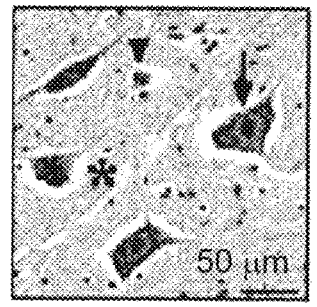
Figure 3C:
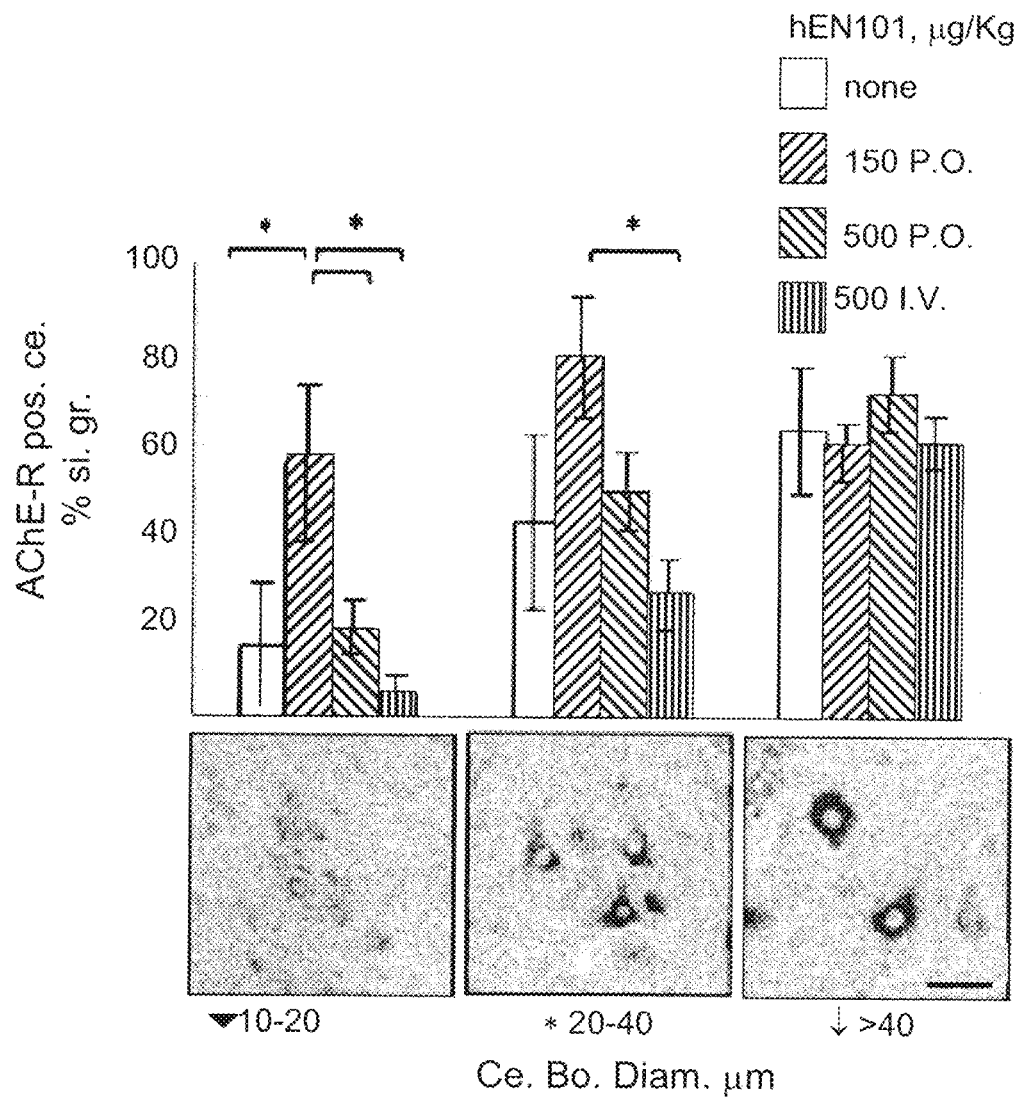

FIG. 3A-3C: Cell Size-Dependent Efficacy of Neuronal AChE-R mRNA Suppression.

FIG. 3A: Scheme of the lumbar spinal cord and its three compartments: the ventral and dorsal horns separated by the intermediate zone and the central canal.

FIG. 3B: Histological staining (Hematoxylin and eosin) of a representative field in the intermediate zone of the lumbar spinal cord. Three cells are marked according to their perikaryon diameters: 10-20 μm (arrowhead, the majority of those cells is located in the dorsal horn), 20-40 μm (asterisk) and =40 μm (arrow).

FIG. 3C: Shown are fractions of AChE-R positive neurons from the three size groups under the different treatment regimens. Insets: representative neurons from the different size groups, taken from the p.o. 150 μg/kg/day regimen. Columns show average AChE-R positive cells in each size group plus or minus SEM representing repeated analyses of the entire lumbar spinal cord gray matter in multiple sections. Stars note significant differences ($p<0.05$, Wilcoxon test).

Abbreviations:

Cent. Can., central canal; D. h., dorsal horn; I. z., Intermediate zone; V. h., ventral horn; pos. ce., positive cells; si. gr., size group; Ce. Bo. Diam., cell body diameter.

Figures 4A, 4B, 4C:
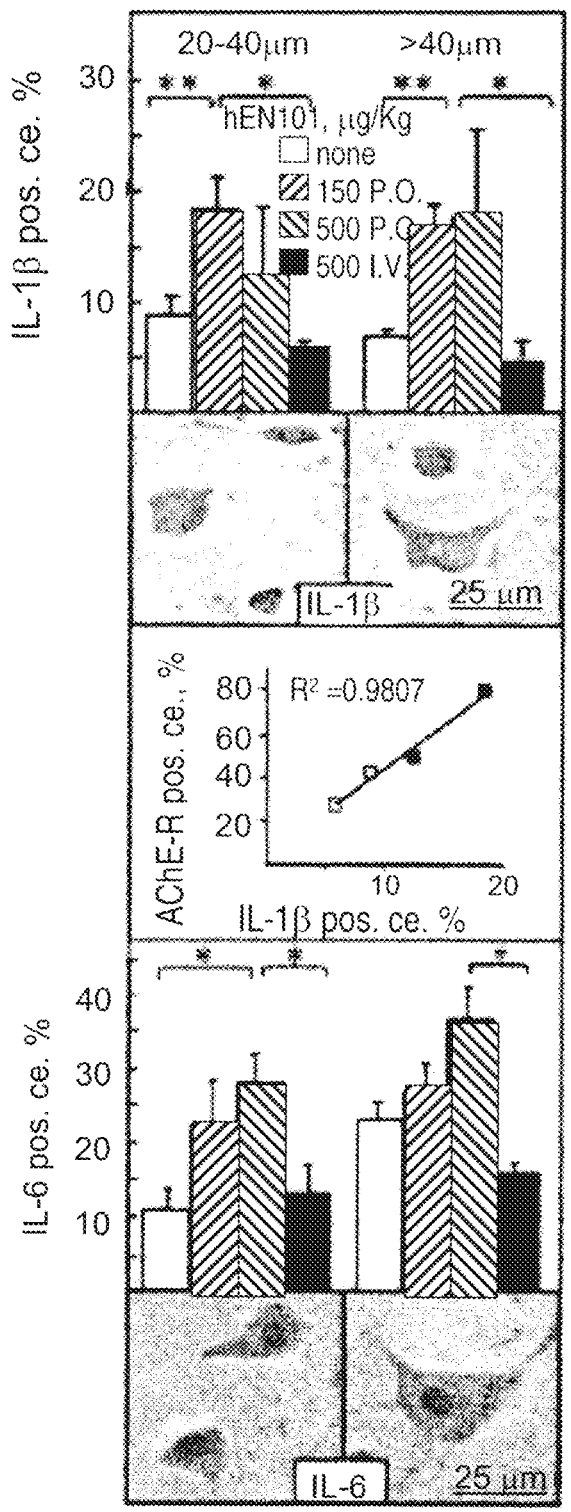

FIG. 4A-4C: Suppression of Stress-Induced Neuronal Pro-Inflammatory Cytokines Under Antisense Intervention with AChE-R Expression.

FIG. 4A: Shown are fractions of IL-1β positive spinal cord neurons of medium and large sizes under the different treatment regimens (columns plus or minus SEM representing repeated analyses of the ventral horn and intermediate zone of lumbar spinal cord gray matter in multiple sections). Insets: representative medium and large size positive neurons, taken from the p.o. 500 μg/kg/day regimen. *: $p≤0.05$, **: $p=0.067$.

FIG. 4B: Graph showing the correlation between the average fractions of AChE-R and IL-1β positive medium-sized cells (20-40 βm) in the different hEN101 treatments. Large cells (>40 μm) did not display such correlation ($R^2=0.1778$).

FIG. 4C: Fractions of IL-6 positive spinal cord neurons were evaluated essentially as under 4A. Note decreases in both IL-1β and IL-6 in spinal cord neurons of monkeys treated with 500 μg/kg/day EN101.

Abbreviations:

pos. ce., positive cells.

FIG. 5A-5D: Changes Over Time in the Human Plasma Levels of AChE Activity and in AChE-R Cleavage.

FIG. 5A: Hydrolytic activities. Shown are plasma AChE activities (mean±SEM) for ten volunteers injected twice, with endotoxin or saline (placebo) at the noted intervals after injection. Pre-injection (baseline) AChE level was considered as 100 percent for each individual. Asterisks denote statistical difference ($p<0.05$).

FIG. 5B: Immunoblot. Shown are consecutive results for one individual. Plasma samples underwent electrophoresis by SDS-PAGE, and the blot immunoreacted with anti-AChE-R antibodies. Note the 6.5 kDa AChE-R cleavage product. Left lanes indicate the response to a placebo injection; right lanes demonstrate elevated AChE-R cleavage in response to endotoxin.

FIG. 5C: Densitometric intensities. Shown are average values (mean plus or minus SEM) of the rapidly migrating AChE-R cleavage product in plasma of the endotoxin and placebo treated individuals as percent of baseline (described in A).

Note: Elevated AChE-R cleavage in endotoxin-treated subjects co-appeared with decreased AChE activity.

FIG. 5D: Association analysis. Highly significant negative association (correlation coefficient, $r=-0.65$) emerged between the increases in AChE-R cleavage and the decrease in AChE activity under endotoxin during the last testing period ($t=9$ hr). Each dot represents a single individual.

Abbreviations:

Act., activity; bas., baseline; H. p. inj., Hours post-injection; T. p. inj., Time post-injection; Plac., placebo; Endot., endotoxin; Cleav. Prod., cleavage product.

Figure 6:
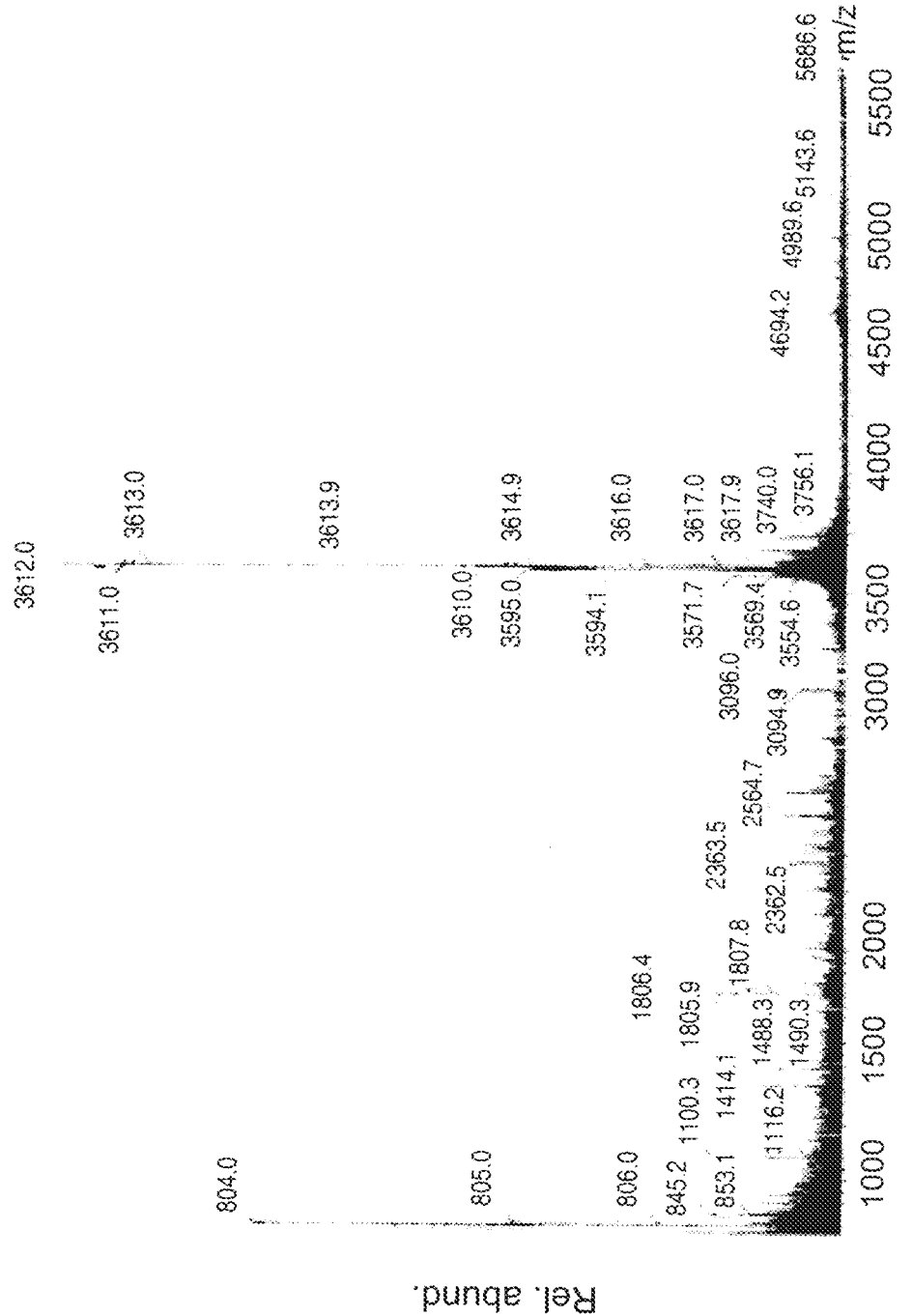

FIG. 6: Mass Spectroscopy of Gel-Eluted Band.

Shown is the outcome of electron spray mass spectrometry analysis of the gel-eluted rapidly migrating band that immunoreacted with anti-AChE-R antibodies. Note that the main peptide displayed a molecular mass of 3613-3615. Calculation of predicted masses positioned the presumed proteolytic cleavage site 36 residues from the C-terminus of AChE-R, between asparagine and arginine residues in the sequence presented, with the presumed cleavage site arrowed and the diversion site starred.

Abbreviations:

Rel. abund., relative abundance.

FIG. 7A-7C: AChE-R is Expressed in Human Vascular Endothelial Cells from Various Tissues.

FIG. 7A: AChE-R mRNA. Shown are the results of in situ hybridization using a 5'-biotinylated cRNA probe selective for the AChE-R mRNA variant on sections of human vascular endothelial cells affected by an inflammatory process (skin hypersensitivity vasculitis; labeling is seen as pink color, red arrow).

FIG. 7B: AChE-R Protein. Shown is an immunomicrograph of human kidney vascular endothelial cells from a patient with vasculitis, labeled with antibodies targeted at the AChE-R C-terminal peptide (red arrow).

FIG. 7C: Image analysis. Shown are average AChE-R mRNA and AChE-R protein labeling intensities (black and white columns, respectively), in kidney, skin and muscle vascular endothelial cells (mean values plus or minus SEM) as the percentage of red pixels, falling within a defined intensity range.

Abbreviations:

prot., protein; int., intensity; k. rej., kidney rejection; k. vas., kidney vasculitis; nonspec., non-specific; n. end., normal endothelium; m., muscle; hyp. vasc., hypersensitivity vasculitis.

Figure 8A:
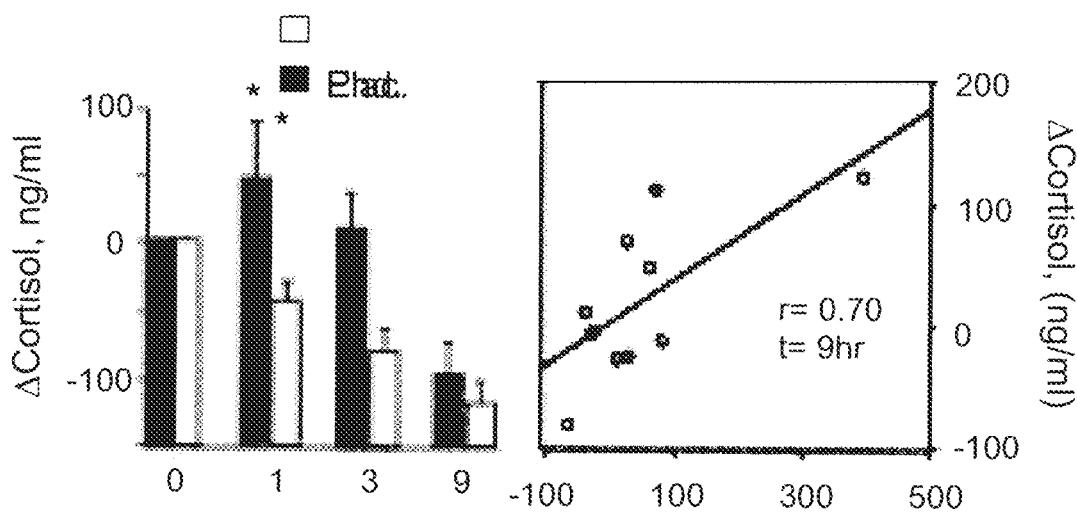
Figure 8B:
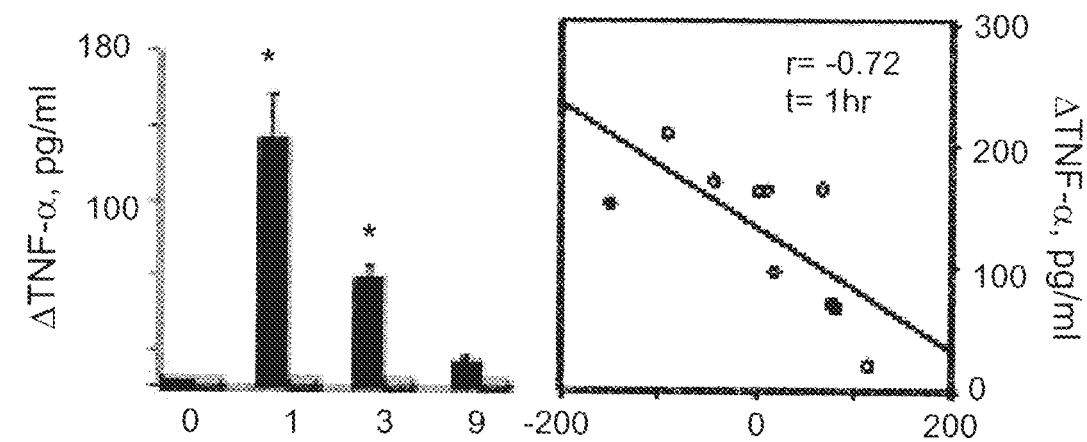
Figure 8C:
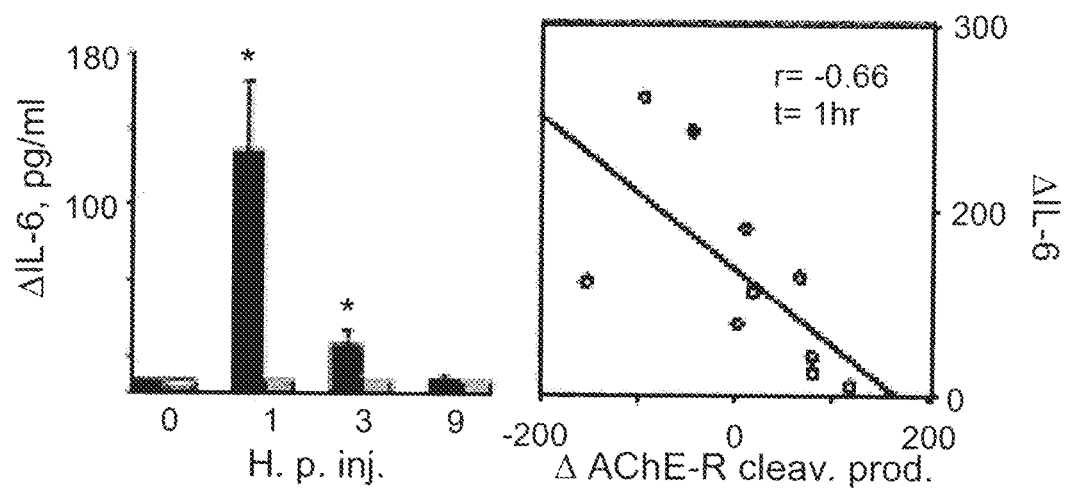

FIG. 8A-8C: Bidirectional Associations Between AChE-R Cleavage and the Changes in Cortisol and Cytokines.

Shown are average±SEM changes with time (left) in the plasma levels of cortisol, TNF-α and IL-6 of the 10 patients treated with endotoxin or placebo, and the associations (right) at the noted time points between these changes and the changes in AChE-R cleavage (measured by densitometric quantification of the C-terminus AChE-R cleavage product).

FIG. 8A: cortisol.

FIG. 8B: TNF-α.

FIG. 8C: IL-6.

Abbreviations:

r, correlation coefficient; t, time after injection; Plac., placebo; end., endotoxin; H. p. inj., hours post-injection; cleav. prod., cleavage product.

FIGS. 9A-9C: Endotoxin Impairs Declarative Memory.

Shown in FIG. 9A are average±SEM values for the performance in the immediate story recall test of the endotoxin and placebo treated individuals at the noted time following treatment as well as the associations of the changes in these values at 9 hr post-injection with the changes in AChE-R cleavage (FIG. 9B) and AChE activity (FIG. 9C).

Figure 10A:
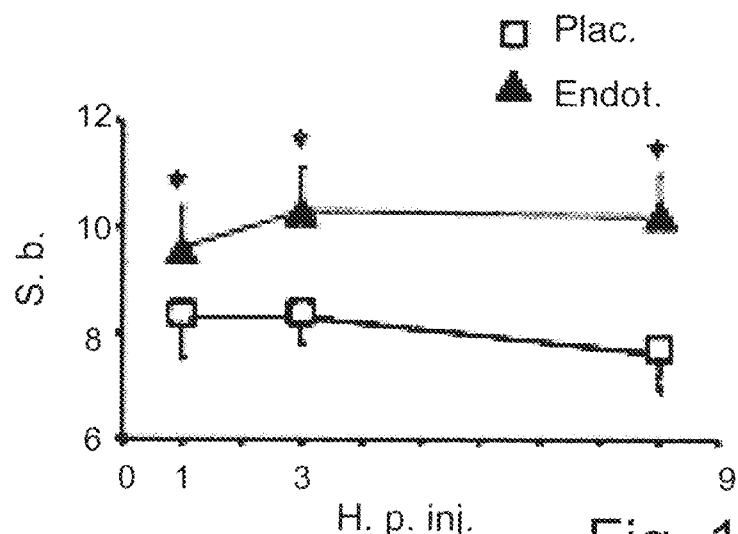
Figure 10B:
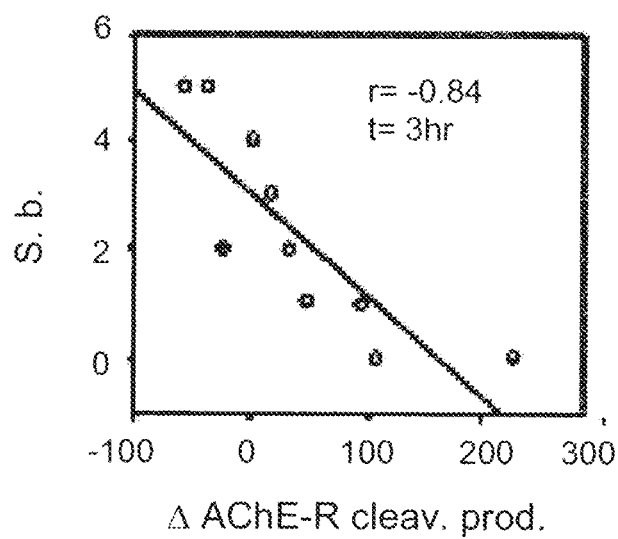

FIGS. 10A-B: Endotoxin-Induced Improvement in Working Memory.

Shown are the performance values (average+SEM) in the span background test for the endotoxin and placebo treated individuals (FIG. 10A) and the association of the changes in this performance at 3 hr post-injection with the changes in AChE-R cleavage (FIG. 10B).

Figure 11A:
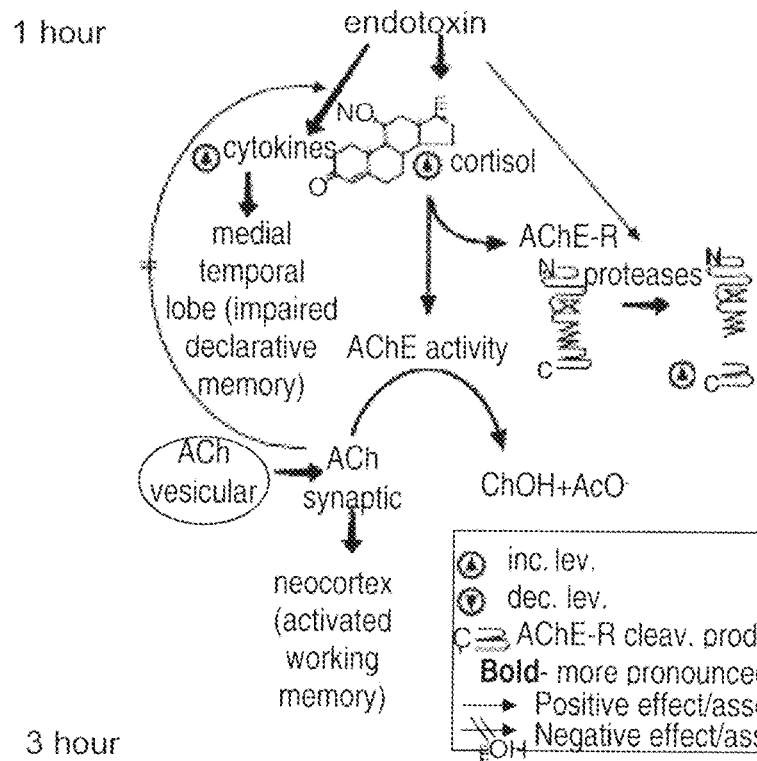
Figure 11B:
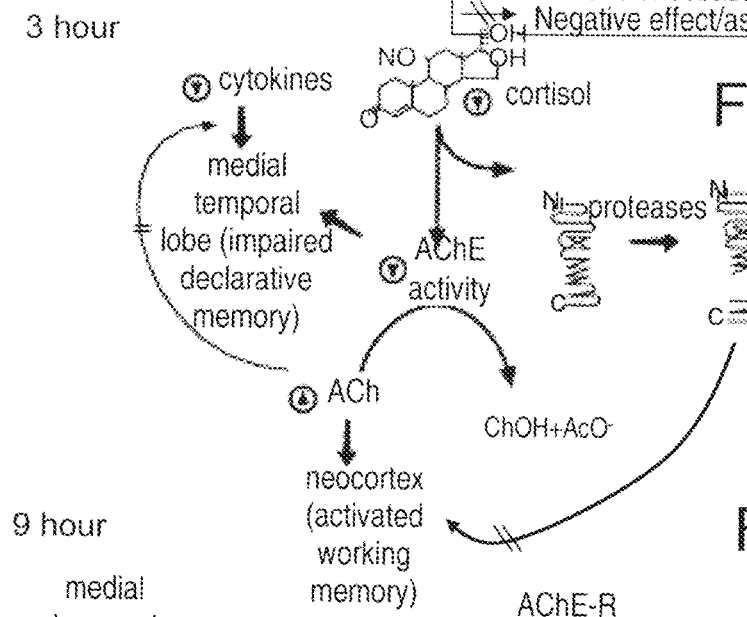
Figure 11C:
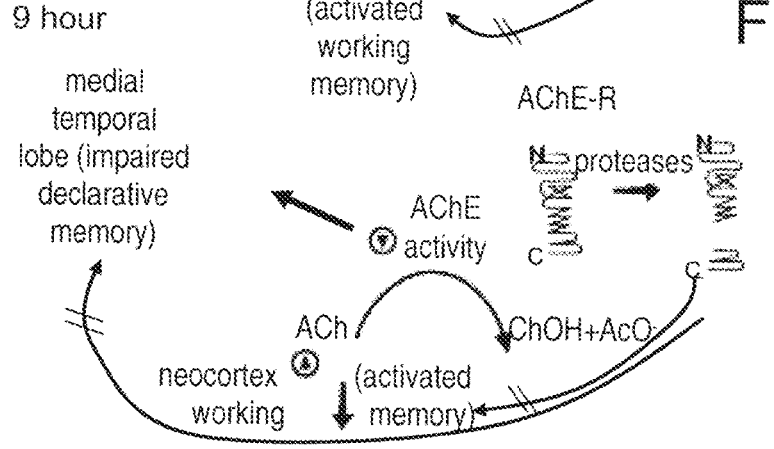

FIG. 11A-11C: Scheme-Endotoxin Induces Interrelated Cytokine-Cholinergic Effects on Memory.

Shown are the cellular and biochemical events that were explored in this study and which explain the changes in memory processes and the dynamic modifications in these changes during the post-treatment observation period. The thickness of arrows reflects the relative intensity of the relevant processes.

FIG. 11A: At 1 hr post-treatment: Endotoxin induces the release of cytokines, cortisol and proteases. Cytokines elevation associates with impaired declarative memory, which is a medial temporal lobe-associated phenomenon. Cortisol induces AChE-R production, which elevates the immunopositive AChE-R amounts in plasma. Vesicular ACh is released into the synaptic cleft, where it affects neuronal electrophysiology and may improve working memory, which is a neocortex-associated property. In the periphery, ACh begins to suppress cytokines production in macrophages (circular arrow).

FIG. 11B: At 3 hr post-treatment: Proteases release a C-terminal fragment of 36 amino acids in length from AChE-R and initiate further destruction, followed by decreases in AChE activity. Endotoxin is already gone, and ACh effectively suppresses cytokines production; Increased ACh levels (reflecting enhanced secretion and the decrease in AChE's hydrolytic activity) are probably associated with activated working memory, whereas the elevation in AChE-R cleavage product is associated with a lower working memory improvement.

FIG. 11C: At 9 hr Host-treatment: Cortisol is gone as well. However, the persistent, although slow decrease in AChE activity is associated both with the impaired declarative memory, and, probably through ACh increases, with the activated working memory. The steady increase in AChE-R cleavage product is now associated both with a greater impairment in declarative memory and with lower improvement in working memory.

Abbreviations:

inc. lev., increased level; dec. lev., decreased level; cleay. Prod., cleavage product.

Figure 12A:
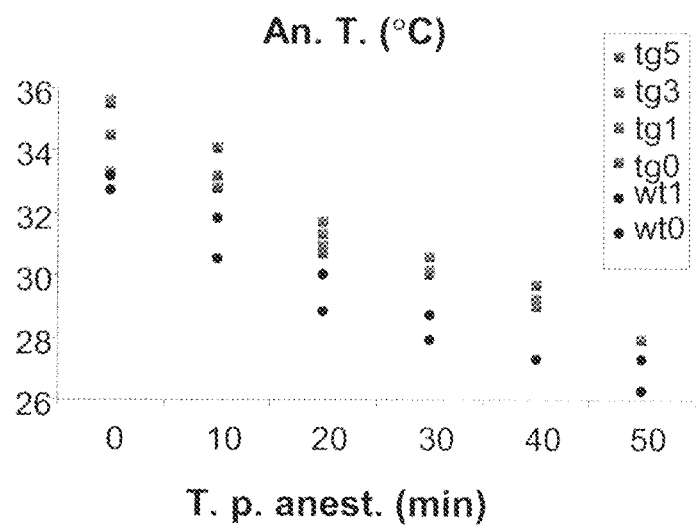
Figure 12B:
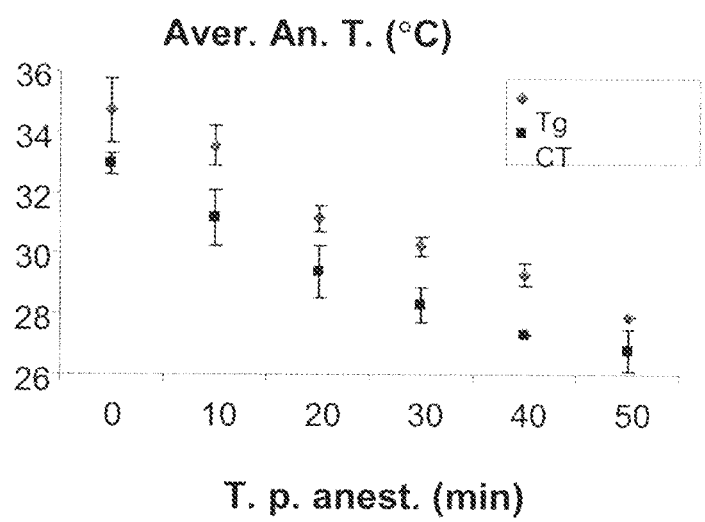

FIG. 12A-12B: Transgenic Mice Display Higher Body Temperature than Wild-Type Mice.

FIG. 12A: Graph showing the temperature of each mouse over time, squares represent transgenic mice, circles, control.

FIG. 12B: Graph showing the average temperature of each group (transgenic or control) over time, diamonds represent transgenic mice, squares, control.

Abbreviations:

An. T., Anal temperature; Aver. An. T., Average Anal temperature; T. p. anest., time post-anesthesia.

Figure 13A:
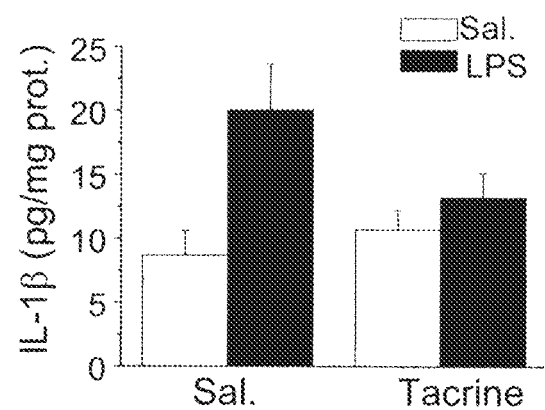
Figure 13B:
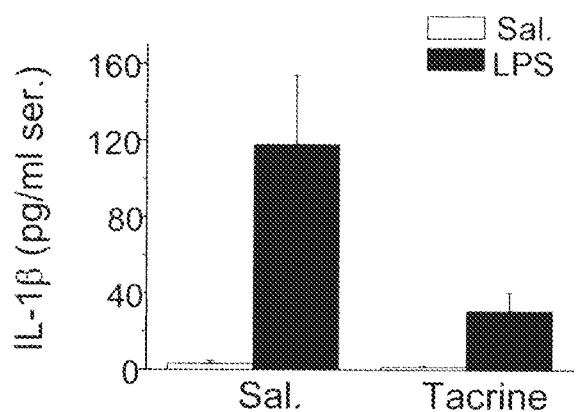
Figure 13C:
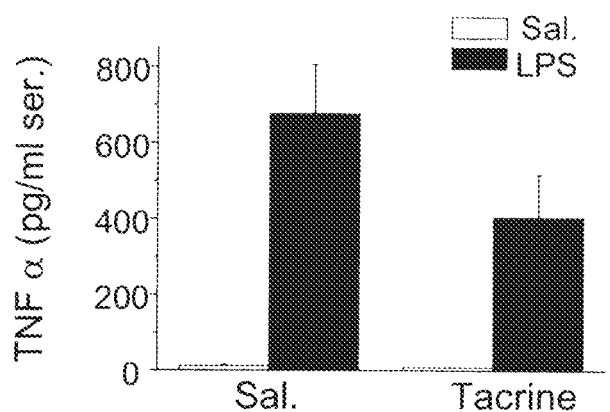

FIG. 13A-13C: Effects of Tacrine on LPS-Induced IL-1 Secretion in the Hippocampus and IL-1 and TNF-α Secretion in the Serum.

FIG. 13A: Graph showing the levels of IL-1 beta in the hippocampus.

FIG. 13B: Graph showing the levels of IL-1 beta in the serum.

FIG. 13C: Graph showing the levels of TNF-α in the serum.

Abbreviations:

prot., protein; ser., serum; sal., saline.

Figure 14A:
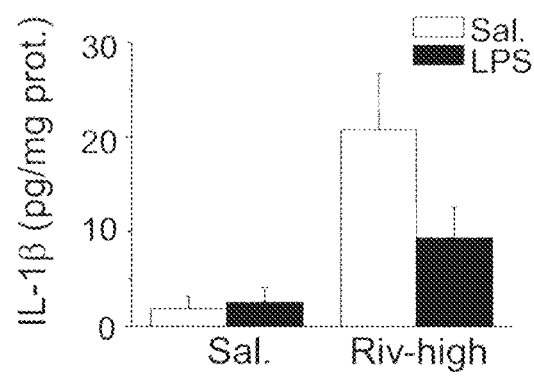
Figure 14B:
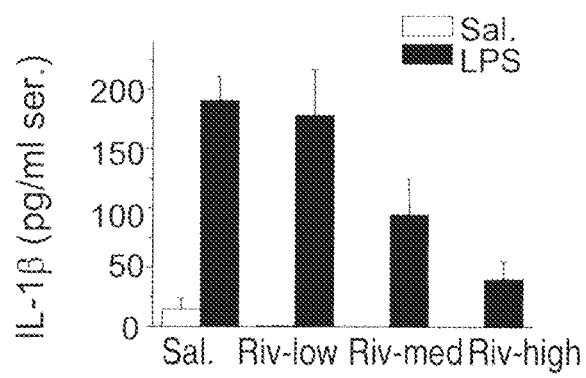
Figure 14C:
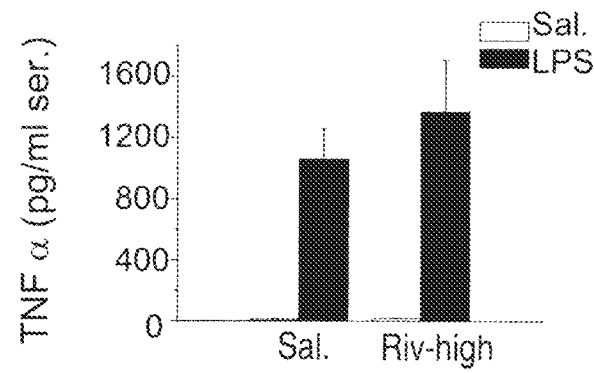

FIG. 14A-14C: Effects of Rivastigmine on LPS-Induced IL-1 Secretion in the Hippocampus and IL-1 and TNF-α Secretion in the Serum.

FIG. 14A: Graph showing the levels of IL-1β in the hippocampus.

FIG. 14B: Graph showing the levels of IL-1β in the serum.

FIG. 14C: Graph showing the levels of TNF-α in the serum.

Abbreviations:

prot., protein; ser., serum; sal., saline.

FIG. 15A-15H: Effects of Surgery Stress on Emotional and Cognitive Parameters.

FIG. 15A: Graph showing the effect of surgery stress on anxiety.

FIG. 15B: Graph showing the effect of surgery stress on depression.

FIG. 15C: Graph showing the effect of surgery stress on fatigue.

FIG. 15D: Graph showing the effect of surgery stress on pain.

FIG. 15E: Graph showing the effect of surgery stress on word list recall.

FIG. 15F: Graph showing the effect of surgery stress on word list recognition.

FIG. 15G: Graph showing the effect of surgery stress on story recall.

FIG. 15H: Graph showing the effect of surgery stress on figure recall.

Abbreviations:

Cont., control; str., stress; T., time; Anx., anxiety; Dep., depression; Fat., fatigue; P., pain; W.L.R., word list recall; W. L. Recog., word list recognition; S. R., story recall; Fig. R., figure recall.

Figure 16A:
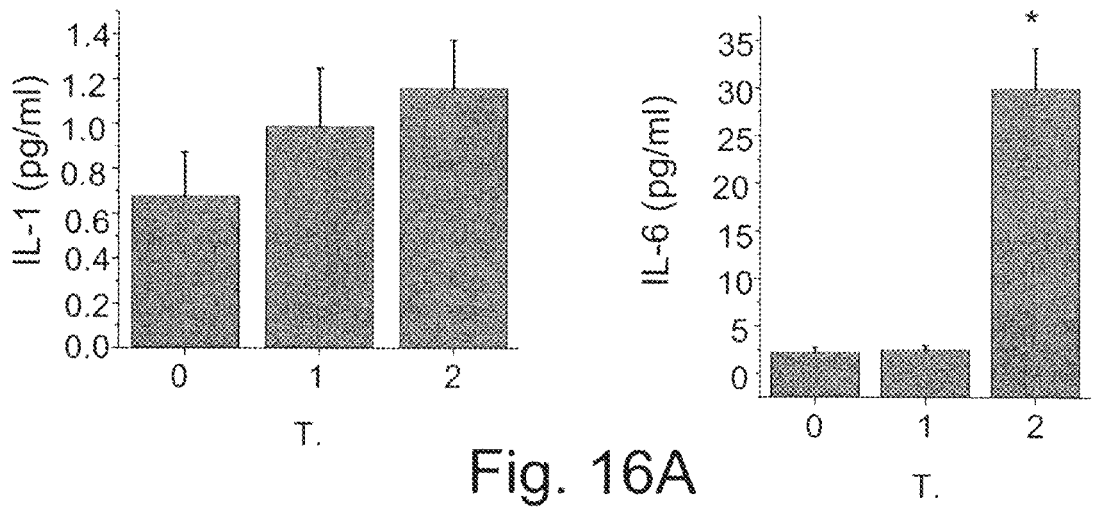
Figure 16B:
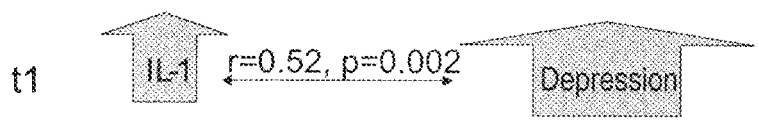
Figure 16C:
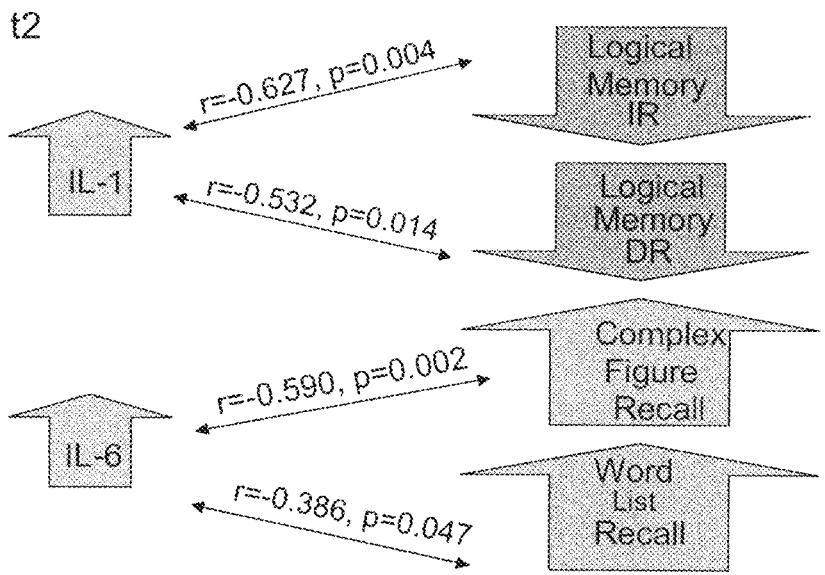

FIG. 16A-16C: Effect of Surgery Stress on Cytokine Levels.

FIG. 16A: Graph showing the effect of surgery stress on IL-1 and IL-6 levels.

FIG. 16B: Correlation between IL-1 and depression.

FIG. 16C: Correlation between cytokines and cognitive parameters.

Figure 17A:
Figure 17B:
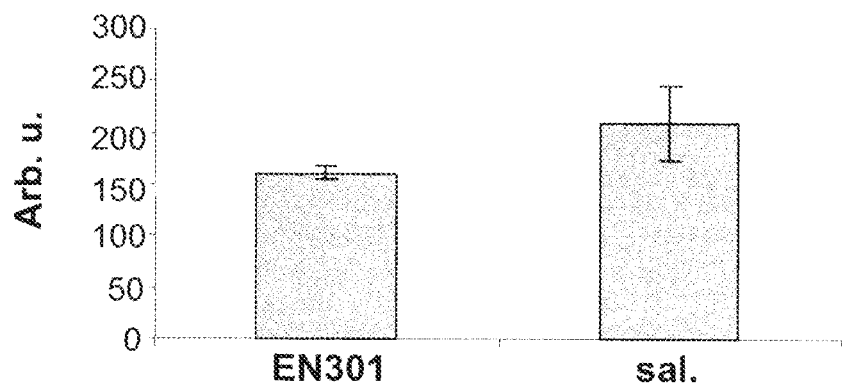
Figure 17C:
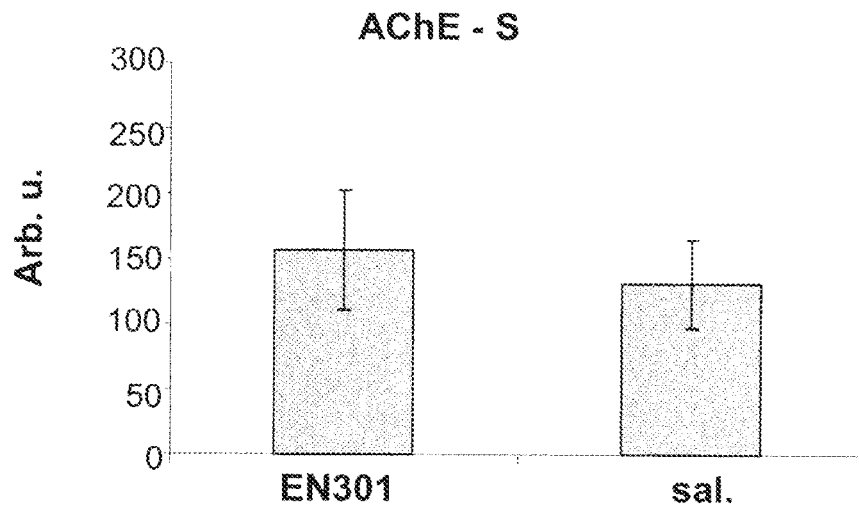

FIG. 17A-17C: Reduction of AChE Gene Expression Upon EN301 Treatment.

FIG. 17A: Analysis of RT-PCR reaction (AChE exon 2 product after 31 PCR cycles). From left to right: lane 1, marker; lanes 2-8, samples from EN301-treated mice; lanes 9-14, samples from PBS-treated mice.

FIG. 17B: Histogram representing quantitative analysis of the results obtained in the PCR reaction using primers targeting the common sequence in exon 2 of murine AChE cDNA.

FIG. 17C: Histogram representing quantitative analysis of the results obtained in the PCR reaction using primers targeting the sequence in exon 6 unique to the AChE-S variant.

Abbreviations:

c.d., common domain; Arb. U., arbitrary units; sal., saline.

Figure 18:
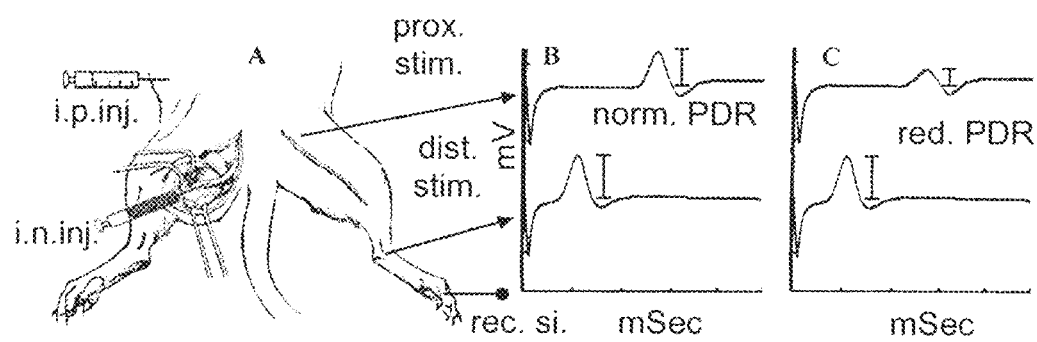

FIG. 18A-18C: Schematic Representation of Injections and Conduction Tracings in the GBS Model.

FIG. 18A: Systemic exposure was provided by intra-peritoneal (i.p.) injection (systemic injection). Intra-neural (i.n.) injections were to the sciatic nerve at the mid thigh level.

FIG. 18B: Compound muscle action potential is recorded from the intrinsic foot muscles following proximal stimulation of the sciatic nerve at the sciatic notch and distal stimulation of the peroneal and posterior tibial nerves at the ankle.

FIG. 18C: Proximal to distal amplitudes ratio (PDR) of less than 0.5 indicates conduction block.

Abbreviations:

inj., injection; red., reduced; norm., normal; prox. stim., proximal stimulation; dist. stim., distal stimulation; rec. si., recording site.

FIG. 19A-19D: Histograms Representing Average Proximal to Distal Amplitude Ratio (PDR) in Selected Experiments.

Measurements were obtained one day following intra-neural injection or on the second post-injection day, where designated.

Abbreviations:

i.n., intra-neural; i.p., intra-peritoneal; LPS, lipopolysaccharide; EN101 or AS, antisense oligonucleotide; SM, splenocyte medium; BMM, bone marrow macrophage; ARP, AChE-readthrough peptide; ASP, AChE-synaptic peptide; n., none; sal., saline; inj., injection; PID2, second post-injection day; I.N.Inj., intra-neural injection; LPS-R, lipopolysaccharide-reactive.

Figure 20:
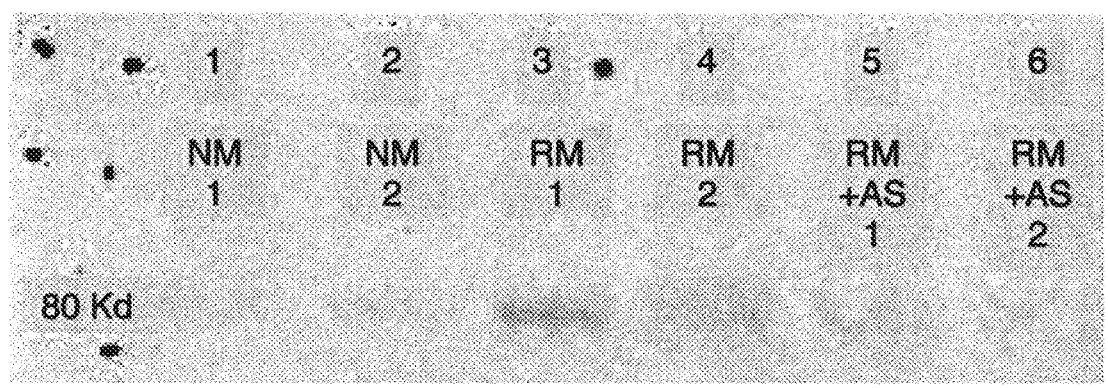

FIG. 20: Immunoblot Signal for PKCβII. Expression of PKCβII is increased following intra-neural injection (i.n.) of LPS-reactive splenocyte medium in two nerves (RM, lanes 3,4) compared to two nerves injected with non-reacted splenocyte medium (NM, lanes 1,2). This increase is attenuated in two nerves by concomitant i.n. injection of antisense EN101 (RM+EN101, lanes 5,6).

DETAILED DESCRIPTION OF THE INVENTION

For the purposes of clarity, the following abbreviations and terms are defined herein:

AChE: acetylcholinesterase

AChE-R: acetylcholinesterase, "readthrough" variant or isoform, its mRNA includes pseudo-intron 14

AChE-S: acetylcholinesterase, synaptic variant or isoform

AS-ON: antisense oligonucleotide

CMAP: compound muscle action potential

CNS: central nervous system

EN101: may also be referred as AS3, antisense oligonucleotide targeted against human, rat or mouse (hEN101, rEN101 or mEN101, respectively) AChE mRNA EN301: may also be referred as mEN101, antisense oligonucleotide targeted against mouse AChE mRNA GBS: Guillain-Barre Syndrome
i.n.: intraneural
i.p.: intraperitoneal
i.v.: intravenous
o.g.: oral gavage
p.o.: per os
PDR: proximal to distal amplitude ratio Antisense oligonucleotide: A nucleotide comprising essentially a reverse complementary sequence to a sequence of AChE mRNA. The nucleotide is preferably an oligodeoxynucleotide, but also ribonucleotides or nucleotide analogues, or mixtures thereof, are contemplated by the invention. The antisense oligonucleotide may be modified in order to enhance the nuclease resistance thereof, to improve its membrane crossing capability, or both. The antisense oligonucleotide may be linear, or may comprise a secondary structure. It may also comprise enzymatic activity, such as ribozyme activity.

To reveal if cholinergic allostasis and CNS inflammatory processes are inter-related, the inventors studied spinal cord neurons from Cynomolgus monkeys following one week daily treatment with hEN101 (SEQ ID NO:1), a 2'-oxymethylated antisense oligonucleotide inducing AChE-R mRNA destruction. hEN101 prevented the stress-induced increases in plasma AChE activities and selectively suppressed neuronal AChE-R mRNA and interleukins-1β and -6 levels in a dose- and cell size-dependent manner. In contrast, VAChT and ChAT levels were reduced dose-independently in all of the handling-stressed monkeys, demonstrating distinct regulation for the corresponding genes. These findings allude to a causal association between cholinergic allostasis and inflammatory responses in the primate CNS and suggest antisense intervention with AChE-R accumulation for the management of both these impairments. Furthermore, EN101 intervention in a GBS model prevented the appearance of nerve conduction block following both in vivo and in vitro exposure to Cj-LPS, and had a similar affect by exposure to *E. Coli* LPS.

Thus, the present invention refers to the use of an inhibitor of AChE expression, as an anti-inflammatory agent. Mainly, the present invention provides methods of treatment and/or prevention of conditions selected from the group consisting of: conditions triggering an inflammatory response, inflammation, release of pro-inflammatory cytokines, fever, and inflammation-associated neuropathies, particularly GBS, said method comprising administering a therapeutic effective amount of an inhibitor of AChE expression, or a pharmaceutical composition comprising the same, to a subject in need.

As herein defined, an inhibitor of AChE expression is any agent which is capable of blocking or hindering the expression of the AChE gene, particularly by interacting with its mRNA. Thus, said inhibitor may be an AChE-specific ribozyme, a double-stranded nucleotide sequence used for RNA interference of the AChE gene, or an antisense oligonucleotide directed against AChE. Antisense nucleotides are preferably nuclease resistant.

Preferably, said inhibitor of AChE expression selectively inhibits the AChE-R mRNA, consequently selectively inhibiting the expression of the AChE-R isoform. In this regard, any agent capable of inhibiting the soluble AChE-R isoform may also be an anti-inflammatory agent. Therefore, a putative molecule that could block AChE-R expression and/or function would be an anti-inflammatory agent.

Nonclinical studies demonstrated anti-inflammatory effects of hEN101 equivalent to those of dexamethasone in a TNBS-induced mouse colitis model. It is thus a suitable agent for the treatment of inflammatory bowel disease and other inflammatory gastrointestinal disorders, as well as gastrointestinal immune disorders.

As shown in the following Examples A and B, the safety of hEN101 is supported by its low systemic exposure observed in both animal and human studies. There was very limited systemic exposure of animals to hEN101 at dose levels of up to 1000 mg/kg/day which is several orders of magnitude above the clinical range and this exposure was associated with no toxicity as mentioned above. In the current clinical study conducted in humans hEN101 levels in the plasma of patients treated orally with doses up to 40 mg/day were shown to be below the limit of detection of 3.3 ng/mL. It is to be noted that when delivered systemically, oligonucleotides are rapidly cleared from the circulation.

Oral administration of hEN101 has several major advantages. First, since most oligonucleotides are administered parentally due to low bioavailability following oral administration, the bioavailability exhibited by orally administered hEN101 constitutes a major advantage in terms of patient compliance, costs and others.

As shown in the examples below, a positive clinical response was obtained after treatment of patients with patients with moderately active ulcerative colitis with hEN101, orally administered at a dose of 12 mg/day hEN101 for 19-21 days, followed by a dose of 40 mg/day hEN101 for 14 days. As shown in Table 4 in the following examples A and B, by the end of the study, in 6 out of 7 patients there was a reduction of at least 50% in Mayo score. Remarkably, in 3 of the 7 patients there was a reduction of over 60% in Mayo score (i.e. 62.5% and 66% reduction).

Thus, hEN101 proved efficient in the treatment of gastrointestinal inflammatory disorders.

As shown in Example 1, BuChE levels in the plasma of treated monkeys were not significantly altered, supporting the notion of a selective antisense effect over AChE alone. Both plasma AChE activity and neuronal AChE mRNA labeling increased in monkeys treated with 150 µg/kg hEN101, potentially reflecting increased production at the tested daily time (Table 1 and data not shown). Alternatively, or in addition, the mild stress associated with the insertion of cannula for p.o. administration of hEN101 could be the cause. Plasma AChE increases in the absence of hEN101 would likely be even higher, as is indicated from the suppression of plasma AChE activity in monkeys treated similarly with the higher dose of 500 µg/kg hEN101. An apparent 3 hr delay was observed in the drug-induced decreases of plasma AChE under this low hEN101 dose, possibly reflecting prevention by antisense agents of the synthesis of their target protein(s). This further indicates a short half life for primate AChE-R mRNA in vivo, compatible with previous findings by the inventors and others [Brenner et al. (2003) id ibid.; Chan, R. Y. et al. (1998) *J. Biol. Chem.* 273, 9727-9733].

The fraction of AChE-R mRNA positive neurons, the intensity of AChE-R mRNA labeling and the fraction of cells with AChE-R mRNA labeled processes were all reduced under antisense treatment (FIGS. 2A-2J and 3A-3C). Neuronal susceptibility of AChE-R overproduction to antisense suppression appeared inversely proportional to cell body size, possibly reflecting distinct membrane and/or metabolic properties, different cell volumes or a combined contribution of these properties. In addition, antisense-independent reductions in VAChT and ChAT likely indicated a slowdown of vesicle recycling [Soreq, H. et al. (1990) *Proc Natl Acad Sci U.S.A.* 87: 9688-9692], potentially modulating the pace of cholinergic neurotransmission. Under naive conditions, AChE-S mRNA appeared in processes of many more spinal cord neurons than AChE-R mRNA, creating a pattern reminiscent of VAChT labeling in the rat spinal cord ventral horn [Weihe et al. (1996) id ibid]. Expectedly, hEN101 treatment was highly efficient with neuronal AChE-R mRNA and much less effective with ACNE-S mRNA. However, the reduced intensity of neuronal AChE-S mRNA labeling likely reflected limited reduction in neuronal AChE-S mRNA levels as well. Under hEN101 treatment, AChE-S mRNA in processes was reduced, suggesting common tendency for reduced dendrite translocation of the rodent and primate AChE-S mRNA transcript under stress [Meshorer et al. (2002) id ibid]. This difference further strengthened the notion that the naive monkey was indeed under no stress, an important fact in a study with strictly limited number of animals. The reduced AChE-S mRNA in neuronal processes of the treated monkeys may be treatment- and/or drug-induced. Following 7 days treatment, a shift from the primary AChE-S mRNA transcript to the stress-induced antisense-suppressible AChE-R mRNA may be visualized in the neuronal processes (FIG. 2A-2J).

Preferably, said inhibitor of AChE expression is an antisense oligonucleotide directed against AChE, having any one of the following sequences: 5' CTGCCACGTTCTCCTG-CACC 3' (SEQ ID NO:1); and 5' CTGCCACGTTCTCCTGCA*C*C*3' (SEQ ID NO:7), wherein the three 3' terminal residues are modified with 2-O-methyl groups (*).

The antisense oligonucleotides denoted by SEQ ID NO:1 or SEQ ID NO:7 are also referred to herein as EN 101, or hEN 101. hEN 101 is also commercially known as Monarsen™.

The antisense oligonucleotides directed against AChE have been described in the past by the present inventors [WO 03/002739], and were shown to have a potent effect in the treatment of the neuromuscular pathology myasthenia gravis [applicant's co-pending US 2003/0216344]. In the inventors' herein described results, as shown in Example 5 and FIG. 4, the antisense oligonucleotide directed against AChE was able to reduce the release of IL-1β, which is a pro-inflammatory cytokine.

As shown in Example 1, AChE-R mRNA levels in motoneurons were minimally affected, however, elimination of AChE-R production in spinal cord smaller neurons potentially increased ACh signaling within the treated tissue, in spite of the stress-induced reduction in VAChT and ChAT [Kaufer et al. (1998) id ibid]. This attributes to AChE-R the primary role of regulating ACh levels in the CNS. Findings of others show large variability in the electrophysiological activity patterns of spinal cord interneurons [Perlmutter (1996) id ibid.] as well as pre-movement instructed delay activity in them [Prut and Fetz (1999) id ibid]. The inventors observed the largest variability in AChE-R levels within small cells, probably interneurons, suggesting that these modulations may contribute towards the wide electrophysiological variability between these neurons. Under normal conditions, AChE-R expression in small cholinergic neurons, localized to the dorsal horn of the spinal cord, may thus contribute to the control of motoneuron activities (e.g. motor reflexes). C-terminal structures, which affect the cholinergic input to motoneurons, were considered to originate in proximity to the motoneurons themselves [Hellstrom (1999) id ibid]. This study attributes this origin to AChE mRNA positive interneurons and small cholinergic neurons located in the ventral horn and intermediate zone of the lumbar spinal cord. The numbers of VAChT-labeled C-terminals surrounding motoneuron cell bodies decreased in all of the handled animals. This observation attributes this decrease to the handling stress, compatible with the stress-induced decreases in ChAT and VAChT mRNA in hippocampal neurons [Kaufer et al. (1998) id ibid].

Additional antisense oligonucleotides directed against AChE have also been described, and potentially have the same anti-inflammatory effect as hEN101, as demonstrated in Example 16 for mEN101. These are antisense oligonucleotides derived from the mouse and the rat AChE homologous sequences, which have the following sequences:

```
mEN101
                                         (SEQ. ID. NO: 2)
5'-CTGCAATATTTTCTTGCACC-3' [Grifman and Soreq, (1997) Antisense Nucleic Acid Drug Dev. 7(4):

351-9] also referred herein as EN301.

rEN101
                                         (SEQ. ID. NO: 3)
5'-CTGCCATATTTTCTTGTACC-3' hEN103
                                         (SEQ. ID. NO: 4)
5'-GGGAGAGGAGGAGGAAGAGG-3' [Grisaru, D. et al.

(1999) Mol. Cell Biol. 19(1): 788-95]
```

Example 16 demonstrates how administration of mEN101 (EN301) was able to reduce the levels of AChE-R in the brain. This could be done directly, upon crossing the blood-brain-barrier, or indirectly, by reducing the levels of peripheral AChE, increasing the levels of ACh, which would then suppress the production of pro-inflammatory cytokines by macrophages.

Thus, the present invention provides the use of an inhibitor of AChE as defined herein, as a suppressor of pro-inflammatory cytokines release. Known pro-inflammatory cytokines are IL-1β, TNFα, IL-6, IL-8, IL-12 and IL-18, amongst others.

Preferably, IL-1β is the pro-inflammatory cytokine to be suppressed by the method of the invention upon administration of an antisense oligonucleotide denoted by any one of SEQ ID NO:1, SEQ ID NO:2 and SEQ ID NO:7, or a composition comprising thereof, to a subject in need.

Pro-inflammatory cytokine release may be triggered by factors of acquired, chemical or genetic origin. Amongst others, these may be stress, bacterial infection, drugs, irradiation, exposure to AChE inhibitors, stroke, auto-immune diseases, multiple chemical sensitivity, or any cumulative age-dependent damages.

Known conditions which trigger pro-inflammatory cytokine release are: bacterial infection, drugs, irradiation, exposure to AChE inhibitors, stroke, auto-immune diseases, multiple chemical sensitivity, or any cumulative age-dependent damages.

Stress-induced spinal IL-1β over-production and spinal IL-1β suppression following AS-ON inhibition of AChE-R, support the notion of cholinergic regulation of anti-inflammatory response in the CNS. According to this scheme, "stressed" neurons produce high levels of AChE-R, reducing ACh and allowing uninterrupted production of IL-1β in CNS neurons that do not express IL-1β under normal conditions. Antisense suppression of the stress-induced AChE-R would increase ACh levels, which can then suppress IL-1β production in CNS neurons. Such cholinergic regulation of inflammatory response within the CNS may explain both the increase of pro-inflammatory cytokines under cholinergic imbalance (e.g. exposure to organophosphate compounds) [Svensson (2001) id ibid.; Dyer (2001) id ibid.] and the decrease of those same cytokines under retrieval of cholinergic balance (e.g. under antisense treatment, see FIG. 6).

This provides a new understanding of the improvement of survival and clinical status in EAMG rats receiving daily oral doses of EN101 as compared to the conservative AChE inhibitor (pyridostigmine) [Brenner (2003) id ibid.].

It is known in the literature that IL-1β induces arthritis in chondrocytes by suppressing Co12 gene expression [Hollander et al. (1994) *J. Clin. Invest.* 93: 1722; Hollander et al. (1995) *J. Clin. Invest.* 96: 2859; Bi et al., (1999) *Nat. Genet.* 22: 85; Lefebvre et al., (1997) *Mol. Cell. Biol.* 17: 2336; Muraknmi et al. (2000) *J. Biol. Chem.* 275: 3687; Tanaka et al. (2000) *Mol. Cell. Biol.* 20: 4428]. Therefore, the inhibition of IL-1 β release by the antisense oligonucleotide herein described might result in cartilage regeneration. Thus, the invention also provides the use of an inhibitor of AChE expression, as defined herein, as an inducer of cartilage regeneration.

The antisense oligodeoxynucleotides used as anti-inflammatory agents in the present invention are preferably nuclease resistant. There are a number of modifications that impart nuclease resistance to a given oligonucleotide. Reference is made to WO 98/26062, which publication discloses that oligonucleotides may be made nuclease resistant e.g., by replacing phosphodiester internucleotide bonds with phosphorothioate bonds, replacing the 2'-hydroxy group of one or more nucleotides by 2'-methyl groups, or adding a nucleotide sequence capable of forming a loop structure under physiological conditions to the 3' end of the antisense oligonucleotide sequence. An example for a loop forming structure is the sequence 5'-CGCGAAGCG-3', which may be added to the 3' end of a given antisense oligonucleotide to impart nuclease resistance thereon.

Phosphorothioate-modified oligonucleotides are generally regarded as safe and free of side effects. The antisense oligonucleotides of the present invention have been found to be effective as partially phosphorothioates and yet more effective as partially 2-O-methyl protected oligonucleotides. WO 98/26062 teaches that AChE antisense oligonucleotides containing three phosphorothioate bonds out of about twenty internucleotide bonds are generally safe to use in concentrations of between about 1 and 10 µM. However, for long-term applications, oligonucleotides that do not release toxic groups when degraded may be preferred. These include 2'-O-methyl protected oligonucleotides, but not phosphorothioate oligonucleotides. A further advantage of 2'-O-methyl protection over phosphorothioate protection is the reduced amount of oligonucleotide that is required for AChE suppression. This difference is thought to be related to the improved stability of the duplexes obtained when the 2'-O-methyl protected oligonucleotides are used [Lesnik, E. A. and Freier, S. M. (1998) *Biochemistry* 37, 6991-7]. An alternative explanation for the greater potency of the 2'-O-methyl oligonucleotides is that this modification may facilitate penetration of the oligonucleotide chain through the cell membrane. A further advantage of 2'-O-methyl protection is the better protection against nuclease-mediated degradation that it confers, thus extending the useful life time of antisense oligonucleotides protected in this way. Further, the inhibitor of AChE as defined above may also be used as an anti-pyretic. Thus, the antisense oligonucleotides denoted by any one of SEQ ID NO:1, SEQ ID NO:2 and SEQ ID NO:7, or compositions comprising thereof, may be used in the method of the invention for treating fever, or lowering body temperature, in a subject in need.

In response to anesthesia, neural regulation induces rapid decrease in body temperature. As shown in Example 12, transgenic mice with host AChE-R elevation show inherently higher body temperature as compared to strain, gender and age-matched controls. Furthermore, their body temperature remains higher also under anesthesia, demonstrating impaired regulation and tentative association of AChE-R with pyrogenic responses. Thus, inhibitors of AChE-R expression would also have an effect in lowering the elevated body temperature that is characteristic of inflammatory reactions.

Normal body temperature varies by person, age, activity, and time of day. The average normal body temperature is 37° C. (98.6° F.). An at least half-degree elevation of the average temperature may already be considered as fever.

Fever, or elevated body temperature, may be triggered by various causes, including: viral and bacterial infections, colds or flu-like illnesses, sore throats and strep throat, ear infections, viral gastroenteritis or bacterial gastroenteritis, acute bronchitis, infectious mononucleosis, urinary tract infections, upper respiratory infections (such as tonsillitis, pharyngitis or laryngitis), medications (such as antibiotics, antihistamines, barbiturates, and drugs for high blood pressure), occasionally, more serious problems like pneumonia, appendicitis, tuberculosis, and meningitis, collagen vascular disease, rheumatoid diseases, and autoimmune disorders, juvenile rheumatoid arthritis, lupus erythematosus, periarteritis nodosa, AIDS and HIV infection, inflammatory bowel disease, regional enteritis, ulcerative colitis, cancer, leukemia, neuroblastoma, Hodgkin's disease and non-Hodgkin's lymphoma.

In accordance with the invention, the dosage of the antisense oligodeoxynucleotide is about 0.001 to 50 µg oligonucleotide per gram of body weight of the treated mammalian subject, and it is for daily use. Preferably, the dosage is about 0.01 to about 5.0 µg/g. More preferably, the dosage is between about 0.05 to about 0.7 µg/g. Thus, the optimal dose range is between 50-500 µg/kg of body weight of the treated subject, for rats, monkeys and most importantly humans. This dosage refers to the antisense oligonucleotide administered per se, or in solution, in a pharmaceutical composition. Further, the present invention also provides a pharmaceutical composition for the treatment of conditions triggering an inflammatory response in a mammalian subject in need, preferably a human, comprising as active agent the above-defined inhibitor of AChE expression. Optionally, the composition further comprises pharmaceutically acceptable additives, carriers and/or diluents. Preferably, said inhibitor of AChE expression is an antisense oligonucleotide directed against AChE, and has the sequence as denoted by any one of SEQ ID NO:1 and SEQ ID NO:7.

Alternatively, wherein said mammalian subject is a non-human mammalian, said antisense nucleotide has the sequence as denoted by any one of SEQ ID NO:2 and SEQ ID NO:3.

In a yet further aspect, the present invention provides a pharmaceutical composition for the treatment and/or prevention of inflammation in the joints, central nervous system, gastrointestinal tract, endocardium, pericardium, lung, eyes, skin and urogenital system in a mammalian subject in need, comprising as active agent the inhibitor of AChE expression as defined above, optionally further comprising pharmaceutically acceptable additives, carriers and/or diluents. Preferably, said inhibitor of AChE expression is an antisense oligonucleotide. Inflammation of the gastrointestinal tract includes, but is not limited to, Irritable Bowel Syndrome (IBS), Inflammatory Bowel Syndrome, Inflammatory Bowel Disease (IBD), Crohn's Disease and ulcerative colitis.

More preferably, wherein said mammalian subject is a human, said antisense nucleotide has the sequence as denoted by any one of SEQ ID NO:1 and SEQ ID NO:7.

Alternatively, wherein said mammalian subject is a non-human mammalian, said antisense nucleotide has the sequence as denoted by any one of SEQ ID NO:2 and SEQ ID NO:3.

The inhibitor of AChE expression, as defined above, is to be used in the preparation of the pharmaceutical composition comprising the same.

The antisense oligonucleotides described herein are generally provided in the form of pharmaceutical compositions. Said compositions are for use by injection, topical administration, or oral uptake.

Thus, the present invention also provides the use of the antisense oligonucleotides described herein, and preferably the use of the antisense oligonucleotides denoted by SEQ ID NO:1 and SEQ ID NO:7, in the preparation of a pharmaceutical composition for the treatment or prevention of conditions triggering an inflammatory response in a subject in need. In particular, said conditions are selected from the group comprised of inflammation in the joints, central nervous system, gastrointestinal tract, endocardium, pericardium, lung, eyes, skin, urogenital system, fever, the release of pro-inflammatory cytokines, stroke, brain and peripheral nerve trauma, neurodegenerative diseases (e.g. vascular dementia), closed head injury, memory impairment, and inflammation-associated neuropathies (e.g. Guillain-Barre syndrome).

Furthermore, the pharmaceutical composition of the invention may comprise as active agent a combination of at least two antisense oligonucleotides as defined in the invention, or functional analogs, derivatives or fragments thereof.

By "analogs and derivatives" is meant the "fragments", "variants", "analogs" or "derivatives" of said nucleic acid molecule. A "fragment" of a molecule, such as any of the oligonucleotide sequences of the present invention, is meant to refer to any nucleotide subset of the molecule. A "variant" of such molecule is meant to refer a naturally occurring molecule substantially similar to either the entire molecule or a fragment thereof. An "analog" of a molecule can be without limitation a paralogous or orthologous molecule, e.g. a homologous molecule from the same species or from different species, respectively.

Preferred modes of administration of the inhibitor of AChE expression or pharmaceutical compositions comprising the same are by subcutaneous, intraperitoneal, intravenous, intramuscular or systemic injection.

The pharmaceutical composition described herein generally comprises a buffering agent, an agent which adjusts the osmolarity thereof, and optionally, one or more carriers, excipients and/or additives as known in the art, e.g., for the purposes of adding flavors, colors, lubrication, or the like to the pharmaceutical composition.

A preferred buffering agent is Trig, consisting of 10 mM Tris, pH 7.5-8.0, which solution is also adjusted for osmolarity.

For in vivo use, the antisense oligonucleotides are suspended is sterile distilled water or in sterile saline.

Other carriers may include starch and derivatives thereof, cellulose and derivatives thereof, e.g., microcrystalline cellulose, xantham gum, and the like. Lubricants may include hydrogenated castor oil and the like.

Topical administration of pharmaceutical compositions may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

The pharmaceutical compositions described herein include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical compositions of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. Such compositions may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

The pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

In one embodiment, the pharmaceutical composition of the invention is for daily use by a subject in need of such treatment, at a dosage of active ingredient between about 0.001 µg/g and about 50 µg/g. Preferably, the treatment and/or prevention comprises administering a dosage of active ingredient of about 0.01 to about 5.0 µg/g. Most preferably, said dosage of active ingredient is of between about 0.05 to about 0.70 µg/g, and even most preferably, the dosage is from 0.15 to 0.50 µg/g of body weight of the subject in need.

Persons of ordinary skill in the art can easily estimate repetition rates for dosing based on measured residence times and concentrations of the antisense oligonucleotide in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The preparation of pharmaceutical compositions is well known in the art and has been described in many articles and textbooks, see e.g., Gennaro A. R. ed. (1990) *Remington's Pharmaceutical Sciences*, Mack Publishing Company, Easton, Pa., and especially pages 1521-1712 therein.

The results presented herein are the first demonstration of an organismal antisense response that affects primate CNS neurotransmission (Example 1). Positron Emission Tomography (PET) imaging studies in Rhesus monkeys demonstrated for 2'-β-methylated oligonucleotides limited, yet relatively long-term persistence in the brain as compared with phosphothioate agents [Tavitian (1998) id ibid]. In addition, the blood-brain barrier of primates may be more easily penetrated than that of rodents, which is compatible with the inventors' recent findings [Tomkins, O. et al. (2001) Cell Mol Neurobiol 21: 675-691].

The antisense agent targeted toward the human ACHE sequence (see Examples) appeared effective in Cynomolgus monkeys at the same nanomolar dose as that of the corresponding agents in mice [Cohen et al. (2002) id ibid.] and rats [Brenner et al. (2003) id ibid]. Long-term AChE-R overproduction, as is the case in head-injured mice, is associated with impaired locomotion control that is susceptible to improvement under antisense suppression of AChE-R production [Shohami (2000) id ibid]. In spite of the limited number of experimented animals used in the current study, delivery was appeared to be effective in both the intravenous and the oral administration mode, with dose dependence reflected by the more pronounced effects under 600 as compared to 150 µg/kg/day of orally administrated hEN101.

In conclusion, the present invention teaches methods of treatment of conditions wherein lowering the amounts of circulating AChE-R may be therapeutic and even preventive. Mainly, said conditions may be summarized as conditions triggering an inflammatory response, inflammation of any kind, and in particular inflammation-associated neuropathies, such as Guillain-Barre syndrome. The method comprises administering a therapeutically effective amount of an inhibitor of AChE expression or a composition comprising the same to a mammalian subject in need, preferably a human.

Preferably, said inhibitor of AChE expression to be used in the methods of the invention is an antisense oligonucleotide, which, more preferably has the sequence as denoted by any one of SEQ ID NO:1 and SEQ ID NO:7.

Said therapeutic effective amount, or dosing, is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$, found to be effective in in vitro as well as in in vivo.

The variant specificity, low dose and long duration efficacy of the antisense agents may be clear advantages over conservative drugs, both for interfering with acute stress-induced symptoms and inflammatory response, and hence for prevention of neurodeterioration. These considerations may be relevant to various disease conditions, including amyotrophic lateral sclerosis [Shaw, P. J. and Eggett, C. J. (2000) J. Neurol. 247 Suppl 1: 117-27], myasthenic syndromes [Becker et al. (1992) id ibid.], muscular dystrophy [Cifuentes-Diaz, C. et al. (2001) J. Cell Biol. 152: 1107-1114], spinal muscular atrophy [Sendtner, M. (2001) Curr. Opin. Neurol. 14: 629-634], and sepsis-mediated critical illness polyneuropathy [Hund, E. (2001) J. Neurol. 248: 929-934]. Antisense facilitation of the cholinergic attenuation of inflammatory responses in primate CNS neurons may thus offer interesting therapeutic advantages.

The methods described herein also include combination therapy, where the inhibitor of AChE expression or the composition comprising thereof are administered in combination with other drugs, in accordance with the condition of the subject to be treated.

As shown in Examples 6-11, administration of a low dose of endotoxin to healthy volunteers induces secretion of pro-inflammatory cytokines and cortisol, compromises cholinergic homeostasis and alters memory. Both psychological [Maes M. et al. (1998) Cytokine 10:313-8], and physical [Goodman J. C. et al. (1990) J. Neuroimmunol. 30:213-7] stressors are likewise associated with the production of pro-inflammatory cytokines (including TNF-α and IL-6) in humans. Exposure to stressful stimuli exerts profound effects on cholinergic homeostasis in general and on the production and cellular distribution of AChE-R in particular. Therefore, experimental endotoxemia emerges as a valid model for studying the interactions between cytokines and the changes in cholinergic homeostasis (as those are reflected by AChE-R modulations) as well as the impact of these interactions on memory functions. No subjective feelings of illness were involved, so that the endotoxin-induced memory alterations could not be attributed to a perceived physical-illness-associated distress. The selectivity of the observed memory changes was compatible with reports by others that cortisol does not affect attention, verbal executive function or vigilance [Lupien et al. (1999) Rev. Neurosci. 10: 117-39].

FIG. 11 presents a scheme summarizing the kinetic follow-up for the different parameters that were measured and the postulated associations between them, predicting potentially causal relationships between the induction of cytokines, hormone secretion, AChE modulations and the resultant memory changes. Interestingly, during the first testing period the endotoxin-induced impairment in declarative memory was highest and correlated positively with cytokine secretion, whereas the improvement in working memory became prominent at 3 hr post-treatment and showed no correlation with cytokine secretion. In contrast, both types of memory changes were significantly correlated with AChE-R cleavage, although cholinergic control over working memory seemed to begin earlier than for declarative memory (3 hr vs. 9 hr post-injection, FIG. 11B and FIG. 11C, respectively).

Previous reports have documented decrements in declarative memory following endotoxin administration to healthy volunteers [Reichenberg (2001) id ibid.], as well as following cytokine (especially interferon and interleukin-2) therapy [Meyers C. A. (1999) Adv. Exp. Med. Biol. 461:75-81; Capuron L. et al. (2001) Psychosom. Med. 63:376-86], viral (e.g., influenza) infection [Capuron (1999) id ibid.] or cortisol administration [de Quervain, D. J. et al. (2000) Nat. Neurosci. 3:313-4]. In this study, the endotoxin-induced decrease in declarative memory performance was associated with cytokines secretion only in the first testing period. In contrast, it was associated with AChE activity and AChE-R cleavage levels during the last period, when cytokine concentrations have returned to baseline yet the differences between AChE activity and AChE-R cleavage were maximal between the endotoxin and the placebo conditions. These findings may suggest that immune-mediated processes are prominent in the early endotoxin-induced memory impairments, whereas the later effects are probably mediated by the cholinergic system.

This study demonstrates that changes in memory functioning following endotoxin exposure are co-associated with the induction of pro-inflammatory cytokines and AChE-R cleavage. The tentative pathway through which these changes may occur involves alterations in cholinergic neurotransmission and elevation in cytokine secretion (FIG. 11). These are associated with many medical conditions that involve inflammatory processes, particularly within the brain (e.g., stroke, brain trauma and neurodegenerative disease, such as vascular dementia) [McGeer P. L. and McGeer E. G. (1995) *Brain Res. Rev.* 21:195-218; Saito H. et al. (1995) *Brain. Exp. Pharmacol. Physiol. Suppl.* 22:S257-9; Levin and Simon (1998) id ibid]. For example, closed head injury results in the production of TNF-α and other pro-inflammatory cytokines [Goodman et al. (1990) id ibid.; Trembovler V. et al. (1999) *J. Interferon Cytokine Res.* 19:791-5] as well as in excessive accumulation of AChE-R within the brain [Shohami et al. (2000) id ibid]. The findings presented herein suggest that cytokine-cholinergic interactions play an important role in the memory alterations that accompany these conditions, and may provide insights into the development of novel preventive and therapeutic procedures that will counteract the corresponding memory impairments without harming the improved capacities.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Example A

Preclinical Studies of hEN101 for the Treatment of Inflammatory Bowel Disease

The safety of hEN101, (as denoted by SEQ ID NO:7) was demonstrated in a series of toxicology studies, including acute single dose in mice, single and repeated dose in rats, repeated dose in primates, genetic toxicity and safety pharmacology studies by oral and intravenous (i.v.) administration. The maximal orally tolerated dose of hEN101, in both rats and primates, was considered to be >1000 mg/kg/day. This dose is 484 and 242 fold higher than the highest dose proposed for testing in human 40 mg/day), on a human equivalent dose (HED) basis for primates and rats, respectively.

The efficacy of hEN101 was then studied in TNBS-induced mice (mice treated by 2,4,6-trinitrobenzene sulfonic acid), which represent an experimental model for human Inflammatory Bowel Disease (IBD). Treatment was administered orally, once a day, to TNBS-induced mice and included hEN101 (10, 25 and 50 ng/kg), dexamethasone (100 µg/kg) and saline. Both prophylactic (one day before inducing colitis) as well as therapeutic (one or two days after inducing colitis) regimens of hEN101 at 25 and 50 µg/kg reduced the disease score to an extent similar to that of dexamethasone (100 µg/kg). When hEN101 was administrated to these mice, the colitis severity, assessed by the Wallace score, decreased by 80% compared to control.

Example B

Phase IIa Clinical Trial in Patients with Moderately Active Ulcerative Colitis

In order to evaluate the efficacy, pharmacodynamics, safety and tolerability of oral administration of hEN101, an open-label Phase IIa clinical study was (and is still) conducted in patients with moderately active ulcerative colitis, using the Mayo score (see Table 2 below), partial Mayo score (see Table 3 below), as well as endoscopic sub-score and inflammatory bowel disease (IBD) quality of life (QOL) score, as detailed below.

The study was approved by the Ministry of Health, and is conducted in four leading inflammatory bowel disease (IBD) centers in Israel, among which are the Shaare Zedek Hospital, Jerusalem; Rambam Hospital, Haifa; Sourasky Medical Center, Tel Aviv; and the Hadassah Medical Center, Jerusalem.

Selection of Patients

Patients (male or female at the age 18 to 70) were selected according to the following criteria: patients with moderately active ulcerative colitis as defined by Mayo score of ≤5 and ≤9 within 9 days of baseline, that were diagnosed for ulcerative colitis≥3 months prior to study entry, with endoscopic sub-score of ≥2 and rectal bleeding sub-score of ≥1 on the Mayo score and endoscopic evidence of disease activity a minimum of 20 cm from the anal verge, determined within 9 days of first day of study treatment. Additional criteria included non-receiving concomitant ulcerative colitis therapies, with the exception of 5-aminosalycilic acid at a stable dose for at least 2 weeks, prior to the first day of study and steroids at a dose equal to or lower than 10 mg/day, at a stable dose for at least 2 weeks prior to the first day of study treatment.

Exclusion criteria included diagnosis of indeterminate colitis or clinical findings suggestive of Crohn's disease, subjects with ulcerative proctitis (distal 20 cm or less), diagnosis of ischemic colitis, fulminant colitis or toxic megacolon, evidence of bowel infection and others.

Of the 13 patients enrolled, 6 patients completed the study, and their results are shown in Table 2 below.

The Mayo Score and Partial Mayo Score

The Mayo score (ranges from 0-12) was assessed at the screening visit and last treatment visit (Day 34±1) according to the following parameters:

TABLE 2

The Mayo score

Stool frequency (subscore 0-3)

| | |
|---|---|
| 0 = | Normal number of stools for patient |
| 1 = | 1 to 2 stools per day more than normal |
| 2 = | 3 to 4 stools more than normal |
| 3 = | >=5 stools more than normal |

Rectal bleeding (subscore 0-3)

| | |
|---|---|
| 0 = | No blood seen |
| 1 = | Streaks of blood with stool less than half the time |

TABLE 2-continued

The Mayo score

| | |
|---|---|
| 2 = | Obvious blood with stool most of the time |
| 3 = | Blood alone passes |

Endoscopic findings (subscore 0-3)

| | |
|---|---|
| 0 = | Normal or inactive disease |
| 1 = | Mild Disease |
| | (erythema, decreased vascular pattern, mild friability) |
| 2 = | Moderate Disease |
| | (marked erythema, lack of vascular pattern, friability erosions) |
| 3 = | Severe Disease (spontaneous bleeding, ulceration) |

Physician's Global Assessment (subscore 0-3)

| | |
|---|---|
| 0 = | Normal |
| 1 = | Mild disease |
| 2 = | Moderate disease |
| 3 = | Severe disease |

The partial Mayo score was assessed on Days 1 and 21±1 and at follow-up and inferred from the Mayo score (by subtracting the endoscopic sub-score) during the screening period and on Day 34±1. The partial Mayo score (ranges from 0-9) was assessed according to the following parameters:

TABLE 3

The partial Mayo score

Stool frequency (subscore 0-3)

| | |
|---|---|
| 0 = | Normal number of stools for patient |
| 1 = | 1 to 2 stools per day more than normal |
| 2 = | 3 to 4 stools more than normal |
| 3 = | >=5 stools more than normal |

Rectal bleeding (subscore 0-3)

| | |
|---|---|
| 0 = | No blood seen |
| 1 = | Streaks of blood with stool less than half the time |
| 2 = | Obvious blood with stool most of the time |
| 3 = | Blood alone passes |

Physician's Global Assessment (subscore 0-3)

| | |
|---|---|
| 0 = | Normal |
| 1 = | Mild disease |
| 2 = | Moderate disease |
| 3 = | Severe disease |

Treatment

Treatment comprised a pre-treatment screening period of 1-9 days, next patients were orally administered with 12 mg/day hEN101 for 19-21 days, followed by 40 mg/day hEN101 oral administration for 14 days.

Results

Phase 1 Safety Results

Adverse events (AE), such as moderate fever, were generally mild and transient and resolved shortly after occurrence without treatment or need to discontinue study medication. There were no clinically significant changes in vital signs, hematology, chemistry, urinalysis, ECG parameters or physical exams in any of the patients during the treatment phase or the 4 week follow-up period.

Clinical Results

A positive clinical response was defined by at least a 3-point decrease and 30% reduction from baseline in Mayo score, plus a≥1-point decrease in rectal bleeding sub-score or an absolute rectal bleeding sub-score of ≤1. As shown in Table 4 below, 7 patients having the baseline Mayo score of 6-9 completed the study (screening, treatment and follow-up). By the end of the study, in 6 out of 7 patients there was at least 50% reduction in Mayo score. Remarkably, in 3 of the 7 patients there was a reduction of over 60% in Mayo score (i.e. 62.5% and 66% reduction).

In addition, by the end of the study all patients demonstrated a reduction in stool frequency as compared to their baseline. The treatment also resulted in general reductions in rectal bleeding and endoscopic findings. All patients exhibited stable or a reduction in disease severity as assessed by a physician.

TABLE 4

Phase IIa clinical trial results

| Patient # | Mayo Score [Baseline] | Mayo Score [Completion] | Reduction points | % |
|---|---|---|---|---|
| 1 | 9 | 3 | 6 | 66% |
| 2 | 8 | 3 | 5 | 62.5% |
| 3 | 8 | 4 | 4 | 50% |
| 4 | 8 | 4 | 4 | 50% |
| 5 | 8 | 3 | 5 | 62.5% |
| 6 | 6 | 3 | 3 | 50% |
| 7 | 8 | 8 | — | — |

Additional Examples

The basic working hypothesis guiding this study was that stimulus-induced modulations in the levels and composition of neuronal AChE variants, ChAT and VAChT together contribute toward the maintenance of cholinergic homeostasis in primate motoneurons. This predicted neuronal AChE-R overproduction as well as ChAT and VAChT suppression also under mild stress (e.g. handling or injection). To test this hypothesis, the inventors measured plasma AChE activities and labeled AChE-R mRNA, ChAT and VAChT in lumbar spinal cord sections of cynomolgus monkeys with and without treatment with hEN101. There was no indication of change in the motor functioning of hEN101-treated monkeys following daily administration of nanomolar doses of hEN101 for one week, as assessed by general follow-up of motor behavior, clinical signs or electrocardiography. No treatment-related toxicity or inflammatory effect was observed in white blood cell (WBC) counts or post-mortem, suggesting that the modulations induced by this oligonucleotide reflected solely the consequences of its antisense effect and indicating general maintenance of cholinergic balance under such effects. Because of its specificity towards AChE-R mRNA, the inventors predicted that hEN101 would alter the level and/or composition of peripheral AChE. The inventors further examined whether AChE, ChAT and VAChT levels in motoneurons are changed under handling stresses and, if so, whether antisense suppression of AChE-R would attenuate neuronal IL-1β accumulation. General methods and materials described herein also apply to the above Examples A and B.

Experimental Procedures

Experimental Procedures Employed in Studying the Anti-Inflammatory Effects of hEN101 in the Primate Spinal Cord.

Animals:

15 month-old purpose-bred cynomolgus monkeys were supplied by Charles River (UK) Ltd. Antisense administration was performed at Huntingdon Life Sciences Ltd. (Huntingdon, UK), in compliance with all of the relevant regulations for animal experimentation in the UK.

Test Substance:

Human (h) HPLC-purified, GLP grade EN101 (purity 95% as verified by capillary electrophoresis) was purchased from Avecia Biotechnology (Milford, Mass.). The primary hEN101 sequence, 5'CTGCCACGTTCTCCTGCA*C*C*3'

(SEQ ID NO:1), is complementary to the coding sequence of human AChE mRNA (GeneBank Accession No. NM 000665, nucleotide positions 733-752) within exon 2, common to all three AChE variants [Soreq, H. and Zakut, H. (1993) *Human cholinesterases and anticholinesterases*, Academic Press, INC. San Diego; Ben Aziz-Aloya, R. et al. (1993) *Proc. Natl. Acad. Sci. U.S.A.* 90, 2471-2475]. The three 3'-terminal residues (*) were protected against nuclease attack with oxymethyl groups at the 2' position. The sequence representing hEN101 with the three 3'-terminal bases modified is denoted by SEQ ID NO:7. Lyophilized oligonucleotides were resuspended in sterile double distilled water (24 mg/ml), and stored at −20° C.

Several modes of chemical protection for antisense agents are currently being clinically tried in human studies [for recent review see Opalinska, J. B. and Gewirtz, A.M. (2002) *Nat. Rev. Drug Discov.* 1: 503-514]. The chemical protection protocol used in the current study (namely, three 3'-terminal 2'-Oxymethyl groups) combines maintenance of the oligonucleotide's capacity to recruit RNase H to its unprotected part while tightening the hybridization bonds through the 2'-O-methyl groups [Soreq and Seidman (2001) id ibid.], and offering improved intestinal permeability [Geary, R. S. et al. (2001) *J. Pharmacol. Exp. Ther.* 296: 890-7]. An additional benefit of this protection scheme is that removal of the protected 3' end will leave behind a naked and hence vulnerable oligonucleotide that will be rapidly degraded. Unlike other AS-ONs [Bennett, C. F. (2002) *Antisense Nucleic Acid Drug Dev.* 12: 215-224; Braasch, D. A. and Corey, D. R. (2002) *Biochemistry* 41: 4503-4510; Sazani, P. et al. (2002) *Nat. Biotechnol.* 20: 1228-1233] gradual nucleolytic breakdown would not lead in this case, to non-specific interactions, of shortened ON agents.

hEN101 Stability:

Stability of freeze-dried hEN101 was tested by HPLC during storage at −20±5° C., 4° C. and 25±2° C. (60±5% relative humidity) in the dark. Three samples from each storage condition were collected after 3, 6 and 9 months and their stability analyzed by HPLC. hEN101 was found to be stable for at least 6 months at −20° C. under these storage conditions.

hEN101 Administration:

Three pairs of 1.5 to 2.5 Kg cynomolgus monkeys, 1 male and 1 female, were administered hEN101 for 7 days: 150 µg/kg daily per os (p.o.) by oral gavage (15 µg/ml in 0.9% saline) or 500 µg/kg daily (p.o., 50 µg/ml in saline) or by intravenous (i.v.) injection (100 µg/ml in saline). Plasma samples were removed at the noted hours following the second day of treatment and kept at −20° C. until use. Following 1 week of daily treatment, animals were euthanized and lumbar spinal cord preparations were paraffin-embedded by standard procedures. One male naive monkey served as control.

Toxicology:

Potential toxicity of hEN101 was tested at Huntingdon before, during and following treatment. Among the parameters noted were body weight, food consumption, general locomotor behavior, electrocardiography and blood pressure, blood count, prothrombin time and standard blood chemistry (Hitachi 917 Clinical Chemistry Analyzer). Post-mortem observation included organ weights and scanning of hematoxylin and eosin-stained sections of brain, heart, kidneys, liver, lungs, spinal cord and stomach.

In Situ Hybridization:

Tissues were fixed in 4% paraformaldehyde and cut into 7 µm paraffin-embedded sections. Lumbar spinal cord sections were deparaffinized, rehydrated using serial ethanol dilutions and permeabilized with proteinase K (10 µg/ml, 10 min at 37° C.). Slides were exposed to 5' biotinylated, fully 2'-oxymethylated AChE-R or AChE-S-specific 50-mer cRNA probes complementary to human ACHE pseudointron 4 or exon 6, respectively (Microsynth, Belgach, Switzerland). The following probes were employed:

human AChE-R probe (nucleotide positions
88-38 in GenBank Accession No. S 71129;
SEQ ID NO: 5):
5'-CUAGGGGGAGAAGAGAGGGGUUACACUGGCGGGCUCCCACUCCCCU

CCUC-3;

human AChE-S probe (nucleotide positions
2071-2022 in GenBank Accession No.
NM 000665; SEQ ID NO: 6):
5'-CCGGGGGACGUCGGGGUGGGGUGGGGAUGGGCAGAGUCUGGGGCUC

GUCU-3'.

Hybridization was performed overnight at 52° C. in hybridization mixture containing 10 µg/ml probe, 50 µg/ml yeast tRNA, 50 µg/ml heparin and 50% formamide in 375 mM Na chloride, 37.5 mM Na citrate, pH 4.5. Slides were washed to remove unhybridized probe, blocked with 1% skim milk containing 0.01% Tween-20 and 2 mM levsmisol, an alkaline phosphatase inhibitor used to suppress non-specific staining and incubated with streptavidin-alkaline phosphatase (Amersham Pharmacia, Little Chalfont Bucks, UK). Fast Red™ substrate (Roche Diagnostics, Mannheim, Germany) was used for detection.

Immunohistochemistry:

Re-hydrated spinal cord sections were subjected to heat-induced antigen retrieval by microwave treatment in 0.01 M citrate buffer, pH 6.0. Non-specific binding was blocked by 4% naive goat or donkey serum in PBS with 0.3% Triton X-100 and 0.05% Tween20™. Slides were incubated with primary antibodies diluted in the same buffer (1 h, room temp., overnight, 4° C.). Sections were rinsed and incubated with biotin-conjugated secondary antibody, diluted (1:200) in the same blocking buffer (3 h, room temp.). The primary antibodies included rabbit polyclonal anti-VAChT (1:100, Sigma, St. Louis, Mo.), goat polyclonal anti-ChAT (1:50, Chemicon International, Temecula, Calif.) and goat anti-IL-1β (1:20, R and D systems, Minneapolis, Minn.). Biotinylated secondary antibodies were donkey anti-rabbit (Chemicon) and donkey anti-goat (Jackson ImmunoResearch Laboratories, West Grove, Pa.), both used at 1:200 dilutions. Detection was with Fast Red™ substrate for anti-VAChT and ChAT antibodies and with Vectastain ABC peroxidase kit (Vector Laboratories, Burlingame, Calif.) for the anti-IL-1β antibody.

Confocal Microscopy:

Confocal microscopy was carried out using a Bio-Rad MRC 1024 confocal scanhead (Hemel Hempsted, Hertfordshire, U.K.) coupled to an inverted Zeiss Axiovert 135 microscope (Oberkochen, Germany) equipped with a Plan Apochromat 40×1.3 immersion objective. Fast Red was excited at 488 nm and emission was measured through a 580df32 interference filter (580±16 nm). Immunolabeled sections were scanned every 0.5 µm and projections analyzed using the Image Pro Plus 4.0 (Media Cybernetics, Silver Spring, Md.) software.

Cholinesterase Activity Measurements:

Plasma samples were subjected to cholinesterase catalytic activity measurements [Ellman, G. L. et al. (1961) *Biochem. Pharmacol.* 7, 88-99] adapted to a multi-well plate reader. Acetylthiocholine (ATCh) hydrolysis rates were measured following prior incubation for 30 min with $5 \times 10^{-5}$M of the specific butyrylcholinesterase (BuChE) inhibitor tetraisopropylpyrophosphoramide, iso-OMPA. Total plasma cholinesterase activities were measured in the absence of inhibitors.

Experimental Procedures Employed in Studying the Relationship Between AChE-R, Cytokines and Memory Subjects of the Memory Study:

Ten male subjects participated in the study, which was approved by an independent ethics committee. Subjects recruitment as well as physical and psychiatric screening, were described in detail elsewhere [Reichenberg A. et al. (2001) id ibid]. The current study involved a subset of the subjects included in the previous project, with serum AChE and working memory tests added. Interviews by experienced psychiatrists excluded the presence and the history of any axis I psychiatric disorder according to the DSM-IV [American Psychiatric Association (1994) *Diagnostic and statistical manual for mental disorders*, 4th ed. Washington D.C.]. Only subjects who successfully passed the screening procedure, and signed an informed consent form, were considered eligible to participate. Comprehensive assessment was performed, and involved each subject going through a number of physical and neuropsychological tests in a clinical research unit using a balanced, randomized, double-blind, cross-over design.

Procedure for the Memory Tests:

All technical equipment, including the blood sampling device, was housed in a room adjacent to the sound-shielded experimental room. Every subject passed two 10 days apart testing sessions and spent the night before each experimental session in the research unit. A battery of neuropsychological tests, assessing memory, learning, and attention was given for adaptation upon their first arrival in the evening, minimizing subsequent practice effects [McCaffrey, R. J. and Lynch, J. K. (1992) *Neuropsychol. Rev.* 3:235-48]. Alternate versions of these tests were used in the experimental testing sessions. In the next morning, an intravenous cannula was inserted into an antecubital forearm vein for intermittent blood sampling and intravenous (i.v.) injection of endotoxin (0.8 ng *Salmonella abortus* equi endotoxin per Kg body weight) in one session or the same volume of 0.9% NaCl (saline) solution on the other occasion (placebo). The order of injections was balanced, so that half of the subjects received the saline injection and half received the endotoxin injection first. No significant differences were found between the groups defined by the treatment order in either age, years of education, or body weight. The experimenter and the subject were blind with respect to the group assignment. During each session, subjects were tested three times, at 1-2, 3-4 and 9-10 hr post-injection. Blood was collected at baseline before i.v. injection, and at the beginning of each testing period. Rectal temperature was measured continuously using a thermistor probe. Self-reported physical sickness symptoms (headaches, muscle pain, shivering, nausea, breathing difficulties, and fatigue) were assessed at the end of each testing period, by a questionnaire using a 5-point Leikart scale (O-no symptoms, 4-very severe symptoms).

*Salmonella abortus* equi Endotoxin:

Prepared for use in humans, this endotoxin was available as a sterile solution free of proteins and nucleic acids. The endotoxin preparation employed has proven to be safe in various studies of other groups [Burrell R. (1994) id ibid.] and in studies at the Max Planck Institute of Psychiatry, including more than 100 subjects since 1991 [Pollmacher T. et al. (1996) *J. Infect. Dis.* 174:1040-5].

Plasma levels of AChE and its degradation product, cytokines and cortisol: Blood was collected in tubes containing Na-EDTA and aprotinin and was immediately centrifuged. Plasma was aliquoted and frozen to −80° C. AChE catalytic activity was measured as the capacity for acetylthiocholine (ATCh) hydrolysis in the presence of $1\times10^{-5}$ M tetraisopropylpyrophosphoramidate (iso-OMPA), a selective inhibitor of serum butyrylcholinesterase, BChE [Soreq H. and Glick D. (2000): Novel roles for cholinesterases in stress and inhibitor responses. In: Giacobini E. (ed.) *Cholinesterases and Cholinesterase Inhibitors: Basic, Preclinical and Clinical Aspects*. London, Martin Dunitz, pp 47-61]. Endotoxin-induced differences were calculated by subtracting activities in the absence of endotoxin, with each individual serving as its own control and daily hour carefully matched. To evaluate AChE-R concentrations and integrity, plasma proteins (40 μg) were subjected to 4-20% polyacrylamide gel electrophoresis under fully denaturing conditions (BioRad Laboratories, Hercules, Calif.), blotted to nitrocellulose filters, incubated with rabbit anti-AChE-R antibodies [Sternfeld M. et al. (2000) *Proc. Natl. Acad. Sci. USA* 97:8647-8652] and peroxidase-conjugated anti-rabbit immunoglobulins, and subjected to ECL™ detection (Amersham Pharmacia Biotech, UK), densitometric analysis and quantification as described [Shohami (2000) id ibid]. The plasma levels of cortisol were determined by a radioimmunoassay, and the plasma levels of cytokines and soluble cytokine receptors were assessed by commercial enzyme-linked immunoabsorbent assays [Mullington J. et al. (2000) *Am. J. Physiol. Regul. Integr. Comp. Physiol.* 278:R947-55]. Labeling AChE-R mRNA and its protein product in vascular endothelial cells: Fluorescent in situ hybridization and immunohistochemistry of AChE-R mRNA and AChE-R protein were performed and quantified as reported [Cohen (2002) id ibid.; Perry, C. et al. (2002) *Oncogene* 21:8428-8441] using paraffin-embedded tissue sections from surgically-removed biopsies of patients with or without clinical inflammation due to non-specific kidney vasculitis or following kidney rejection.

MALDI-TOF-MS Analysis of Immunolabeled Proteins:

Matrix-assisted laser desorption/ionization time-of-flight mass spectrometry (MALDI-TOF-MS) was employed in an attempt to identify the protein and peptide bands labeled by anti-AChE-R antibodies in blotted membranes. Proteolytic degradation of the gel-eluted peptide was performed using the endoprotease LysC from Achromobacterlyticus (Wako Chemicals, Inc., USA) at a substrate to enzyme ratio of 200:1. Digestion was carried out overnight in 0.05M Tris HCl, pH 9.0, in the presence of 4M urea, at 30° C.

Neuropsychological Assessment:

Declarative memory was assessed using the Story Recall test [Green P. and Allen L. M. (1995): *Manual for the CogniSyst Story Recall test* CogniSyst Inc., Durham, N.C.]. Subjects were requested to repeat a 25-item story from memory immediately, and 30 min after presentation. The total number of correct verbatim recall was counted. Memory span and working memory were assessed using the Digit Span forward and backward [Wechsler D. (1987): *Wechsler Memory Scale, Revised Manual* The Psychological Corp, San Antonio, Tex]. Subjects were requested to repeat lists of digits with increased number of digits every two lists either in the correct order of presentation (forward condition-assessment of span), or in a reversed order (backward condition-assessment of working memory). The number of lists correctly repeated was counted. Attention was assessed using the Ruff 2 and 7 cancellation test [Ruff R. M. and Allen C. C. (1996): *Ruff 2 and 7 Selective Attention Test: Professional Manual*. Psychological Assessment Resources Inc., Lutz, Fla.]: Subjects were instructed to mark either the digit 2 or the digit 7, which are randomly placed either between letters or between digits. The numbers of correct responses in a 5 minute trial were counted.

Statistical Analyses:

The main hypotheses concerning treatment effects on AChE activity, AChE-R levels, and neuropsychological performance were tested using repeated measure analysis of variance models (ANOVAs). Repeated measure ANOVAs were also used to examine the treatment effect on physical sickness symptoms, on plasma levels of cytokines and cortisol and on body temperature. The level of significance was set at the critical value of p=0.05 (two tailed). Whenever significant treatment-by-time interactions were found, the simple effects were analyzed as suggested [Winer B. et al. (1991): *Statistical Principles in Experimental Design,* 3rd ed. McGraw-Hill, New York], and Tukey's adjustments were applied.

To assess the associations between changes from the placebo to the endotoxin condition in AChE activity, AChE-R levels, and physiological (cytokines and cortisol secretion), and neuropsychological parameters, Pearson's correlation coefficients were calculated. No deviation from normal distributions was evident for any of the dependent variables. No univariate outliers were found using Z-scores and no multivariate outliers were found using the Mahalanobis distance [Tabachnick B. G. and Fidell L. S. (2001) *Using Multivariate Statistics,* 4th ed. Allyn and Bacon, Boston, Mass]. To adjust for any non-homogeneity of covariance for the within-subject effects, we used p values that were adjusted using the Huynh-Feldt method [Norusis M. J. (1994) *SPSS advanced statistics* 6.1. SPSS Inc., Chicago, Ill]. Analyses were carried out using SPSS 10.

Linear rank Wilcoxon test for two related samples was used for the analysis of AChE-R- and IL-1β-positive fractions of analyzed neurons, measured on at least 4 sections from each group. Differences were considered significant when a p value of ~0.05 or less was obtained using the SAS 8.0 software. Student's t test was used for analyzing the numbers and volume of VAChT-containing terminals in spinal cord sections. Experimental Procedures Employed with the GBS Model Pre-Treatment, Sensitization and LPS Exposure:

Systemic *Campylobacter* or *E. Coli* LPS exposure was done as previously described [Ifergane G. et al. (2003) *J. Neural. Sci.* 213: 11-14]: Female 8-week-old Lewis rats were sensitized with 100 g KLH by subcutaneous (s.c.) injections administered to the base of tail on days 1 and 21 followed by intraperitoneal injection of 15 microgram Cj 0:19 or *E. Coli* 055:B5 LPS on day 28. In vitro LPS exposure: Lewis rats were similarly sensitized with KLH. On day 28, the rats were sacrificed, their spleens removed and disintegrated into cell suspension. The cells were suspended in RPMI-1640 medium containing antibiotics and glutamine. Following centrifugation, the pellet was resuspended in RPMI, layered on Histopaque and centrifuged again. The lymphocyte fraction was collected, washed and supplemented with fetal calf serum and diluted to a concentration of $1.4 \times 10^7$ cells/ml. Splenocytes reacted with LPS additionally contained 0.5 µg/ml Cj-LPS. Following incubation for 48 hour at 37° C. with 5% $CO_2$, the cell suspension was centrifuged and supernatant medium collected and stored at −20° C. until use.

Bone-Marrow Derived Macrophages (BMM):

Rat femur marrow content was obtained as described elsewhere [Apte, R. N., and Keisari, Y. (1987) *Immunobiology* 175: 470-481], dispersed into RPMI 1640 medium, washed, supplemented with serum and L-cell conditioned medium as a source of a colony stimulating factor and cultured at 37° C., 5% $CO^2$. After 7 days a macrophage monolayer was harvested.

Intraneural Injection:

Female 8-week-old Lewis rats were anesthetized by intraperitoneal injection of 10% solution of chloralhydrate (0.3-1 ml). The sciatic nerves exposed at the mid-thigh through a skin incision from the sciatic notch to the popliteal fossa. Tested mediums or solutions, 10 µl each, were intraneurally injected to separate sciatic nerves, via hand held Hamilton microsyringe with a 30½ gauge needle under a dissection microscope. Electrophysiological assessment was done as we previously described [Ifergane (2003) id ibid.]: Nerve conduction was performed prior to, 10 minutes, 1, 2, 3, 4 and 7 days following intraneural injection under general anesthesia by chloralhydrate solution of (0.3-1 ml) at room temperature. The sciatic nerve was supramaximally stimulated at the sciatic notch, and the peroneal and posterior tibial nerves at the ankle via needle electrodes. Compound muscle action potentials (CMAP) was recorded from the intrinsic foot muscles (both extensor digitorum brevis and flexor digitorum brevis). CMAPs, their baseline to peak amplitude, latency and duration were measured and the proximal and distal amplitudes ratio (PDR) calculated for each nerve. A PDR of less than 0.5 was considered a conduction block.

Tissue Preparations:

For western blot analysis, 7 µm of the sciatic nerve including the injection site were removed under general anesthesia as described, quickly frozen in liquid nitrogen, and stored at −70° C. For morphological analysis, the nerve segments were immersed in 4% paraformaldehyde in PBS (48 hrs, 4° C.), embedded in paraffin and sectioned at 8 µm in the axial or longitudinal planes.

In Situ Hybridization and Immunohistochemistry:

As previously reported [Dori A. et al. (2005) *Cereb Cortex* 15(4): 419-30], sections were deparaffinized, rehydrated and boiled in a microwave (750 W, 15 min) in 0.01M citric buffer (pH 6.0). Cy5-conjugated streptavidin and Cy3-conjugated anti-digoxygenin will be employed for detection of AChE-R mRNA specific biotin- and AChE-S mRNA specific digoxygenin-labeled probes, respectively. Cy3- or biotin-conjugated secondary IgG reacted with avidin-bound peroxidase-complex (ABC Elite, Vector Laboratories) will be applied for detection of primary antibodies by confocal or light microscopy following peroxidase reaction, respectively. Selected sections will be counterstained with Gill-2 hematoxyllin.

Image Analysis:

Confocal microscopy and Scion Image software (Scion Corporation, Frederick, Md.) will be applied as described [Dori (2005) id ibid.].

Immunoblots:

Nerve homogenates were produced by grounding with a pestle and mortar and processed as we previously described [Dori (2005) id ibid.].

Catalytic Activity:

Acetylthiocholine hydrolysis will be measured spectrophotometrically as described [Kaufer (1998) id ibid.], using Iso-OMPA (tetraisopropylpyrophosphoramide) to block butyrylcholinesterase activity (510-5 M).

Statistical Analysis:

ANOVA (Statistica software, StatSoft, Tulsa, Okla.) will be used to compare multiple groups and one-tailed t-test (Microsoft Excel) to compare two groups.

Example 1

Treatment-Reduced VAChT and ChAT Labeling in Spinal Cord Motoneurons

Figures 1A, 1B, 1C:
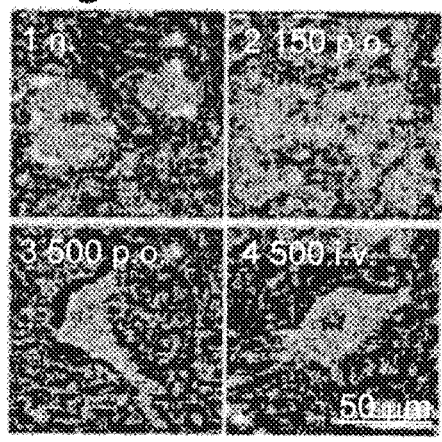
FIG. 1A-1F: Reduced VAChT Accumulation in Cholinergic Terminals and Partition Cells of Treated Monkeys.

VAChT was predictably concentrated in cholinergic (C) terminals surrounding motoneurons [Weihe (1996) id ibid.], where it loads neural vesicles with ACh. Confocal microscopy projections of spinal cord motoneurons (cell diameter=40 μm) from hEN 101-treated monkeys as compared with the naive state showed small but significant dose-independent decreases (p<0.01, Student's t test) in the average number of VAChT-positive C-terminals per cell (FIG. 1A, 1B), suggesting a handling stress effect on loading C-terminals with ACh. VACh-T-labeled C-terminals were significantly smaller (<60 μm$^3$) under p.o. administration of 150 μg/kg/day as compared to control sections (FIGS. 1B and 1C, p<0.01, Student's t test), perhaps reflecting changes in VAChT translocation into vesicles and/or VAChT stability.

Figure 1D:
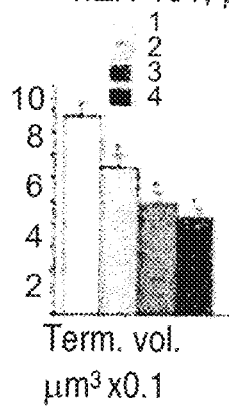
Figure 1E:
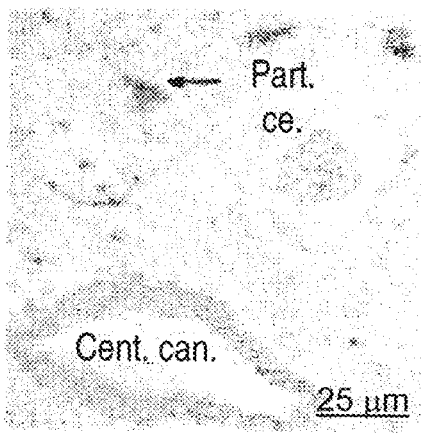
Figure 1F:
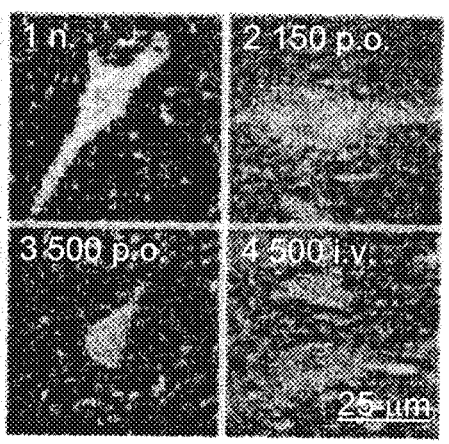

VAChT production is largely co-regulated with that of ChAT [Usdin, T. B. et al. (1995) *Trends Neurosci.* 18, 218-224], since both are produced from one gene complex (the so called "cholinergic locus") [Erickson, J. D. et al. (1996) *Prog. Brain Res.* 109, 69-82]. ChAT staining of C-terminals on motoneurons indeed presented similar changes to those observed for VAChT staining (data not shown). In addition, anti-ChAT antibodies labeled in control sections several partition cells (FIG. 1D), from which cholinergic terminals emerge to motoneurons [Barber, R. P. et al. (1984) *J. Comp. Neurol.* 229, 329-346]. Lumbar spinal cord sections from hEN101-treated monkeys, regardless of the dose or mode of administration, revealed conspicuously decreased staining intensity of ChAT-positive partition cells (FIG. 1E), again indicating handling stress-related suppression of ACh production and slowdown of vesicle recycling.

Example 2

EN101 Prevention of Stress-Induced Increases in Plasma AChE Activity

Cholinesterase activities were measured in plasma samples taken during the second day of hEN101 administration. ATCh hydrolysis in plasma is largely due to serum BuChE, the primary serum cholinesterase encoded by a non-homologous mRNA which remained generally unchanged. However, plasma also includes a minor, but significant AChE activity [Zakut, H. et al. (1998) *Cancer* 61, 727-737], measurable following pre-incubation in the presence of 5×10$^{-5}$M of the BuChE-specific inhibitor, iso-OMPA. AChE activity increased, as compared with the values before treatment (pre-dose), within the 5 hr following the stressful oral gavage administration of 150 μg/kg EN101 (Table 1), potentially reflecting increased production under handling. This further indicates a short half life for primate AChE-R mRNA in vivo, compatible with previous findings [Chan (1991) id ibid; Brenner et al. (2003) id ibid]. Increases were effectively suppressed by the higher oral dose of 500 μg/kg EN101, and yet more so following i.v. of administration of 500 μg/kg EN101 (Table 1), possibly reflecting dose-dependent hEN101 prevention of AChE-R synthesis.

TABLE 1 hEN101-induced prevention of treatment-associated increases in Plasma AChE activity[1]

| | hEN101 dose (μg/kg) | | |
|---|---|---|---|
| | 150 | 500 | 500 |
| hr post-treatment | | Mode of administration | |
| | p.o | p.o. | i.v. |
| Total ChE activity (% of pre-treatment[2]) | | | |
| 0 | 100 ± 1 | 100 ± 2 | 100 ± 1 |
| 3 | 92 ± 9 | 105 ± 1 | 89 ± 2 |
| 6 | 102 ± 3 | 96 ± 2 | 94 ± 1 |
| 12 | 98 ± 2 | 96 ± 1 | 93 ± 1 |
| AChE activity (% of pre-treatment[3]) | | | |
| 0 | 100 ± 4 | 100 ± 6 | 100 ± 4 |
| 3 | 117 ± 2 | 114 ± 6 | 105 ± 4 |
| 6 | 135 ± 1 | 100 ± 5 | 89 ± 5 |
| 12 | 123 ± 3 | 112 ± 4 | 94 ± 3 |

[1]Percent changes in the ATCh hydrolysis rates in plasma samples from monkeys treated twice on 2 consecutive days with the noted amounts and administration routes of hEN101.
[2]In the absence of inhibitors, hydrolysis rates reflect activity of the abundant cholinesterase in plasma, BChE.
[3]AChE specific activity, measured in the presence of 5 × 10$^{-5}$M of the specific BChE inhibitor, iso-OMPA. Values represent average ± SEM from six measurements in plasma samples derived from 2 monkeys. Mean AChE and BChE absolute activity.

Example 3

EN101 Effects on AChE-R and AChE-S mRNAs in Monkey Spinal Cord Neurons

Paraffin-embedded sections of lumbar spinal cord from Cynomolgus monkeys treated for 7 days once daily with hEN101 were subjected to high resolution fluorescent in situ hybridization (FISH). Variant-specific FISH probes (FIG. 2A) revealed AChE-S more than AChE-R mRNA labeling in numerous punctuate areas and longitudinal threads, possibly cross-sections and longitudinal sections through neuronal processes (FIG. 2B-2C). This difference, albeit statistically non-significant was compatible with previous observations demonstrating AChE-S, but not AChE-R mRNA in murine neuronal processes under normal conditions [Meshorer (2002) id ibid]. The higher oral and i.v. dose yielded reduced AChE-R mRNA labeling (FIGS. 2G and 2I as compared with the lower dose, FIG. 2E). AChE-S mRNA-labeled neurons displayed limited EN101-induced suppression (FIG. 2H, 2J as compared to 2D), with reduced process labeling (FIGS. 2F, 2H and 2J). Positron Emission Tomography (PET) imaging studies in Rhesus monkeys demonstrated for 2'-O-methylated oligonucleotides limited, yet relatively efficient penetrance to the brain as compared with phosphorothioate agents [Tavitian et al. (1998) id ibid]. In addition, the blood-brain-barrier of primates may be more easily penetrated than that of rodents [Tomkins et al. (2001) *Cell Mol. Neurobiol.* 21: 675-91]. Nevertheless, this is the first demonstration of an organismal antisense response that affects primate CNS neurons.

At the same nanomolar dose as that of the corresponding agents in mice [Cohen (2002) id ibid.], and rats [Brenner (2003) id ibid.], delivery of human EN101 appeared in Cynomolgus monkeys to be effective in both the intravenous and the oral administration mode, as it did in rats [Brenner (2003) id ibid]. Albeit in a limited number of animals, dose dependence was reflected by the more pronounced effects under 500 as compared to 150 μg/kg/day of orally administrated hEN101.

Example 4

Antisense Destruction of AChE-R mRNA is Inversely Related to Perikaryon Size Similarly sized neurons in hematoxylin-eosin stained spinal cord sections (FIG. 3A) were sorted into three size groups according to their cell body diameter (FIG. 3B): motoneurons (=40 μm, 20-35% of total counted neurons, localized to motor nuclei in the ventral horn and intermediate zone), medium-sized neurons (20-40 μm, about 60%, dispersed throughout the spinal cord, mainly in the ventral horn and intermediate zone), and small neurons (10-20 μm, 5-20%, located primarily in the dorsal horn). AChE-S and AChE-R mRNA labeled cell fractions from each group were evaluated in adjacent sections of small and medium sized AChE-R positive cells (<40 μm diameter) by over 4-fold as compared to the naive state ($p=0.057$ for small cells, Wilcoxon test).

AChE-R-positive smaller neuron fractions dropped significantly under the higher hEN101 oral dose ($p=0.033$, Wilcoxon test), compared to the 150 μg/kg/day treatment, and even further under its i.v. administration ($p=0.015$). Medium sized fractions dropped significantly following i.v. 150 μg/kg/day as compared to p.o. administration of 150 μg/kg/day ($p=0.030$). Reduced staining intensity suggested a certain antisense effect in motoneurons, as well, albeit with relatively limited efficacy. However, there was no discernable reduction in the total fractions of labeled large cell bodies by any treatment ($p>0.100$). This possibly reflects distinct membrane and/or metabolic properties, different cell volumes or a combined contribution of these properties. For AChE-S mRNA, the number of large positive cell bodies remained unchanged, whereas positive small and medium sized neurons, were reduced by 50% and 20%, respectively under either low or high dose of hEN101 as compared to naive. The apparent dose-independence of changes in AChE-S mRNA is compatible with the hypothesis that these changes were not antisense driven, but could possibly reflect the effect of handling stress of shifting splicing from AChE-S to AChE-R [Kaufer (1998) id ibid.].

Example 5 hEN101 Suppression of Neuronal Pro-Inflammatory Cytokines

Lumbar sections from hEN101-treated monkeys contained a higher fraction of both large and medium-sized IL-1β positive cell bodies than naive sections, suggesting stress-induced inflammatory response (FIG. 4A, $p=0.051$ and $0.034$ respectively, Wilcoxon test). Lower fractions of IL-1β labeled cell bodies were shown in sections from 500 μg/kg/day hEN101-i.v. as compared to 150 μg/kg/day p.o. treated monkeys (FIG. 4A, $p=0.067$ for both size groups, Wilcoxon test). Association analysis demonstrated a putative correlation between neuronal AChE-R and IL-1β levels in medium-sized, but nor large cells (FIG. 4B and data not shown). IL-6 labeling as well was suppressed significantly following i.v. administration of 500 μg/kg hEN101 (FIG. 4C, $p=0.03$ and $0.015$ for medium and large neurons, respectively) as compared to 500 μg/kg-p.o.-treated monkeys.

Example 6

Endotoxin Induces Impairments in AChE-R Activity and Integrity

Endotoxin administration produced a time-dependent decrease in plasma AChE activity, measured by quantifying the rate of ATCh hydrolysis in the presence of the butyrylcholinesterase (BChE) inhibitor iso-OMPA. This reduction displayed a significant treatment-by-time interaction (FIG. 5A) [$F(2,16)=3.94$, $p=0.04$]. Saline administration (placebo) caused no change in AChE activity, excluding the possibilities that it was induced by the injection stress or by circadian influences. The decline in hydrolytic activity could potentially reflect losses in the AChE protein. To test this possibility, electrophoretically separated plasma proteins were immune-reacted with antibodies selective for the C-terminal peptide unique to AChE-R [Steinfeld et al. (2000) id ibid]. These antibodies labeled a 66 kd protein, likely to be full-length AChE-R, as well as a shorter peptide with an apparent size of 6.5 kD. A parallel labeling pattern in the serum of stressed mice [Grisaru et al. (2001) id ibid.] raised the suggestion that this was an immunopositive C-terminus cleavage product of AChE-R. Endotoxin administration induced a slight, yet persistent, increase in the AChE-R cleavage product (FIG. 5B, 5C). This increase did not reach statistical significance [$F(1,8)=2.32$, $p=0.16$, for treatment effect] (FIG. 5C). However, at 9 hr post-treatment, the endotoxin-induced decrease in AChE activity was significantly correlated with endotoxin-induced increase in AChE-R cleavage ($r=-0.65$) (FIG. 5D).

Example 7

MALDI-TOF-MS Analysis of AChE-R Cleavage Product

To further characterize the AChE-R cleavage product, larger plasma samples (180 μg/lane) were resolved by electrophoresis. Protein bands that co-migrated with the bands labeled with anti AChE-R antibodies were cut out of the gel and subjected to MALDI-TOF-MS analyses. The elution product of the larger band was identified as being mainly composed of serum albumin (molecular weight, 69367), compatible with the assumption that AChE-R is only a minor component in this size fraction of human serum proteins. The shorter peptide eluted from the excised band, however, revealed a single peak with a molecular mass of 3613-3615. FIG. 6 demonstrates the MALDI-TOF-MS profile of this eluted peptide. Peptide property calculations positioned the presumed proteolytic cleavage site 36 residues from the C-terminus of AChE-R, with a calculated mass of 3614. Under these assumptions, cleavage could occur between asparagine and arginine residues upstream to the AChE-R diversion site (FIG. 6).

Parallel size peptides were observed in gel-eluted products from several individuals, demonstrating consistent cleavage processes. LysC proteolysis failed to further shorten this peptide. Edman degradation was unsuccessful, perhaps due to N-terminal blockade, and further experiments were prevented because of lack of material. The mass spectrometry approach thus pointed, although inconclusively, at an AChE-R cleavage site in human plasma under endotoxic stress near the C-terminal splice site that marks the deviation between human AChE splice isoforms.

Example 8

Vascular Endothelial Cells Produce AChE-R

In search for the potential cell type origin of plasma AChE-R, the inventors performed fluorescent in situ hybridization (FISH) and immunohistochemistry on human tissues from patients with or without inflammatory diseases (e.g. kidney vasculitis). Vascular endothelial cells displayed labeling with both AChE-R cRNA and anti AChE-R antibodies (FIG. 7A, 7B). Quantification of signal intensities revealed considerable similarities between AChE-R mRNA and AChE-R protein levels in patients with or without inflammatory vasculitis, so that tissues with less pronounced mRNA labeling also displayed fainter protein labeling (FIG. 7C). This pointed at vascular endothelial cells, which also harbor non-neuronal nicotinic acetylcholine receptors [Heeschen et al. (2002) J. Clin. Invest. 110:527-36] as a probable site of continuous plasma AChE-R production.

Example 9

AChE-R Cleavage is Associated with Cytokines Secretion

Endotoxin induced a transient, significant increase in the plasma levels of cortisol, TNF-α and IL-6 (FIG. 8A-8C), although at the employed dose it does not produce any significant effects on the subjective rating of physical or behavioral sickness symptoms [Reichenberg (2001) id ibid]. The selective increase in peripheral cytokine levels in the absence of subjective CNS effects on cognitive or intellectual function, suggested that changes in memory functions under these conditions would reflect objective endotoxin-induced alterations. Cortisol levels increased during the first and second testing periods, TNF-α and IL-6 peaked during the first testing period and decreased thereafter and rectal temperature (not shown) peaked during the second period. These time-dependent effects were reflected by significant treatment-by-time interactions [F(2,16)=41.2, 10.6, 10.5, 3.2, respectively, all p<0.05, by H-F].

At each testing period, correlation analysis enabled the comparison between the biochemical and functional responses of tested individuals. Thus, endotoxin-induced AChE-R cleavage (computed as the change in a certain individual from the endotoxin to the placebo condition) was significantly (p<0.05) and positively correlated with the secretion of cortisol, during the last testing period (r=0.70) (FIG. 8A). AChE-R cleavage was significantly (p<0.01) and negatively correlated with the secretion of TNF-α and IL-6 during the first (r=−0.72 and −0.66, respectively) (FIG. 8B, 8C), but not later testing periods.

Example 10

AChE-R Cleavage is Associated with Endotoxin-Induced Impairments in Declarative Memory Endotoxin administration decreased the performance in tests of declarative memory during all testing periods. This was reflected by decreased immediate recall of story items [F(1,8)=6.5, p=0.03] (FIG. 9A) and reduced delayed story recall [F(1,8)=3.5, p=0.09] (data not shown). Endotoxin-induced decrease in immediate and delayed recall of story items was significantly (p<0.05) and negatively associated with TNF-α and IL-6 secretion (r=−0.59 to −0.67) during the first, but not during other testing periods (data not shown), suggesting the potential involvement of additional mechanism(s) in endotoxin-induced impairments in declarative memory. At the last testing period, the endotoxin-induced decrease in immediate recall of story items was significantly (p<0.05) and negatively (r=−0.63) associated with AChE-R cleavage (FIG. 9B), indicating that the consequent increase in ACh levels, perhaps in conjunction with continuously suppressed cytokine production, interferes with declarative memory. This notion was supported by the positive (r=0.68) association of declarative memory impairments with the decrease in AChE activity during the last testing period (FIG. 9C), when cytokine levels already receded, but not during earlier testing periods.

Example 11

AChE-R Cleavage Association with Improved Working Memory

Endotoxin administration induced a significant improvement in working memory performance, reflected by an increased score in the digit span backward test during all testing periods [F(1,8)=12.3, p=0.008] (FIG. 10A). No significant changes in the digit span forward test (assessing memory span) or on the attention test (Ruff 2 and 7 cancellation test) were evident (data not shown), emphasizing the selectivity of the observed differences.

The endotoxin-induced improvement in working memory performance showed no significant association with the secretion of TNF-α, IL-6 or cortisol, yet was negatively associated with AChE-R cleavage. Association was significant (p<0.05) during the second and third testing periods (r=−0.84 and −0.64, respectively) (FIG. 10B and data not shown). Thus, subjects with a greater endotoxin-induced elevation in AChE-R cleavage (and, presumably, larger increases in ACh levels) showed both lower endotoxin-induced improvement in working memory functioning, and greater endotoxin-induced impairment in declarative memory.

Example 12

AChE-S Transgenic Mice Display Elevated Body Temperature

Fever is one of the consequences of higher levels of circulating pro-inflammatory cytokines. In order to verify whether the constitutive expression of human synaptic AChE (hAChE-S) [Beeri et al. (1995) id ibid.] and the consequent over-expression of murine AChE-R [Cohen et al. (2002) id ibid.] influenced the release of pro-inflammatory cytokines in the animal, the inventors measured body temperature. Five transgenic FVB/N hAChE-S and mAChE-R overexpressing females, 3-5 months old, had their temperature measured between 5 and 55 minutes after anesthesia, which was administered in order to induce a change in body temperature. As shown in the graph (FIG. 12A-B), body temperature decreased with post-treatment time. Interestingly, the average body temperature of the transgenic mice was always 2.0 higher than in the control mice. This suggests that their inherited cholinergic imbalance impaired their control over body temperature. These finding are compatible with the inventors' previous report of impaired hypothermic response of these transgenic mice to the administration of paraoxon [Beeri et al. (1995) id ibid.].

Example 13

Effects of Tacrine on LPS-Induced IL-1 Secretion in the Hippocampus and IL-1 and TNF-α Secretion in the Serum Male C57 mice were injected (i.p.) with either saline or tacrine (1.5 mg/kg), immediately followed by an injection of either saline or LPS (1.0 mg/kg) (n=5 animals per group).

Two hours later, mice were deeply anesthetized with 24 μg Nembutal per mouse, blood was taken by heart puncture and the hippocampus was excised and placed in tubes containing 500 μl of RPMI+100 KIU aprotinin. The levels of IL-1β in the hippocampus (FIG. 13A) and IL-113 (FIG. 13B) and TNF-α (FIG. 13C) in the serum were assessed with commercial ELISA kits (R and D Systems). LPS induced a significant increase in the hippocampal and serum IL-1β, which was significantly attenuated in tacrine-treated mice. In contrast, tacrine produced a small and non-significant attenuation of LPS-induced TNF-α secretion in the serum.

Example 14

Effects of Rivastigmine on LPS-Induced IL-1 Secretion in the Hippocampus and IL-1 and TNF-α Secretion in the Serum Male C57 mice were injected (i.p.) with either saline or one of three doses of rivastigmine (0.5, 1.5 and 3.0 mg/kg), immediately followed by an injection of either saline or LPS (1.0 mg/kg) (n=5 animals per group). Two hours later, mice were deeply anesthetized with 24 micro g Nembutal per mouse, blood was taken by heart puncture and the hippocampus was excised and placed in tubes containing 500 μl of RPMI+100 KIU aprotinin. The levels of IL-1β and TNF-α were assessed with commercial ELISA kits (R and D Systems). LPS induced a significant increase in the hippocampal IL-1β, which was significantly attenuated only by the high dose of rivastigmine (FIG. 14A). LPS-induced IL-1β secretion within the blood was dose-dependently suppressed by the 1.5 and 3.0 mg/kg doses of rivastigmine (FIG. 14B). LPS-induced TNF-α secretion in the blood was not affected by rivastigmine treatment, even at a high dose (FIG. 14C).

Example 15

Cytokines as Mediators of Emotional and Cognitive Effects of Stress Caused by Surgery Several lines of evidence indicate that stress influences a variety of cognitive functions, including memory. In particular, exposure to stress was found to impair declarative memory, while leaving procedural memory intact. It is also well known that stress influences many immune functions, including the production and secretion of cytokines. Following exposure to various stressors, there is an increase in peripheral IL-6, as well as IL-1β and TNFα, accompanied by decrease in IL-2, in both humans and experimental animals.

The study was designed to examine the role of cytokines in mediating the affective and cognitive effects of stress. Two types of stressful situations were investigated in the same subjects: Psychological stress-while waiting for a surgery (i.e., in the morning of the surgery day), and surgical stress-in the day after surgery.

Twenty generally healthy volunteers were administered with a comprehensive neuropsychological test battery, assessing emotional and cognitive parameters, before and after a minor surgery (Laparoscopic Cholecystectomy or Hernia). Each subject was tested in three occasions: (a) Several days before surgery (baseline)=t0, (b) In the morning of the surgery day=t1, (c) A day after surgery=t2. Blood samples were collected in each session, and serum levels of cytokines (IL-1β, IL-6) were measured. Fifteen control subjects went through the same procedure.

In the morning of the surgery day, there was a significant increase in the levels of both anxiety (STAI) (FIG. 15A) and depression (DACL) (FIG. 15B) ($F(2,82)$-3.871, $p<0.025$ and $F(2,82)=11.189$, $p<0.0001$, respectively). No change was found in the levels of fatigue and pain (FIGS. 15C and 15D, respectively). In the morning following surgery there was further increase in depression, but not in anxiety, alongside a significant increase in pain and fatigue ($F(2,80)=24.588$, $p<0.0001$ and $F(2,80)=10.148$, $p<0.0001$, respectively).

With regards to the cognitive parameters (FIG. 15E-15H), in the morning of the surgery day tests showed a significant decline in performance of the word list recall task (HVLT) ($F(2,70)=4.120$, $p<0.021$). In the morning following surgery, an additional decline was found in the word list recall as well as in the performance of a visual memory task involving a complex figure reconstruction (MCG)($F(2,70)=3.973$, $p<0.023$).

For each parameter (psychological performance, cytokine level, etc) differences were computed between each stressful situation (t1, t2) and baseline (t0). Pearson correlations were computed between cytokines levels and psychological variables (FIG. 16A-C).

In the morning of the surgery day (t1), there was a significant correlation between increased levels of IL-1 beta and the elevation in depressed mood ($r=0.525$) (FIG. 16 b).

In the morning following the surgery (t2), there were significant correlations between increased IL-1 levels and impaired immediate and delayed Logical memory (story recall test) ($r=-0.627$ and $-0.532$, respectively). Significant correlations were obtained between increased IL-6 levels and improved delayed recall in the Word List Recall (HVLT) test ($r=0.386$), as well as improved immediate and delayed Complex Figure recall test (MCG) ($r=0.502$ and $0.590$, respectively). There was a significant increase in IL-6 ($F(2,38)=29.114$, $p<0.0001$) (FIG. 16C).

Example 16

Selective Elimination of AChE-R mRNA in the Brain of EN301-Treated Mice

Experimental Procedure:

3 month old FVB/N female mice were injected intra-peritoneally daily with 500 μg/kg of EN301 (n=7) or with vehicle (PBS, n=6). EN301 corresponds to mEN101, defined herein as SEQ ID NO:2. This antisense oligonucleotide is targeted to a sequence within exon 2 of mouse AChE exon 2 sequence. EN301 was produced by Microsynth, Switzerland, at relatively large quantities for animal tests. The treatment persisted for 3 consecutive days, and the mice were sacrificed on day 4. Brain was collected, flash frozen in liquid nitrogen and stored at $-70°$ C.

Total RNA was extracted from the brain and RT-PCR reaction was conducted using primers targeting the common sequence in Exon 2 of murine AChE cDNA or the unique sequence in Exon 6, specific to the AChE-S variant. 5 μl samples were removed from the 50 μl PCR reaction mixture at cycles 25, 31 and 35. Samples were run on a 1.5% Agarose gel. The results of the PCR specific for the exon 2 sequence, after 31 cycles, are shown in FIG. 17A. Photographs were saved and fluorescence quantified using the PhotoShop software, and the results expressed in histograms (FIGS. 17B-17C).

Results:

The goal of the present experiment was to test for reduction in AChE gene expression under EN301 treatment, while ensuring that AChE-S mRNA levels are maintained reflecting sustained cholinergic neurotransmission.

Normalized to RNA quantities, EN301-treated brains showed a significant 25% reduction (p=0.01, Student's T-Test) in the common transcript levels (FIG. 17B), whereas the S variant showed a non-significant 17% increase (FIG. 17C), reflecting a relatively larger fraction of AChE-S mRNA out of the total content of mRNA as compared with the untreated brain.

The ratio between AChE-S:common (S/Com) transcripts showed that in the EN301-treated brain, the S/Com ratio is significantly increased (from 0.65 to 0.98). RT-PCR data cannot be used as such for comparing the absolute quantities of the analyzed transcripts, because different primer pairs may function with different efficacies. However, that these two tests point at the same direction (namely, that AChE-R but not AChE-S mRNA was reduced in the EN301-treated brains and that the relative concentration of AChE-S mRNA increased, albeit insignificantly, under treatment) supports the notion that this agent affects brain gene expression as well.

The present results lead to the conclusion that EN301 treatment causes selective destruction of AChE-R mRNA in the EN301 treated brains while maintaining essentially unmodified AChE-S levels. Note that to exert such an effect, EN301 does not necessarily have to cross the blood-brain barrier. Rather, by reducing the levels of peripheral AChE it would increase acetylcholine levels, suppressing the production by macrophages of pro-inflammatory cytokines e.g. IL-1 [Wang, H. et al. (2003) *Nature* 421, 384-8]. Because IL-1 promotes AChE gene expression [Li et al. (2000) *J. Neurosci.* 20, 149-155], and since the peripheral pro-inflammatory cytokines are known to affect the brain [Pick et al. (2004) *Annals NY Acad. Sci.* 1018, 85-98], such an effect will eventually reduce AChE-R levels in the brain as well.

Example 17

Animal Model for Guillain-Barre Syndrome and Inflammation-Associated Neuropathy

Intra-neural injection into a rat peripheral nerve is often used to study Guillain-Barre Syndrome GBS, testing the pathogenesis of the disease following nerve sheath impairment, i.e., examining the effect of intra-neural invasion of reactive soluble factors, and not the nerve sheath disruption per se. Indeed, serum obtained from GBS patients was reported to cause demyelination and conduction blocks [Harrison B. et al. (1984) *Ann. Neurol.* 15: 163-170; Saida T. et al. (1982) *Ann. Neurol.* 11:69-75], which are not elicited by intra-neural injection of anti-GM1 IgG or IgM [Harvey G. et al. (1995) *Muscle Nerve* 18: 388-394].

The inventors previously employed an animal model for GBS to test the effect of systemic exposure to Cj-LPS on the sciatic nerve [Ifergane (2003) id ibid.]. Following pre-sensitization with the immune responses activator-keyhole limpet hemocyanin (KLH), rats were systemically exposed to Cj-0: 19 LPS via intraperitoneal (i.p.) injection. Parallel to LPS exposure, minor focal sciatic nerve trauma was applied by intraneural (i.n.) injection of saline (FIG. 18A). Compound muscle action potential (CMAP) stimulated proximal to the neural injection site appeared lower than distally stimulated CMAP (referred as reduced proximal to distal ratio; PDR, see FIG. 18B, 18C). This indicates nerve conduction blocks (when PDR<0.5) which developed in rats that received an i.n. injection of saline concomitantly with the systemic Cj-LPS exposure. Conduction blocks appeared 1-3 days after the LPS exposure and spontaneously resolved after 8 days. Conduction blocks did not develop in rats which were systemically exposed to Cj-LPS without an intraneural injection, and neither in rats which were injected intraneurally directly with the Cj-LPS itself. Conduction blocks developed in 3 out of 10 intraneurally injected rats which were not exposed to Cj-LPS and in none of the animals which were intraneurally injected 8 days after Cj-LPS exposure. The differences between the test and control groups were statistically significant (P<0.01). Morphological analysis of the injected nerves revealed no morphological abnormalities (i.e. demyelination, axonal degeneration or inflammatory changes) on days 3 and 9 following i.n. injection, in either group. The fact that direct Cj-LPS i.n. injection did not result in conduction abnormality, suggests a non-direct mechanism, in which the Cj-LPS stimulates systemic production of a factor that causes conduction block in the peripheral nerves that it penetrates. Furthermore, similar results were observed in rats treated with *E. Coli* LPS. All the animals which were concomitantly treated by i.p. *E. Coli* LPS and i.n. saline, developed conduction blocks on one day following injection (average PDR=0.417, S.D. 0.06), which resolved in the following 2 days. This indicates that a systemic reaction common to both gram negative bacilli LPS induces a neural reaction if soluble factors penetrate through the nerve sheath.

To test this hypothesis, splenocytes from KLH pre-sensitized rats were exposed to Cj-LPS in a cell suspension for 48 hours. The medium of splenocytes which reacted with LPS in vitro (reactive splenocyte medium) was then injected intraneurally to the sciatic nerve of rats. This reactive medium was cell-free and devoid of IgG or IgM, and did not elicit any electrophysiological effect within 10 minutes following injection, indicating that it did not contain neuroinhibitory or toxic substances reminiscent of curare or tetrodotoxine which typically block ion channels within minutes. Nevertheless, one to 4 days following i.n. injection, CMAP stimulated proximal to the injection site was reduced in more than 70 percent of nerves, indicating a conduction block. Normal splenocyte medium (not reacted with LPS) induced a conduction block in only 6.2 percent of nerves which was significantly different (p<0.01). Conduction block duration was 1.44 plus or minus 1.02 days with resolution in 70 percent of the nerves. In this case as well, morphological analysis demonstrated no demyelination, axonal degeneration or inflammatory abnormalities, indicating that the electrophysiological pathology was not due to gross neural deformity, or myelin sheath and axonal degeneration. These results strengthen the hypothesis that an immune reaction to Cj-LPS similar to *E. Coli* LPS, produces a soluble factor which induces functional conduction abnormalities within penetrated nerves while the neural structures are yet preserved.

Example 18

Treatment with EN101 Inhibits Conduction Blocks

Figures 19A, 19B:
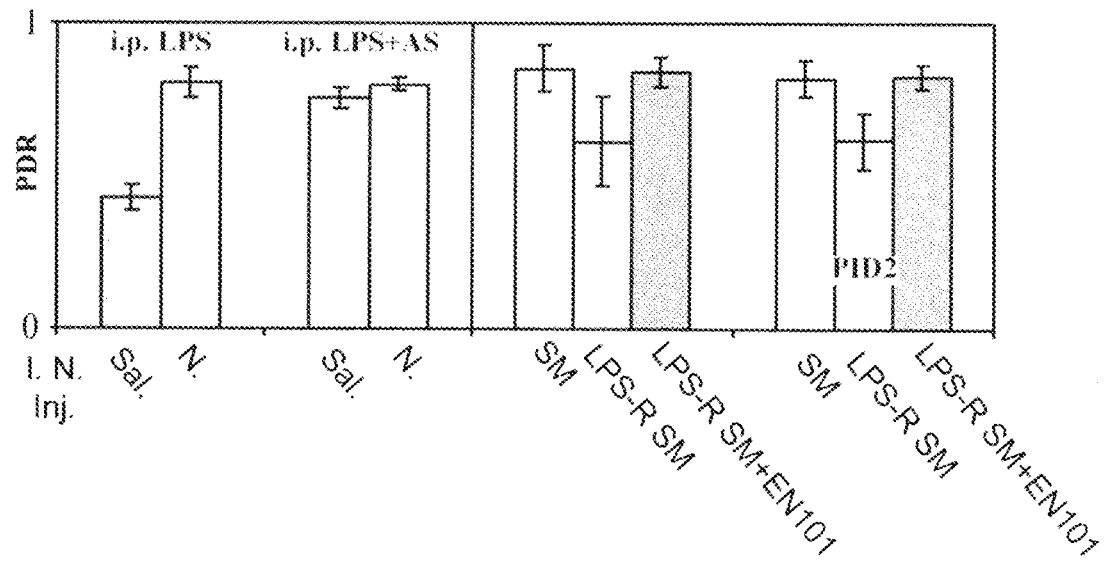

The inventors tested the participation of AChE-R in the sequence of events that follow exposure to LPS and lead to conduction abnormalities in the GBS model described above. Indeed, systemic (i.p.) treatment with EN101 (0.5 mg/kg) prevented formation of conduction blocks when applied with Cj-LPS parallel to i.n. saline injection. Treatment with EN101 significantly improved PDR (proximal to distal amplitude ratio, p<0.01), which became similar to non-i.n. injected controls (p=0.45; FIG. 19A). Furthermore, addition of EN101 (20 μmole) to i.n. injections of Cj-LPS reactive splenocyte medium prevented the appearance of nerve conduction block and reduction in PDR compared to control group injected with LPS-reacted splenocyte medium alone (P<0.05; FIG.

Figures 19C, 19D:
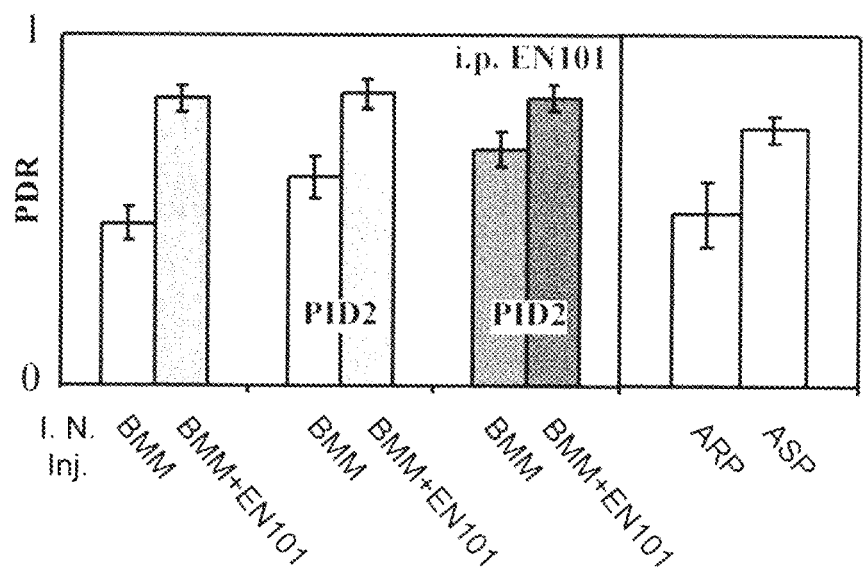

19B). Additionally, to simulate macrophage intra-neural invasion as detected in GBS, bone marrow-derived cultured macrophages were intra-neurally injected. These cells induced conduction blocks which initiated 1 day following injection, with resolution after 7 plus or minus 1 days. Concomitant i.n. EN101 injection abolished the appearance of conduction blocks or reduction in PDR (p<0.01; FIG. 19C). Furthermore, addition of EN101 by i.p. injection at the time of conduction block in non-EN101 treated injected nerves on day 1, increased PDR on the following day compared to animals that did not receive i.p. EN101 (t-test p<0.05). The direct causal effect of AChE-R on nerve conduction was examined by i.n. injection of synthetic ARP (1.4 nmole) to the sciatic nerve of adult naive rats. This treatment produced a transient nerve conduction block, which initiated 24 hrs following injection and lasted 48 hrs (FIG. 19D). Injection of AChE-Synaptic peptide (ASP; 1.4 nmole) as a negative control did not produce a conduction block, indicating the specificity of ARP for conduction blockade (p<0.05).

In a recent study, mild stress was shown to induce AChE-R in the hippocampus, and to interact intraneuronally with a scaffold protein RACK1 and through it, with its target, protein kinase CβII (PKCβII), in a manner suppressible by antisense prevention of AChE-R accumulation [Birikh (2003) id ibid.; Nijholt, I. et al. (2004) *Molecular Psychiatry* 9: 174-183]. In agreement with this, the inventors identified that LPS-reacted splenocyte medium i.n. injection increased PKCβII levels in sciatic nerve by immunoblot analysis, which was suppressed by EN101 treatment (FIG. 20). These results further support the hypothesis that AChE-R plays a key role in induction of functional nerve conduction blocks following immune activation by LPS exposure or i.n. invasion of macrophages, as evidenced in GBS, and strongly suggest that ARP is the active modulator in these processes. Nevertheless, AChE-R induction is not restricted to reaction to the *Campylobacter* type of LPS. Furthermore, the formation of nerve conduction block by direct i.n. injection of ARP indicates that AChE-R and ARP may affect nerve conduction in response to various inflammatory responses, where nerve sheath/blood nerve barrier is injured or disrupted, as exemplified in GBS. Hence, EN101 treatment to treat nerve conduction pathology is applicable for conditions that similarly induce AChE-R when concurrent nerve sheath disruption is present.

The invention claimed is:

1. A method for the treatment of inflammation of the gastrointestinal tract in a human subject in need thereof comprising administering to the subject a therapeutically effective amount of an inhibitor of AChE expression or a pharmaceutical composition comprising the same, said inhibitor of AChE expression being an antisense oligonucleotide having the nucleotide sequence selected from the group consisting of SEQ ID NO:7 and SEQ ID NO:1.

2. The method of claim 1, wherein said antisense oligonucleotide has the nucleotide sequence as denoted by SEQ ID NO:7.

3. The method of claim 1, wherein said antisense oligonucleotide or pharmaceutical composition comprising the same is administered daily in a dose of said antisense oligonucleotide of 150 or 500 mg/Kg/day.

4. The method of claim 1, wherein said antisense oligonucleotide or pharmaceutical composition comprising the same are administered orally.

5. The method of claim 1, wherein said antisense oligonucleotide is orally administered to said subject in need for at least 7 consecutive days.

6. The method of claim 1, wherein said antisense oligonucleotide is comprised in a pharmaceutical composition, said composition further optionally comprising at least one of pharmaceutically acceptable additives, carriers and diluents.

7. The method of claim 6, wherein said carrier is saline.

8. A method for treating an inflammatory condition in the gastrointestinal tract of a subject in need, comprising:
providing an antisense oligonucleotide directed against AChE, having the nucleotide sequence selected from the group consisting of SEQ ID NO:1 and SEQ ID NO:7;
providing a liquid carrier for mixing with said antisense oligonucleotide;
mixing said antisense oligonucleotide with said carrier to form a liquid composition; and
orally administering said liquid composition to said subject.

9. The method of claim 1, wherein the inflammation of the gastrointestinal tract is inflammatory bowel disease.

10. The method of claim 1, wherein the inflammation of the gastrointestinal tract is ulcerative colitis.

* * * * *

```
                       SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Antisense oligonucleoitde hEN101 targets human
      AChE

<400> SEQUENCE: 1
ctgccacgtt ctcctgcacc                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Antisense oligonucleotide mEN101 (EN301),
      targets mouse AChE

<400> SEQUENCE: 2
ctgcaatatt ttcttgcacc                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Antisense oligonucleotide rEN101, targets rat
      AChE

<400> SEQUENCE: 3
ctgccatatt ttcttgtacc                                               20
```

```
<210> SEQ ID NO 4
<211> LENGTH: 20
<212> TYPE: DNA
<213> ORGANISM: Homo sapiens

<400> SEQUENCE: 4
gggagaggag gaggaagagg                                                    20

<210> SEQ ID NO 5
<211> LENGTH: 50
<212> TYPE: RNA
<213> ORGANISM: Homo sapiens

<400> SEQUENCE: 5 cuaggggag aagagagggg uuacacuggc gggcucccac uccccuccuc                   50

<210> SEQ ID NO 6
<211> LENGTH: 50
<212> TYPE: RNA
<213> ORGANISM: Homo sapiens

<400> SEQUENCE: 6 ccggggacg ucgggguggg guggggaugg gcagagucug gggcucgucu                   50

<210> SEQ ID NO 7
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Antisense oligonucleotide hEN101, with the 3
      terminal residues modified
<220> FEATURE:
<221> NAME/KEY: modified_base
<222> LOCATION: (18)..(18)
<223> OTHER INFORMATION: 2-O-methylation
<220> FEATURE:
<221> NAME/KEY: modified_base
<222> LOCATION: (19)..(20)
<223> OTHER INFORMATION: cm

<400> SEQUENCE: 7
ctgccacgtt ctcctgcacc                                                   20
```